United States Patent
Zulak et al.

(10) Patent No.: US 9,260,728 B2
(45) Date of Patent: *Feb. 16, 2016

(54) **TERPENE SYNTHASES FROM *SANTALUM***

(71) Applicants: UNIVERSITY OF BRITISH COLUMBIA, Vancouver (CA); UNIVERSITY OF WESTERN AUSTRALIA, Crawley (AU); FOREST PRODUCTS COMMISSION, Rivervale (AU)

(72) Inventors: Katherine Zulak, Joondanna (AU); Christopher Jones, Joondanna (AU); Jessie Moniodis, Lesmurdie (AU); Joerg Bohlmann, Vancouver (CA)

(73) Assignees: University of British Columbia, Vancouver (CA); University of Western Australia, Crawley (AU); Forest Products Commission, Rivervale (AU)

(*) Notice: Subject to any disclaimer, the term of this patent is extended or adjusted under 35 U.S.C. 154(b) by 0 days.

This patent is subject to a terminal disclaimer.

(21) Appl. No.: 14/628,125

(22) Filed: Feb. 20, 2015

(65) Prior Publication Data

US 2015/0167021 A1    Jun. 18, 2015

Related U.S. Application Data

(63) Continuation of application No. 13/998,045, filed on Sep. 24, 2013, now Pat. No. 8,993,284, which is a continuation of application No. 13/261,101, filed on Apr. 18, 2012, now Pat. No. 8,569,025.

(60) Provisional application No. PCT/AU2010/000802, filed on Jun. 25, 2010.

(30) Foreign Application Priority Data

Jun. 29, 2009    (AU) ................ 2009903016

(51) Int. Cl.
| | | |
|---|---|---|
| C12P 7/04 | (2006.01) | |
| C12N 15/00 | (2006.01) | |
| C12Q 1/527 | (2006.01) | |
| C12Q 1/68 | (2006.01) | |
| G01N 33/573 | (2006.01) | |
| C12P 7/02 | (2006.01) | |
| C12P 5/00 | (2006.01) | |
| C12N 9/88 | (2006.01) | |
| C12P 15/00 | (2006.01) | |

(52) U.S. Cl.
CPC . *C12P 5/007* (2013.01); *C12N 9/88* (2013.01); *C12P 7/02* (2013.01); *C12P 15/00* (2013.01); *C12Q 1/527* (2013.01); *C12Q 1/6895* (2013.01); *G01N 33/573* (2013.01); *C12Y 402/03081* (2013.01); *C12Y 402/03082* (2013.01); *C12Y 402/03083* (2013.01)

(58) Field of Classification Search
CPC ............ C12N 9/88; C12P 7/02; C12P 15/00; C12P 5/007; C12Q 1/689; C12Q 1/5275; G01N 33/573
USPC ............ 435/252.3, 320.1, 183, 6.1; 536/23.2
See application file for complete search history.

(56) References Cited

U.S. PATENT DOCUMENTS

| | | | |
|---|---|---|---|
| 3,654,090 | A | 4/1972 | Schuurs et al. |
| 3,850,752 | A | 11/1974 | Schuurs et al. |
| 4,016,043 | A | 4/1977 | Schuurs et al. |
| 5,837,832 | A | 11/1998 | Chee et al. |
| 6,265,639 | B1 | 7/2001 | Croteau et al. |
| 6,531,303 | B1 | 3/2003 | Millis et al. |
| 8,569,025 | B2 | 10/2013 | Zulak et al. |
| 2008/0281135 | A1 | 11/2008 | Tissler et al. |
| 2011/0281257 | A1 | 11/2011 | Schalk |
| 2012/0208173 | A1 | 8/2012 | Zulak et al. |
| 2013/0189677 | A1 | 7/2013 | Breuil et al. |
| 2013/0224809 | A1 | 8/2013 | Bohlmann et al. |

FOREIGN PATENT DOCUMENTS

| | | |
|---|---|---|
| CN | 101194013 | 8/2013 |
| EP | 2376643 | 10/2011 |
| WO | 97/49989 | 12/1997 |
| WO | 98/49557 | 11/1998 |
| WO | 2004/031376 | 4/2004 |
| WO | 2006/134523 | 12/2006 |

(Continued)

OTHER PUBLICATIONS

Walker et al., "Strand displacement amplification—an isothermal, in vitro DNA amplification technique," Nucleic Acids Res. 20(7):1691-6 (Apr. 1992).

Williams et al., "Truncation of limonene synthase preprotein provides a fully active 'pseudomature' form of this monoterpene cyclase and reveals the function of the amino-terminal arginine pair," Biochem. 37(35):12213-20 (Sep. 1998).

Wu & Wallace, "The ligation amplification reaction (LAR)—amplification of specific DNA sequences using sequential rounds of template-dependent ligation," Genomics 4(4):560-9 (May 1989).

(Continued)

*Primary Examiner* — Maryam Monshipouri
(74) *Attorney, Agent, or Firm* — McDonnell Boehnen Hulbert & Berghoff LLP

(57) ABSTRACT

An isolated nucleic acid molecule that encodes a terpene synthase and is selected from among: a) a nucleic acid molecule comprising the sequence of nucleotides set forth in SEQ ID NO: 1, SEQ ID NO: 3 or SEQ ID NO: 5; b) a nucleic acid molecule that is a fragment of (a); c) a nucleic acid molecule comprising a sequence of nucleotides that is complementary to (a) or (b); and d) a nucleic acid molecule that encodes a terpene synthase having at least or at least about 60%, 65%, 70%, 75%, 80%, 85%, 90%, 95%, 96%, 97%, 98%, 99% identity to any one of (a)-(c); wherein the nucleic acid molecule encodes a terpene synthase.

26 Claims, 26 Drawing Sheets

(56) References Cited

FOREIGN PATENT DOCUMENTS

| WO | 2009/044336 | 5/2009 |
|---|---|---|
| WO | 2009/109597 | 9/2009 |
| WO | 2010/067309 | 6/2010 |
| WO | 2011/000026 | 1/2011 |
| WO | 2013/075239 | 5/2013 |
| WO | 2013/110191 | 8/2013 |

OTHER PUBLICATIONS

Zerbe et al., "Bifunctional cis-abienol synthase from Abies balsamea discovered by transcriptome sequencing and its implications for diterpenoid fragrance production," J Biol Chem. 287(15): 12121-31 (Apr. 2012).

Zerbe et al., "Mutational analysis of white spruce (*Picea glauca*) ent-kaurene synthase (PgKS) reveals common and distinct mechanisms of conifer diterpene synthases of general and specialized metabolism," Phytochemistry 74:30-9 (Feb. 2012).

Zulak et al., "Targeted proteomics using selected reaction monitoring reveals the induction of specific terpene synthases in a multi-level study of methyl jasmonate-treated Norway spruce (*Picea abies*)," Plant J. 60:1015-30 (Dec. 2009).

Zulak et al., "Terpenoid biosynthesis and specialized vascular cells of conifer defense," J Integr Plant Biol. 52 (1):86-97 (Jan. 2010).

International Search Report and Written Opinion by the International Searching Authority, issued Sep. 10, 2010, in connection with corresponding International Patent Application No. PCT/AU2010/000802 (16 pages).

Extended European Search Report, issued Nov. 30, 2012, in connection with European Patent Application No. 10793414.3 (7 pages).

Response to Extended European Search Report, submitted Jun. 25, 2013, in connection with European Patent Application No. 10793414.3, 13 pages.

Examination Report, issued Dec. 2, 2013, in connection with Canadian Patent Application No. 2,766,810, 3 pages.

Response to Office Action, filed Mar. 27, 2014, in connection with Canadian Patent Application No. 2, 766,810, 29 pages.

English Language Instructions and Response to Office Action, filed Jun. 12, 2014, in connection with Chinese Patent Application No. 201080038885.4, 27 pages.

English Translation of Office Action, issued Jan. 28, 2014, in connection with Chinese Patent Application No. 201080038885.4, 9 pages.

Office Action issued Oct. 11, 2014, and English Language translation, in connection with Chinese Patent Application No. 201080038885.4, 6 pages.

Official Action, issued Mar. 7, 2013, in connection with Chinese Patent Application No. 201080038885.4, 16 pages.

Response to Official Action, submitted Sep. 23, 2013, in connection with Chinese Patent Application No. 201080038885.4, 41 pages.

Examination Report, issued Oct. 7, 2013, in connection with European Patent Application No. 10793414.3, 4 pages.

Response to Office Action, filed Apr. 14, 2014, in connection with European Patent Application No. 10793414.3, 60 pages.

English Translation of Office Action, issued Apr. 10, 2014, in connection with Israeli Patent Application No. 217221, 3 pages.

Notice of Allowance, issued Jun. 14, 2013, in connection with U.S. Appl. No. 13/261,101, 12 pages.

English Translation of Office Action, issued May 5, 2015 in connection with Chinese Patent Application No. 201080038885.4, 1 page.

Decision to grant a European Patent, issued May 12, 2015, in connection with European Patent Application No. 10793414.3, 3 pages.

English translation of response to Office Action, filed Dec. 8, 2014, in connection with Israeli Patent Application No. 217221, 15 pages.

Allylix, "Protein engineering and chembiosynthesis to produce novel sesquiterpenoids," Presentation at Bio World Congress on Industrial Biotechnology & Bioprocessing, Washington, D.C. (Jun. 28, 2010) (19 pages).

Altschul et al., "Basic local alignment search tool," J Mol Biol. 215(3):403-10 (Oct. 1990).

Asadollahi et al., "Production of plant sesquiterpenes in *Saccharomyces cerevisiae*: effect of ERG9 repression on sesquiterpene biosynthesis," Biotechnol Bioeng. 99:666-77 (2007).

Asseline et al., "Nucleic acid-binding molecules with high affinity and base sequence specificity: intercalating agents covalently linked to oligodeoxynucleotides," Proc Natl Acad Sci U S A 81(11):3297-301 (Jun. 1984).

Back & Chappell, "Identifying functional domains within terpene cyclases using a domain-swapping strategy," Proc Natl Acad Sci U S A. 93(13):6841-5 (Jun. 1996).

Barany, "The ligase chain reaction in a PCR world," PCR Methods Appl. 1:5-16 (Aug. 1991).

Bleeker et al., "RNA-seq discovery, functional characterization, and comparison of sesquiterpene synthases from Solanum lycopersicum and Solanum habrochaites trichomes," Plant Mol Biol. 77:323-36 (Aug. 2011).

Bohlmann et al., "cDNA cloning, characterization, and functional expression of four new monoterpene synthase members of the Tpsd gene family from Grand Fir (*Abies grandis*)," Arch Biochem Biophys. 368(2):232-43 (Aug. 1999).

Bohlmann et al., "Plant terpenoid synthases: molecular biology and phylogenetic analysis," Proc Natl Acad Sci U S A. 95(8):4126-33 (Apr. 1998).

Bohlmann & Keeling, "Terpenoid biomaterials," Plant J. 54(4):656-69 (May 2008).

Bohlmann, "Terpenoid synthases—from chemical ecology and forest fires to biofuels and bioproducts," Structure 19 (12):1730-1 (Dec. 2011).

Cane et al., "Trichodiene biosynthesis and the stereochemistry of the enzymatic cyclization of farnesyl pyrophosphate," Bioorganic Chemistry 13(3):246-65 (Sep. 1985).

Cane, "Enzymatic formation of sesquiterpenes," Chemical Reviews 90(7):1089-103 (Nov. 1990).

Carillo et al., "The multiple sequence alignment problem in biology," SIAM Journal of Applied Mathematics 48 (5):1073-82 (Oct. 1988).

Chen et al., "The family of terpene synthases in plants: a mid-size family of genes for specialized metabolism that is highly diversified throughout the kingdom," Plant J. 66(1):212-29 (Apr. 2011).

Chothia & Lesk, "The relation between the divergence of sequence and structure in proteins," EMBO J. 5(4):823-6 (Apr. 1986).

Compton, "Nucleic acid sequence-based amplification," Nature 350(6313):91-2 (Mar. 1991).

Devereux et al., "A comprehensive set of sequence analysis programs for the VAX," Nucleic Acids Res. 12 (1):387-95 (Jan. 1984).

Dewick, "The biosynthesis of C5-C25 terpenoid compounds," Nat Prod Rep. 19(2):181-222 (Apr. 2002).

Diaz-Chavez et al., "Biosynthesis of sandalwood oil: *Santalum album* CYP76F cytochromes P450 produce santalols and bergamotol," PLoS One 8(9):e75053 (Sep. 2013).

Duck et al., "Probe amplifier system based on chimeric cycling oligonucleotides," Biotechniques 9(2):142-8 (Aug. 1990).

Genbank Accession No. AAA86337.1, "vetispiradiene synthase, partial [Hyoscyamus muticus]," Published on Jan. 30, 1996 [online][retrieved on Mar. 19, 2012] Retrieved from:<URL: ncbi.nlm.nih.gov/protein/AAA86337.1, 2 pages.

Genbank Accession No. AAC05727.1, "d-selinene synthase [Abies grandis]," Published on Mar. 17, 1998 [online] [retrieved on Mar. 19, 2012] Retrieved from:<URL: ncbi.nlm.nih.gov/protein/AAC05727.1, 2 pages.

Genbank Accession No. AAC05728.1, "gamma-humulene synthase [Abies grandis]," Published on Mar. 17, 1998 [online] [ retrieved on Mar. 19, 2012] Retrieved from:<URL: ncbi.nlm.nih.gov/protein/AAC05728.1, 2 pages.

Genbank Accession No. AAC39443.1, "ent-kaurene synthase [Arabidopsis thaliana]," Published on Apr. 17, 1998 [online][retrieved on Mar. 19, 2012] Retrieved from:<URL: ncbi.nlm.nih.gov/protein/AAC39443.1, 2 pages.

Genbank Accession No. AAF61439.1, "amorpha-4,11-diene synthase [Artemisia annua]," Published on Sep. 25, 2000 [online][retrieved on Mar. 19, 2012] Retrieved from:<URL: ncbi.nlm.nih.gov/protein/AAF61439.1, 2 pages.

(56) References Cited

OTHER PUBLICATIONS

Genbank Accession No. AAF61453.1, "beta-phellandrene synthase [Abies grandis]," Published on Jul. 24, 2001 [online] [retrieved on Mar. 19, 2012] Retrieved from:<URL: ncbi.nlm.nih.gov/protein/AAF61453.1, 2 pages.
Genbank Accession No. AAO73863.1, "(+)-3-carene synthase [Picea abies]," Published on Mar. 27, 2003 [online] [retrieved on Mar. 19, 2012] Retrieved from:<URL:ncbi.nlm.nih.gov/protein/AAO73863.1, 2 pages.
Genbank Accession No. AAR99061.1, "(−)-germacrene D synthase [Populus trichocarpa x Populus deltoides]," Published on Sep. 13, 2004 [online][retrieved on Mar. 19, 2012] Retrieved from:<URL:ncbi.nlm.nih.gov/protein/AAR99061.1, 2 pages.
Genbank Accession No. AAS47691.1, "levopimaradiene/abietadiene synthase [Picea abies]," Published on Aug. 4, 2009 [online][retrieved on Mar. 19, 2012] Retrieved from:<URL: ncbi.nlm.nih.gov/protein/AAS47691.1, 2 pages.
Genbank Accession No. AAS79351.1, "(−)-a-terpineol synthase [Vitis vinifera]," Published on Nov. 7, 2007 [online] [retrieved on Mar. 19, 2012] Retrieved from:<URL:ncbi.nlm.nih.gov/protein/AAS79351.1, 2 pages.
Genbank Accession No. AAV63788.1, "alpha-zingiberene synthase [Ocimum basilicum]," Published on Nov. 20, 2004 [online][retrieved on Mar. 19, 2012] Retrieved from:<URL: ncbi.nlm.nih.gov/protein/AAV63788.1, 2 pages.
Genbank Accession No. AB438045, "Backhousia citriodora mRNA for linalool synthase, complete cds," Published on Jun. 11, 2008 [online][retrieved on Mar. 19, 2012] Retrieved from:<URL: ncbi.nlm.nih.gov/nuccore/AB438045, 2 pages.
Genbank Accession No. ACF24767.1, "monoterpene synthase [Santalum album]," Published on Feb. 9, 2008 [online] [retrieved on Mar. 19, 2012] Retrieved from: <URL:ncbi.nlm.nih.gov/protein/ACF24767.1, 2 pages.
Genbank Accession No. ACF24768.1, "sesquiterpene synthase [Santalum album]," Published on Feb. 9, 2008 [online] [retrieved on Mar. 19, 2012] Retrieved from:<URL:ncbi.nlm.nih.gov/protein/ACF24768.1, 2 pages.
Genbank Accession No. ADB55710.1, "(−)-ent-kaurene synthase [Picea sitchensis]," Published on May 3, 2010 [online] [retrieved on Mar. 19, 2012] Retrieved from:<URL:ncbi.nlm.nih.gov/protein/ADB55710.1, 2 pages.
Genbank Accession No. AF484125, "Nicotiana attenuata 5-epi-aristolochene synthase 37 mRNA, complete cds," Published on Apr. 15, 2003 [online][retrieved on Mar. 19, 2012] Retrieved from:<URL:ncbi.nlm.nih.gov/nuccore/AF484125, 2 pages.
Genbank Accession No. AF514287_1, "(+)-limonene synthase 1 [Citrus limon]," Published on Aug. 23, 2002 [online] [retrieved on Mar. 19, 2012] Retrieved from:<URL:ncbi.nlm.nih.gov/protein/21435703, 2 pages.
Genbank Accession No. BAF02832.1, "monoterpene synthase [Eucalyptus globulus]," Published on Nov. 8, 2006 [online][retrieved on Mar. 19, 2012] Retrieved from:<URL:ncbi.nlm.nih.gov/protein/BAF02832.1, 2 pages.
Genbank Accession No. BAG82825, "linalool synthase [Backhousia citriodora]," Published on Jun. 11, 2008 [online] [retrieved on Mar. 19, 2012] Retrieved from:<URL:ncbi.nlm.nih.gov/protein/BAG82825.1, 2 pages.
Genbank Accession No. CAA06614.1, "5-epi-aristolochene synthase [*Capsicum annuum* var. *annuum*]," Published on Jan. 30, 1996 [online][retrieved on Nov. 14, 2006] Retrieved from:<URL:ncbi.nlm.nih.gov/protein/CAA06614.1, 2 pages.
Genbank Accession No. CAA77191.1, "(+)-delta-cadinene synthase [Gossypium arboreum]," Published on Nov. 14, 2006 [online][retrieved on Mar. 19, 2012] Retrieved from:<URL:ncbi.nlm.nih.gov/protein/CAA77191.1, 2 pages.
Genbank Accession No. DQ785793.1, "Salvia fruticosa cineole synthase (CinS1) mRNA, complete cds," Published on Feb. 8, 2007 [online ][retrieved on Mar. 19, 2012] Retrieved from:<URL:ncbi.nlm.nih.gov/nuccore/DQ785793.1, 2 pages.
Genbank Accession No. DQ785794.1, "Salvia pomifera sabinene synthase (SabS1) mRNA, partial cds," Published on Feb. 8, 2007 [online ][retrieved on Mar. 19, 2012] Retrieved from:<URL:ncbi.nlm.nih.gov/nuccore/DQ785794.1, 2 pages.
Genbank Accession No. EQ973796.1, "Ricinus communis genomic scaffold scf_1106159309750, whole genome shotgun sequence," Published on Dec. 2, 2009 [online][retrieved on Mar. 19, 2012] Retrieved from:<URL:ncbi.nlm.nih.gov/nuccore/EQ973796.1, 2 pages.
Genbank Accession No. FB299123, "Sequence 1 from Patent WO2006134523," Published on Sep. 24, 2008 [online] [retrieved on Mar. 19, 2012] Retrieved from:<URL:ncbi.nlm.nih.gov/nuccore/FB299123, 1 page.
Genbank Accession No. FB299124, "Sequence 2 from Patent WO2006134523," Published on Sep. 24, 2008 [online] [retrieved on Mar. 19, 2012] Retrieved from:<URL:ncbi.nlm.nih.gov/nuccore/FB299124, 1 page.
Genbank Accession No. FB299125, "Sequence 3 from Patent W02006134523," Published on Sep. 24, 2008 [online] [retrieved on Mar. 19, 2012] Retrieved from:<URL:ncbi.nlm.nih.gov/nuccore/FB299125, 1 page.
Genbank Accession No. EU798692, "Predicted: Vitis vinifera (−)-a-terpineol synthase (LOC100232956), mRNA." Published on Feb. 9, 2008 [online][retrieved on Apr. 22, 2011] Retrieved from:<URL: ncbi.nlm.nih.gov/nuccore/XM_002269696, 1 page.
Genbank Accession No. XM_002269696,"Santalum album monoterpene synthase mRNA, complete cds." Published on Mar. 20, 2009. [online][retrieved Apr. 22, 2011] Retrieved from:<URL: ncbi.nlm.nih.gov/nuccore/EU798692, 1 page.
Genbank Accession No. AB110637, "Citrus unshiu CitMTSE2 mRNA for d-limonene AC synthase," Published on Sep. 1, 2009 [online][retrieved Feb. 6, 2014] Retrieved from: URL:ncbi.nlm.nih.gov/nuccore/AB110637.1, 1 page.
Genbank Accession No. AAM53944.1, "(+)-limonene synthase 1 [Citrus limon]," Published on Aug. 23, 2002 [online] [retrieved on Mar. 19, 2012] Retrieved from:<URL:ncbi.nlm.nih.gov/protein/AAM53944.1.
Genbank Accession No. EU798692.1, "Santalum album monoterpene synthase mRNA, complete AE cds," Published on Feb. 9, 2008 [online][retrieved on Mar. 19, 2012] Retrieved from:<URL:ncbi.nlm.nih.gov/nuccore/EU798692.1.
Gribskov & Burgess, "Sigma factors from *E. coli, B. subtilis*, phage SP01, and phage T4 are homologous proteins," Nucleic Acids Res. 14(16):6745-63 (Aug. 1986).
Guatelli et al., "Isothermal, in vitro amplification of nucleic acids by a multienzyme reaction modeled after retroviral replication," Proc Natl Acad Sci U.S.A. 87:1874-8 (Mar. 1990).
Hamberger & Bohlmann, "Cytochrome P450 mono-oxygenases in conifer genomes: discovery of members of the terpenoid oxygenase superfamily in spruce and pine," Biochem Soc Trans. 34(Pt 6):1209-14 (Dec. 2006).
Hamberger et al., "Evolution of diterpene metabolism: Sitka spruce CYP720B4 catalyzes multiple oxidations in resin acid biosynthesis of conifer defense against insects," Plant Physiol. 157: 1677-95 (Dec. 2011).
IUPAC-IUB Commission on Biochemical Nomenclature, "A one-letter notation for amino acid sequences. Tentative rules," J Biol Chem. 243(13):3557-9 (Jul. 1968).
Jones et al., "Quantitative co-occurrence of sesquiterpenes; a tool for elucidating their biosynthesis in Indian sandalwood, *Santalum album*," Phytochemistry 67(22):2463-8 (Nov. 2006).
Jones, "Isolation of cDNAs and functional characterisation of two multi-product terpene synthase enzymes from sandalwood, *Santalum album* L.," Arch Biochem Biophys. 477(1):121-30 (Sep. 2008).
Jones et al., "Sandalwood fragrance biosynthesis involves sesquiterpene synthases of both the terpene synthase (TPS)-a and TPS-b subfamilies, including santalene synthases," J Biol Chem. 286(20):17445-54 (May 2011).
Kampranis et al., "Rational conversion of substrate and product specificity in a Salvia monoterpene synthase: structural insights into the evolution of terpene synthase function," Plant Cell. 19(6):1994-2005 (Jun. 2007).

(56) References Cited

OTHER PUBLICATIONS

Keeling & Bohlmann, "Diterpene resin acids in conifers," Phytochemistry 67(22):2415-23 (Nov. 2006).

Keeling et al., "Functional plasticity of paralogous diterpene synthases involved in conifer defense," Proc Natl Acad Sci U S A. 105(3):1085-90 (Jan. 2008).

Keeling & Bohlmann, "Genes, enzymes and chemicals of terpenoid diversity in the constitutive and induced defence of conifers against insects and pathogens," New Phytol. 170(4):657-75 (2006).

Keeling et al., "Identification and functional characterization of monofunctional ent-copalyl diphosphate and ent-kaurene synthases in white spruce reveal different patterns for diterpene synthase evolution for primary and secondary metabolism in gymnosperms," Plant Physiol. 152(3):1197-208 (Mar. 2010).

Keeling et al., "The primary diterpene synthase products of Picea abies levopimaradiene/abietadiene synthase (PaLAS) are epimers of a thermally unstable diterpenol," J Biol Chem. 286(24):21145-53 (Apr. 2011).

Keeling et al., "Transcriptome mining, functional characterization, and phylogeny of a large terpene synthase gene family in spruce (*Picea* spp.)," BMC Plant Biol. 11:43 (Mar. 2011).

Kolosova et al., "Isolation of high-quality RNA from gymnosperm and angiosperm trees," Biotechniques 36(5):821-4 (May 2004).

Kwoh et al., "Transcription-based amplification system and detection of amplified human immunodeficiency virus type 1 with a bead-based sandwich hybridization format," Proc Natl Acad Sci U S A. 86(4):1173-7 (Feb. 1989).

Kwok et al., "Effects of primer-template mismatches on the polymerase chain reaction: human immunodeficiency virus type 1 model studies," Nucleic Acids Res. 18(4):999-1005 (Feb. 1990).

Landegren et al., "DNA diagnostics—molecular techniques and automation," Science 242(4876):229-37 (Oct. 1988).

Lizardi & Kramer, "Exponential amplification of nucleic acids: new diagnostics using DNA polymerases and RNA replicases," Trends Biotechnol. 9(2):53-8 (Feb. 1991).

Lomeli et al., "Quantitative assays based on the use of replicatable hybridization probes," Clin Chem. 35(9): 1826-31 (Sep. 1989).

Lucker et al., "Vitis vinifera terpenoid cyclases: functional identification of two sesquiterpene synthase cDNAs encoding (+)-valencene synthase and (−)-germacrene D synthase and expression of mono- and sesquiterpene synthases in grapevine flowers and berries," Phytochemistry 65(19):2649-59 (Oct. 2004).

Martin et al., "Functional characterization of nine Norway spruce TPS genes and evolution of gymnosperm terpene synthases of the TPS-d subfamily," Plant Physiol. 135:1908-27 (Aug. 2004).

Martin & Bohlmann, "Identification of Vitis vinifera H-alpha-terpineol synthase by in silico screening of full-length cDNA ESTs and functional characterization of recombinant terpene synthase," Phytochemistry 65(9):1223-9 (May 2004).

Martin et al., "The bouquet of grapevine (*Vitis vinifera* L. cv. Cabernet Sauvignon) flowers arises from the biosynthesis of sesquiterpene volatiles in pollen grains," Proc Natl Acad Sci U S A. 106(17):7245-50 (Apr. 2009).

Matsukura et al., "Phosphorothioate analogs of oligodeoxynucleotides: inhibitors of replication and cytopathic effects of human immunodeficiency virus," Proc Natl Acad Sci U S A. 84:7706-10 (Nov. 1987).

Miller et al., "Insect-induced conifer defense. White pine weevil and methyl jasmonate induce traumatic resinosis, de novo formed volatile emissions, and accumulation of terpenoid synthase and putative octadecanoid pathway transcripts in Sitka spruce," Plant Physiol. 137(1):369-82 (Jan. 2005).

Miller et al., "Nonionic nucleic acid analogues. Synthesis and characterization of dideoxyribonucleoside methylphosphonates," Biochemistry 18(23):5134-43 (Nov. 1979).

Mikayama et al., "Molecular cloning and functional expression of a cDNA encoding glycosylation-inhibiting factor," Proc Natl Acad Sci U S A. 90:10056-60 (Nov. 1993).

Needleman & Wunsch, "A general method applicable to the search for similarities in the amino acid sequence of two proteins," J Mol Biol. 48(3):443-53 (Mar. 1970).

Nielsen et al., "Sequence specific inhibition of DNA restriction enzyme cleavage by PNA," Nucleic Acids Res. 21 (2):197-200 (Jan. 1993).

Nielsen, "Sequence-selective DNA recognition by synthetic ligands," Bioconjug Chem. 2(1):1-12 (Jan.-Feb. 1991).

O'Maille et al., "A single-vial analytical and quantitative gas chromatography-mass spectrometry assay for terpene synthases," Anal Biochem. 335(2):210-7 (Dec. 2004).

Pearson & Lipman, "Improved tools for biological sequence comparison," Proc Natl Acad Sci U S A. 85(8):2444-8 (Apr. 1988).

Ralph et al., "A conifer genomics resource of 200,000 spruce (*Picea* spp.) ESTs and 6,464 high-quality, sequence-finished full-length cDNAs for Sitka spruce (*Picea sitchensis*)," BMC Genomics 9:484 (Oct. 2008).

Ro & Bohlmann, "Diterpene resin acid biosynthesis in loblolly pine (*Pinus taeda*): functional characterization of abietadiene/levopimaradiene synthase (PtTPS-LAS) cDNA and subcellular targeting of PtTPS-LAS and abietadienol/abietadienal oxidase (PtAO, CYP720B1)," Phytochemistry 67(15):1572-8 (Aug. 2006).

Ro et al., "Loblolly pine abietadienol/abietadienal oxidase PtAO (CYP720B1) is a multifunctional, multisubstrate cytochrome P450 monooxygenase," Proc Natl Acad Sci U S A. 102(22):8060-5 (May 2005).

Rudinger, J. "Characteristics of the amino acids as components of a peptide hormone sequence," found in Peptide Hormones, Parsons, J. ( ed.), University Park Press; pp. 1-7 (1976).

Saito et al., "Diastereo and enantio-controlled synthesis of sandalwood constituents (−)-β-santalene and (+)-epi-β-santalene starting from the same (+)-norcamphor," Tetrahedron Letters 36(49):9003-6 (Dec. 1995).

Saiki et al., "Primer-directed enzymatic amplification of DNA with a thermostable DNA polymerase," Science 239 (4839):487-91 (Jan. 1988).

Sambrook et al., "Chapter 11: Synthetic Oligonucleotide Probes," in Molecular Cloning: A Laboratory Manual, 2nd Ed., 61 pages, Cold Spring Harbor Laboratory Press, Cold Spring Harbor, New York (1989).

Schardl et al., "Design and construction of a versatile system for the expression of foreign genes in plants," Gene 61(1):1-11 (1987).

Schwartz & Dayhoff, Eds., "Chapter 23: Matrices for Detecting Distant Relationships," in the Atlas of Protein Sequence and Structure, National Biomedical Research Foundation, pp. 353-358 (1979).

Shimada et al. "Isolation and characterization of a new d-limonene synthase gene with a different expression pattern in Citrus unshiu Marc," Scientia Horticulturae 105(4):507-512 (2005).

Smith & Waterman, "Comparison in biosequences," Adv. Appl. Math. 2(4):482-9 (Dec. 1981).

Stemmer, "DNA shuffling by random fragmentation and reassembly: in vitro recombination for molecular evolution," Proc Natl Acad Sci U S A. 91:10747-51 (Oct. 1994).

Turner & Croteau, "Organization of monoterpene biosynthesis in Mentha. Immunocytochemical localizations of geranyl diphosphate synthase, limonene-6-hydroxylase, isopiperitenol dehydrogenase, and pulegone reductase," Plant Physiol. 136(4):4215-27 (Dec. 2004).

Figure 4

```
                        Santalene Synthase S album.txt
>Contig2333 Santalene synthase 334(FL)
GGCCACAAAATAAGTCTCTTGTTCTGTTCTTTTGATCTCGTTTTATACTCAGCTCTCTCACTAATGGATTCTTCCACCGCCACC
GCCATGACAGCTCCATTCATTGATCCTACTGATCATGTGAATCTCAAAACTGATACGGATGCCTCAGAGAATCGAAGGATGGGA
AATTATAAACCCAGCATTTGGAATTATGATTTTTTACAATCACTTGCAACTCATCACAATATTGTGGAAGAGAGGCATCTAAAG
CTAGCTGAGAAGCTGAAGGGCCAAGTGAAGTTTATGTTTGGGGCACCAATGGAGCCGTTAGCAAAGCTGGAGCTTGTGGATGTG
GTTCAAAGGCTTGGGCTAAACCACCTATTTGAGACAGAGATCAAGGAAGCGCTGTTTAGTATTTACAAGGATGGGAGCAATGGA
TGGTGGTTTGGCCACCTTCATGCGACATCTCTCCGATTTAGGCTGCTACGACAGTGTGGGCTTTTTATTCCCCAAGATGTGTTT
AAAACGTTCCAAAACAAGACTGGGGAATTTGATATGAAACTTTGTGACAACGTAAAAGGGCTGCTGAGCTTATATGAAGCTTCA
TACTTGGGATGGAAGGGTGAAAACATCCTAGATGAAGCCAAGGCCTTCACCACCAAGTGCTTGAAAAGTGCATGGGAAAATATA
TCCGAAAAGTGGTTAGCCAAAAGAGTGAAGCATGCATTGGCTTTGCCTTTGCATTGGAGAGTCCCTCGAATCGAAGCTAGATGG
TTCATTGAGGCATATGAGCAAGAAGCGAATATGAACCCAACACTACTCAAACTCGCAAAATTAGACTTTAATATGGTGCAATCA
ATTCATCAGAAAGAGATTGGGGAATTAGCAAGGTGGTGGGTGACTACTGGCTTGGATAAGTTAGCCTTTGCCAGGAATAATTTA
CTGCAGAGCTATATGTGGAGCTGCGCGATTGCTTCCGACCCGAAGTTCAAACTTGCTAGAGAAACTATTGTCGAAATCGGAAGT
GTACTCACAGTTGTTGACGATGGATATGACGTCTATGGTTCAATCGACGAACTTGATCTCTACACAAGCTCCGTTGAAAGGTGG
AGCTGTGTGGAAATTGACAAGTTGCCAAACACGTTAAAATTAATTTTTATGTCTATGTTCAACAAGACCAATGAGGTTGGCCTT
CGAGTCCAGCATGAGCGAGGCTACAATAGCATCCCTACTTTTATCAAAGCGTGGGTTGAACAGTGTAAATCATACCAGAAAGAA
GCAAGATGGTTCCACGGGGGACACACGCCTCCATTGGAAGAATATAGCTTGAATGGACTTGTTTCCATAGGATTCCCTCTCTTG
TTAATCACGGGCTACGTGGCAATCGCTGAGAACGAGGCTGCACTGGATAAAGTGCACCCCCTTCCTGATCTTCTGCACTACTCC
TCCCTCCTTAGTCGCCTCATCAATGATATAGGAACGTCTCCGGATGAGATGGCAAGAGGCGATAATCTGAAGTCAATCCATTGT
TACATGAACGAAACTGGGGCTTCCGAGGAAGTTGCTCGTGAGCACATAAAGGGAGTAATCGAGGAGAATTGGAAAATACTGAAT
CAGTGCTGCTTTGATCAATCTCAGTTTCAGGAGCCTTTTATAACCTTCAATTTGAACTCTGTTCGAGGGTCTCATTTCTTCTAT
GAATTTGGGGATGGCTTTGGGGTGACGGATAGCTGGACAAAGGTTGATATGAAGTCCGTTTTGATCGACCCTATTCCTCTCGGC
GAGGAGTAGTAAGCTCGAAGCTTATGTTTGGTTTATGGTGATAGTGGTTCGACAAAAATATAACATCGGACAGGAGTATCTATT
TTTAATGATCGTGAGTTAAATAGGTAAGAAATATCTATTTTCGCTCATGATTCATAGAAATATTATTCCTTACACGTTATATTTC
TATCAAATAACTATTTTATTCCCGTAAGCCAACTTTAACTTTACTCTTAAGGGTCACTAGTGGTTTTACTATATAATAAGTCAA
CTAGCTTGAAGTAATAGAATAAAGGTTTGTTTTTAAGAGGGTTATGCACTACGGTTTCGATTGTCTTTTACTAATAAGTTTCTT
AACGAAACTCAGATGCTTTTTGGGATCATTCCCAAGGGATTTGTGCTTGTATTATCATCGTCTCTCTTATTAATATATTCCCCT
TTATGGCTGGTGTGGAAAAAAAAAAAAAAAAAAAAAAAAA
```

Figure 5

```
MDSSTATAMTAPFIDPTDHVNLKTDTDASENRRMGNYKPSIWNYDFLQSLATHHNIVEERHLKLAEKLKGQV
KFMFGAPMEPLAKLELVDVVQRLGLNHLFETEIKEALFSIYKDGSNGWWFGHLHATSLRFRLLRQCGLFIPQ
DVFKTFQNKTGEFDMKLCDNVKGLLSLYEASYLGWKGENILDEAKAFTTKCLKSAWENISEKWLAKRVKHAL
ALPLHWRVPRIEARWFIEAYEQEANMNPTLLKLAKLDFNMVQSIHQKEIGELARWWVTTGLDKLAFARNNLL
QSYMWSCAIASDPKFKLARETIVEIGSVLTVVDDGYDVYGSIDELDLYTSSVERWSCVEIDKLPNTLKLIFM
SMFNKTNEVGLRVQHERGYNSIPTFIKAWVEQCKSYQKEARWFHGGHTPPLEEYSLNGLVSIGFPLLLITGY
VAIAENEAALDKVHPLPDLLHYSSLLSRLINDIGTSPDEMARGDNLKSIHCYMNETGASEEVAREHIKGVIE
ENWKILNQCCFDQSQFQEPFITFNLNSVRGSHFFYEFGDGFGVTDSWTKVDMKSVLIDPIPLGEE*
```

```
MetAspSerSerThrAspThrAspMetThrAspProPheIleAspProThrAspHisValAsnLeuLysThr
AspThrAspAspSerGluAsnArgArgMetglyAsnTyrLysProSerIleTrpAsnTyrAspPheLeuGln
SerLeuAspThrHisHisAsnIleValGluGluArgHisLeuLysLeuAspGluLysLeuLysglyGlnVal
LysPheMetPheglyAspProMetGluProLeuAspLysLeuGluLeuValAspValValGlnArgLeugly
LeuAsnHisLeuPheGluThrGluIleLysGluAspLeuPheSerIleTyrLysAspglySerAsnglyTrp
TrpPheglyHisLeuHisAspThrSerLeuArgPheArgLeuLeuArgGlnCysglyLeuPheIleProGln
AspValPheLysThrPheGlnAsnLysThrglyGluPheAspMetLysLeuCysAspAsnValLysglyLeu
LeuSerLeuTyrGluAspSerTyrLeuglyTrpLysglyGluAsnIleLeuAspGluAspLysAspPheThr
ThrLysCysLeuLysSerAspTrpGluAsnIleSerGluLysTrpLeuAspLysArgValLysHisAspLeu
AspLeuProLeuHisTrpArgValProArgIleGluAspArgTrpPheIleGluAspTyrGluGlnGluAsp
AsnMetAsnProThrLeuLeuLysLeuAspLysLeuAspPheAsnMetValGlnSerIleHisGlnLysGlu
IleglyGluLeuAspArgTrpTrpValThrThrglyLeuAspLysLeuAspPheAspArgAsnAsnLeuLeu
GlnSerTyrMetTrpSerCysAspIleAspSerAspProLysPheLysLeuAspArgGluThrIleValGlu
IleglySerValLeuThrValValAspAspglyTyrAspValTyrglySerIleAspGluLeuAspLeuTyr
ThrSerSerValGluArgTrpSerCysValGluIleAspLysLeuProAsnThrLeuLysLeuIlePheMet
SerMetPheAsnLysThrAsnGluValglyLeuArgValGlnHisGluArgglyTyrAsnSerIleProThr
PheIleLysAspTrpValGluGlnCysLysSerTyrGlnLysGluAspArgTrpPheHisglyglyHisThr
ProProLeuGluGluTyrSerLeuAsnglyLeuValSerIleglyPheProLeuLeuLeuIleThrglyTyr
ValAspIleAspGluAsnGluAspAspLeuAspLysValHisProLeuProAspLeuLeuHisTyrSerSer
LeuLeuSerArgLeuIleAsnAspIleglyThrSerProAspGluMetAspArgglyAspAsnLeuLysSer
IleHisCysTyrMetAsnGluThrglyAspSerGluGluValAspArgGluHisIleLysglyValIleGlu
GluAsnTrpLysIleLeuAsnGlnCysCysPheAspGlnSerGlnPheGlnGluProPheIleThrPheAsn
LeuAsnSerValArgglySerHisPhePheTyrGluPheglyAspglyPheglyValThrAspSerTrpThr
LysValAspMetLysSerValLeuIleAspProIleProLeuglyGluGlu
```

Figure 6A

```
FB299124.1|   ---------------------------------MALPVAHRYSSEAEELRE--  18
FB299123.1|   -----------------------------------MASSSPVPLVTQVQRK--  16
FB299125.1|   -----MWNCSLTISATAASPPLRQWPGG------------ISWRRPSRLQCSAATTRHDD  43
AF484125.1|   -----------------------------------MASAAVANYEEEIVRP--  16
AB438045.1|   MALPALFGSSLPSSIRHNQPSLFSFRHPRFCSSSSSASFSSQFILCASKTGDQEIVRR--  58
Santalene     ------MDSSTATAMTAP------FIDP-----------TDHVNLKTDT-DASENRR--  33
                                                                    *

FB299124.1|   -------------------ATTFHPSLWGDFFLTY-----QPPTAAQQAYMEERAEVLREDV  56
FB299123.1|   -----------------PQTFTPSPWGDFFLHH-----VPCTPSQFLSMKERAQRKKEEV  54
FB299125.1|   DLVLDNKGDNRLRENTGADIFQPSIWGDIFLGNSNPAAAASSQQQQIQMEERADKLREEV 103
AF484125.1|   -------------------VADFSPSLWGDQFLSFS------IDNQIAEKYAQEIEALKEQT  53
AB438045.1|   -----------------SANWQPSVWDYDYVQS----LTVDY--TEDKYTKQVQRLKEEV  95
Santalene     -----------------MGNYKPSIWNYDFLQS----LATHHNIVEERHLKLAEKLKGQV  72
                                  : ** *.  ::                 :  :  :.

FB299124.1|   RKILRD---STQLPETLNLILTLQRLGLDYYYENEIDKLLHRIYN---SDYNDKDLNLVS 110
FB299123.1|   RQIILENFASSNLVRKLELVDTLQRIGVDYHYKEEIDNLLHSIFDD--KDGGSDNLYITS 112
FB299125.1|   AKMIAS---STTTASRLQLIDALERLCLDHLFEEEIGAALAQIET---ADVSDYDLETVA 157
AF484125.1|   RSMLLAT--ARKLADTLNLIDTIERLGIAYHFEKEIDEILDQIYN---QNSTFDDLCTSA 108
AB438045.1|   KGLFDR---EMKQVAKLEFIDVVQRLGLGYHFKTEIKIALSSIHNNTEDAQLSNDLYAAS 152
Santalene     KFMFGA---PMEPLAKLELVDVVQRLGLNHLFETEIKEALFSIYKDGSNGWWFGHLHATS 129
                 ::         *:::  .::*: :  :: **   *  *          .*   :

FB299124.1|   LRFYLLRKNGYDVSSDVFLSFKTDEGGFAY---GDTISLLSLYNAAYLRRHGEKVLDEAI 167
FB299123.1|   LRFYLLRKHGYGVSSDVFEKFRDEQGNISS---DDISCLLMLYDAAHLRTHGEEILDNII 169
FB299125.1|   LWFCLLRKHRYMVSPDVFVRFKDEDGGFLV---NSPKDLLNLYNAAHMRTHGEIILEEAV 214
AF484125.1|   LQFRLLRQHGFNISPQIFSKFQDENGKFKESLASDVLGLLNLYEASHVRTHDNILEDAL 168
AB438045.1|   LRFRLLRQYGCNVQQDVFQRFMNKTGTFKESLNKDVKGILGLYEASFHGMEGETVLDEAW 212
Santalene     LRFRLLRQCGLFIPQDVFKTFQNKTGEFDMKLCDNVKGLLSLYEASYLGWKGENILDEAK 189
              * * ***:       :  ::*  * . *  :        .  :* **:*:.    . : :*::

FB299124.1|   SFTRRRLQD-ILELPASPFAKEVSASLHTPLFRRVGILEARNYIP-IYEKDATVNEAILE 225
FB299123.1|   TFNKSHLQSLLLENLEPELREEVQCTLETPRFRRVKRVEARRYIS-VYEKNTTRDATILE 228
FB299125.1|   LFSQRHLET-MVPYMEGSLAREIKSALDIPLPRRPRIYEYKYYIS-MYEKDGMVDEKVLQ 272
AF484125.1|   AFSTVHLES-AAPYMNSPLREQVTHALEQCLHKGVPRVETRFFISSIYEKEESKNDMLLR 227
AB438045.1|   NFASKHLKDLNLDEVPTNLASNVSHALDMPIHWRPNRLEARWFMD-MYEKQQDLIPSLLR 271
Santalene     AFTTKCLKSAWENISEKWLAKRVKHALALPLHWRVPRIEARWFIE-AYEQEANMNPTLLK 248
                *     *:     :     .:  :*       *  : ::  **::      :*.

FB299124.1|   LAKLNFNLQQLVFCEELKHCTMWWKEFLAKSKMTFVRDRIVEVYFWMNGACYHPPYSHSR 285
FB299123.1|   FAKLDYNILQAIYCDELKELTVWWKDFQSQTDLSFARDRMVELHFWMLGVVYEPYYPYSR 288
FB299125.1|   LAKLNSNIMQLHHQHELGIVSRWWNDINIESRLPHVRDRLVECYLWILGVYYEPCYSRAR 332
AF484125.1|   FAKLDFNLLQMLHKQELAEVSRWWKDLNFVTTLPYARDRVVECYFWALGVYFEPQYSQAR 287
AB438045.1|   LAKLDFNIVQSIHRKEVSNLARWWWVELGAN-KMTFFRDRLVESYFWSCILVFEPQYTDFR 330
Santalene     LAKLDFNMVQSIHQKEIGELARWWVTTGLD-KLAFARNNLLQSYMWSCAIASDPKFKLAR 307
              :*** *:  * . .*:    . **   :..  *:.::: ::*       .*   :   *

FB299124.1|   IIQTKITSFVTIIDDMFDTYGTTEECMKFVEAIGRWDESAVPLLPEYMKGFYLFLLDTFH 345
FB299123.1|   IMMTKFIVLASLLDDLYDSYSTTEESNAFIAAMQRWDDRTTEHLPACLKALFINIVKTTN 348
FB299125.1|   IILTMTTAMVTLLDDTYDSYATPEECELFTKCIESWDSMGAQDLPERMKYGLEKIFDSCE 392
AF484125.1|   VMLVKTISMISIVDDTFDAYGTVKELEAYTDAIQRWDINEIDRLPDYMKISYKAILDLYK 347
AB438045.1|   ELNTRIACMATLIDDVYDIYGTPEELELLTDFILRWDITDIDKLPPTIRNGFMALYNTTN 390
Santalene     ETIVEIGSVLTVVDDGYDVYGSIDELDLYTSSVERWSCVEIDKLPNTLKLIFMSMFNKTN 367
                    .    . :::**  :*  .*.: .*         :    **    :: :  .

FB299124.1|   SFEDELGPQ-KSYRVLYLKHAMERLVQQYYNEIKWRDEDYVPKTMSEHLQVSMESIACIP 404
FB299123.1|   EIEEELKLM-KNKHADLIKRLVIDTAKFYHAEVEWRDQHYIPTDIEEEHLQISTRSSVCMQ 407
FB299125.1|   IIENMLHQE-EKYRIWYLRQSIKDLVISYSVEVKMLQEGYIPKSVEEHLKLSLITVGYPI 451
AF484125.1|   DYEKELSSAGRSHIVCHAIERMKEVVRNYNVESTWFIEGYKPP-VSEYLSNALATTTYYY 406
AB438045.1|   KVGYRTMTKRGINPIPYLRKLWGDECKADMKEVHWFNNGIKPT-LKEYMDVAVDSIGGLI 449
Santalene     EVGLRVQHERGYNSIPTFIKAWVEQCKSYQKEARWFHGGHTPP-LEEYSLNGLVSIGFPL 426
                        *           *      :.*:  .  :
```

Figure 6B

```
FB299124.1|   ITCAAFVGMGDIITKETLEWILSFPQFLMSFGIYVRLSNDVASTMREQTKDHSASTVHCY 464
FB299123.1|   ITNLALISLGEVTTRKDVDWALTFPKIIRAACIVGRVGNDIVSHEREQTSEHVGSTVQTC 467
FB299125.1|   LACVSFVGMHDIATKDCLDWVSSIPKMVEALSVILRLVDDLESYEREQLVPHVASTIDSY 511
AF484125.1|   LATTSYLGMKSVAEQD-FEWLSKNPKILEASVIICRVIDDTATYEVEKSRGQIATGIECC 465
AB438045.1|   LLLNSYFLTTDYLTEEGLNYVSKIPSVMHSSAQIFRFNDDLSTSSHELARGDNSKALECY 509
Santalene     LLITGYVAIAEN--EAALDKVHPLPDLLHYSSLLSRLINDIGTSPDEMARGDNLKSIHCY 484
                :  .  .   . .:    *..:       *. :*   :  *     .  . :.

FB299124.1|   MKEHGTTMNDACEKIKELAEDKWKDMLEQCLALT--ELPKVIPRTVFDFARTIVNMYKND 522
FB299123.1|   MKQYGVTVEEANEKLRVIIEEAWMDIVEECLEQ---KRPMALLETAVNVARTMDFMYKRE 524
FB299125.1|   MKEHNVSIEVAREQIYILKEESWKDFNNEWLNPDNNVYPKQLLERMFNLARTAQFLYNKE 571
AF484125.1|   MRDYGVSTKEAMDKFQKMAETAWKDLNEGLLRPT--PISAEFLTPILNLARIVEVTYIHN 523
AB438045.1|   MNETGASEEIAREHIRHLVRETWKKMNKEVFEDYPFSGFGPFLSACLNLARASHCFYEYG 569
Santalene     MNETGASEEVAREHIKGVIEENWKILNQCCFDQSQFQ--EPFITFNLNSVRGSHFFYEFG 542
              *.: ..:  :  *  :::   :  . *  : :   :           :   .: .*    *

FB299124.1|   HDGFTS-SEALKEMIELLFVKPVPN---  546
FB299123.1|   -DAYTL-SFSLKDVIASMYVNSVRAC--  548
FB299125.1|   -EKFTN-SHYLKDTVHSLLLAEPFKIPI  597
AF484125.1|   LDGYTHPEKVLKPHIIDLLVESIQIA--  549
AB438045.1|   -DGYGLPDHQTRDHLASTIFESVSLD--  594
Santalene     -DGFGVTDSWTKVDMKSVLIDPIPLGEE  569
```

Figure 10A

Santalene synthase genes from *S. austrocaledonicum*, *S. spicatum* and *S. album*.

```
              ....|....| ....|....| ....|....| ....|....| ....|....| ....|....|
                  10         20         30         40         50         60

SauSSy ORF    ATGGATTCTT CCACCGCCAC CGCCATGACA GCTCCATTCA TTGATCCTAC TGATCATGTG

SspiSSy OR    ATGGATTCTT CCACCGCCAC CGCCACGACA GCTCCATTTA TTGATCATAC TGATCATGTG

SaSSy ORF     ATGGATTCTT CCACCGCCAC CGCCATGACA GCTCCATTCA TTGATCCTAC TGATCATGTG

....|....| ....|....| ....|....| ....|....| ....|....| ....|....|
                  70         80         90        100        110        120

SauSSy ORF    AATCTCAAAA CTGATACTGA TGCCTCAGAG AATCGAAGGA TGGGGAATTA TAAACCCAGC

SspiSSy OR    AATCTTAAAA TTGATAATGA TTCCTCCGAG AGTCGAAGGA TGGGCAATTA TAAACCCAGT

SaSSy ORF     AATCTCAAAA CTGATACGGA TGCCTCAGAG AATCGAAGGA TGGGAAATTA TAAACCCAGC

....|....| ....|....| ....|....| ....|....| ....|....| ....|....|
                 130        140        150        160        170        180

SauSSy ORF    ATTTGGAATT ATGATTTTTT ACAATCACTT GCAACTCATC ACAATATTGT GGAAGAGAGG

SspiSSy OR    ATTTGGAATT ATGATTTTCT GCAATCACTT GCAATCCATC ACAATATTGT GGAAGAGAAG

SaSSy ORF     ATTTGGAATT ATGATTTTTT ACAATCACTT GCAACTCATC ACAATATTGT GGAAGAGAGG

....|....| ....|....| ....|....| ....|....| ....|....| ....|....|
                 190        200        210        220        230        240

SauSSy ORF    CATCTAAAGC TAGCTGAGAA GCTGAAGGGC CAAGTGAAGT TTATGTTTGG GGCACCAATG

SspiSSy OR    CATCTAAAGC TAGCTGAGAA GCTGAAGGGC CAAGTGATGT CTATGTTTGG GGCACCAATG

SaSSy ORF     CATCTAAAGC TAGCTGAGAA GCTGAAGGGC CAAGTGAAGT TTATGTTTGG GGCACCAATG
```

Figure 10B

```
          ....|....| ....|....| ....|....| ....|....| ....|....| ....|....|
              250        260        270        280        290        300
SauSSy ORF  GAGCCGTTAG CAAAGCTGGA GCTTGTGGAT GTGGTTCAAA GGCTCGGGCT AAACCACCGA

SspiSSy OR  GAGCCGTTAG CAAAGCTGGA GCTTGTGGAT GTGGTTCAAA GGCTTGGGCT AAACCACCAA

SaSSy ORF   GAGCCGTTAG CAAAGCTGGA GCTTGTGGAT GTGGTTCAAA GGCTTGGGCT AAACCACCTA

....|....| ....|....| ....|....| ....|....| ....|....| ....|....|
              310        320        330        340        350        360
SauSSy ORF  TTTGAGACAG AGATCAAGGA AGCGCTATTT AGTATTTATA AGGACGAGAG CAATGGATGG

SspiSSy OR  TTTGAGACAG AGATCAAGGA AGCCCTATTT AGTGTTTACA AGGATGGGAG CAATGGATGG

SaSSy ORF   TTTGAGACAG AGATCAAGGA AGCGCTGTTT AGTATTTACA AGGATGGGAG CAATGGATGG

....|....| ....|....| ....|....| ....|....| ....|....| ....|....|
              370        380        390        400        410        420
SauSSy ORF  TGGTTTGGCC ACCTTCATGC GACATCTCTC CGATTTAGGC TGCTACGACA GTGTGGGCTT

SspiSSy OR  TGGTTTGGCC ACCTTCATGC AACATCTCTT CGATTTAGGC TACTACGACA GTGTGGGCTT

SaSSy ORF   TGGTTTGGCC ACCTTCATGC GACATCTCTC CGATTTAGGC TGCTACGACA GTGTGGGCTT

....|....| ....|....| ....|....| ....|....| ....|....| ....|....|
              430        440        450        460        470        480
SauSSy ORF  TTTATCCCCC AGGATGTGTT TAAAACGTTC CAAAACAAAA CTGGTGAATT TGATATGAAA

SspiSSy OR  TTTATCCCCC AGGATGTGTT TAAAACGTTC CAGAGCAAAA CTGATGAATT TGATATGAAA

SaSSy ORF   TTTATTCCCC AAGATGTGTT TAAAACGTTC CAAAACAAGA CTGGGGAATT TGATATGAAA

....|....| ....|....| ....|....| ....|....| ....|....| ....|....|
              490        500        510        520        530        540
SauSSy ORF  CTGTGTGACA ACGTAAAAGG GCTGCTGAGC TTATATGAAG CTTCATACTT GGGATGGAAG
```

Figure 10C

```
SspiSSy OR    CTGTGTGACA ACATAAAAGG GTTGTTGAGC TTGTATGAAG CTTCATTCCT GGGGTGGAAG SaSSy ORF     CTTTGTGACA ACGTAAAAGG GCTGCTGAGC TTATATGAAG CTTCATACTT GGGATGGAAG ....|....| ....|....| ....|....| ....|....| ....|....| ....|....|
                  550        560        570        580        590        600

SauSSy ORF    GGTGAAAACA TCCTAGATGA AGCCAAGGCC TTCGCCACCA AGTACTTGAA AAGTGCATGG

SspiSSy OR    GGTGAAAACA TCCTAGATGA AGCCAAGGCC TTCGCCACCA AGTACTTGAA AAATGCATGG

SaSSy ORF     GGTGAAAACA TCCTAGATGA AGCCAAGGCC TTCACCACCA AGTGCTTGAA AAGTGCATGG

....|....| ....|....| ....|....| ....|....| ....|....| ....|....|
                  610        620        630        640        650        660

SauSSy ORF    GAAAATATAT CTGAAAAGTG GTTAGCCAAA AGAGTGAAGC ATGCATTGGC TTTACCTTTG

SspiSSy OR    GAAAATATAT CCCAAAAGTG GCTAGCCAAA AGAGTGAAGC ATGCACTGGC TTTGCCTCTG

SaSSy ORF     GAAAATATAT CCGAAAAGTG GTTAGCCAAA AGAGTGAAGC ATGCATTGGC TTTGCCTTTG

....|....| ....|....| ....|....| ....|....| ....|....| ....|....|
                  670        680        690        700        710        720

SauSSy ORF    CATTGGAGAG TCCCTCGAAT CGAAGCTAGA TGGTTCATTG AGGCATATGA GCAAGAAGCG

SspiSSy OR    CACTGGAGAG TCCCTCGAAT CGAGGCTAGA TGGTTCATTG AGGCATATGA GCAAGAAGAG

SaSSy ORF     CATTGGAGAG TCCCTCGAAT CGAAGCTAGA TGGTTCATTG AGGCATATGA GCAAGAAGCG

....|....| ....|....| ....|....| ....|....| ....|....| ....|....|
                  730        740        750        760·       770        780

SauSSy ORF    AATATGAACC CAACACTACT CAAACTCGCA AAATTAGACT TTAATATGGT GCAATCAATT

SspiSSy OR    AACATGAACC CAACACTACT CAAACTTGCA AAATTAGACT TTAACATGGT GCAATCAATT

SaSSy ORF     AATATGAACC CAACACTACT CAAACTCGCA AAATTAGACT TTAATATGGT GCAATCAATT
```

Figure 10D

```
         ....|....| ....|....| ....|....| ....|....| ....|....| ....|....|
             790        800        810        820        830        840
SauSSy ORF   CATCAGAAAG AGATTGGGGA ATTAGCAAGG TGGTGGGTGA CTACTGGCTT GGATAAGTTA

SspiSSy OR   CATCAGAAAG AGATTGGGGA ATTAGCAAGG TGGTGGGTGA CTACTGGCTT GGATAAGTTA

SaSSy ORF    CATCAGAAAG AGATTGGGGA ATTAGCAAGG TGGTGGGTGA CTACTGGCTT GGATAAGTTA

....|....| ....|....| ....|....| ....|....| ....|....| ....|....|
             850        860        870        880        890        900
SauSSy ORF   GCCTTTGCTA GGAATAATTT ACTGCAAAGC TATATGTGGA GCTGCGCGAT TGCTTCCGAC

SspiSSy OR   GCCTTTGCTA GGAATAATTT ACTGCAAAGC TATATGTGGA GCTGCGCGAT TGCTTCCGAC

SaSSy ORF    GCCTTTGCCA GGAATAATTT ACTGCAGAGC TATATGTGGA GCTGCGCGAT TGCTTCCGAC

....|....| ....|....| ....|....| ....|....| ....|....| ....|....|
             910        920        930        940        950        960
SauSSy ORF   CCGAAGTTCA AACTTGCTAG AGAAACTATT GTCGAAATCG AAGTGTACT CACAGTTGTT

SspiSSy OR   CCAAAGTTCA AACTTGCTAG AGAAACTATT GTCGAAATCG AAGTGTACT CACAGTTGTG

SaSSy ORF    CCGAAGTTCA AACTTGCTAG AGAAACTATT GTCGAAATCG AAGTGTACT CACAGTTGTT

....|....| ....|....| ....|....| ....|....| ....|....| ....|....|
             970        980        990       1000       1010       1020
SauSSy ORF   GATGATGCAT ATGACGTCTA TGGTTCAATG GACGAACTTG ATCTCTACAC AAGCTCCGTT

SspiSSy OR   GACGATGCAT ATGATGTCTA TGGTTCAATG GATGAACTTG ATCACTACAC ATACTCCGTT

SaSSy ORF    GACGATGGAT ATGACGTCTA TGGTTCAATC GACGAACTTG ATCTCTACAC AAGCTCCGTT
```

Figure 10E

```
            ....|....| ....|....| ....|....| ....|....| ....|....| ....|....|
                1030       1040       1050       1060       1070       1080
SauSSy ORF  GAAAGGTGGA GCTGTGTAGA AATTGACAAG TTGCCAAACA CGTTAAAATT GATTTTTATG

SspiSSy OR  GAAAGGTGGA GCTGTGTAGA AATTGACAAG CTGCCAAACA CGTTAAAATT GATTTTTATG

SaSSy ORF   GAAAGGTGGA GCTGTGTGGA AATTGACAAG TTGCCAAACA CGTTAAAATT AATTTTTATG

....|....| ....|....| ....|....| ....|....| ....|....| ....|....|
                1090       1100       1110       1120       1130       1140
SauSSy ORF  TCTATGTTTA ATAAGACCAA TGAGGTTGGC CTTCGAGTCC AGCATGAGCG AGGCTACAAT

SspiSSy OR  TCTATGTTCA ACAAGACCAA TGAGGTTGGC CTTCGAGTCC AGCATGAGCG AGGCTACAAC

SaSSy ORF   TCTATGTTCA ACAAGACCAA TGAGGTTGGC CTTCGAGTCC AGCATGAGCG AGGCTACAAT

....|....| ....|....| ....|....| ....|....| ....|....| ....|....|
                1150       1160       1170       1180       1190       1200
SauSSy ORF  AGCATCCCTA CTTTTATCAA AGCGTGGGTT CAACAGTGTA AATCATACCA GAAAGAAGCA

SspiSSy OR  GGCATCCCTA CTTTTATCAA AGCATGGGTT GAACAGTGTA AAGCATACCA GAAAGAGGCA

SaSSy ORF   AGCATCCCTA CTTTTATCAA AGCGTGGGTT GAACAGTGTA AATCATACCA GAAAGAAGCA

....|....| ....|....| ....|....| ....|....| ....|....| ....|....|
                1210       1220       1230       1240       1250       1260
SauSSy ORF  AGATGGTTCC ACGGGGACA CACGCCTCCG TTGGAAGAAT ATAGCTTGAA TGGACTTGTT

SspiSSy OR  AGATGGTACC ATGGGGGACA CACGCCTCCA TTGGAGGAAT ATAGCTTGAA TGGACTTGTT

SaSSy ORF   AGATGGTTCC ACGGGGGACA CACGCCTCCA TTGGAAGAAT ATAGCTTGAA TGGACTTGTT
```

Figure 10F

```
              ....|....| ....|....| ....|....| ....|....| ....|....| ....|....|
                  1270       1280       1290       1300       1310       1320
SauSSy ORF    TCCATAGGAT TCCCTCTCTT GTTGATCACC GGCTACGTGG CAATCGCTGA GAACGAGGCT

SspiSSy OR    TCCATAGGAT TCCCTCTCTT GTTGATCACC GGCTACATCG CAATCGCTGA GAACGAGGCT

SaSSy ORF     TCCATAGGAT TCCCTCTCTT GTTAATCACG GGCTACGTGG CAATCGCTGA GAACGAGGCT

....|....| ....|....| ....|....| ....|....| ....|....| ....|....|
                  1330       1340       1350       1360       1370       1380
SauSSy ORF    GCACTGGATA AAGTGCACCC CCTTCCTGAT CTTCTGCACT ACTCCTCCCT CCTTAGTCGC

SspiSSy OR    GCACTGGATA AAGTGCACCC CCTTCCTGAT CTTCTGCACT ACTCCTCCCT CCTTAGTCGC

SaSSy ORF     GCACTGGATA AAGTGCACCC CCTTCCTGAT CTTCTGCACT ACTCCTCCCT CCTTAGTCGC

....|....| ....|....| ....|....| ....|....| ....|....| ....|....|
                  1390       1400       1410       1420       1430       1440
SauSSy ORF    CTCATCAATG ATATAGGAAC GTCTCCGGAT GAGATGGCAA GAGGCGATAA TCTGAAGTCA

SspiSSy OR    CTCATCAATG ACATGGGAAC GTCTCCGGAC GAGATGGCAA GAGGTGACAA TCTGAAGTCA

SaSSy ORF     CTCATCAATG ATATAGGAAC GTCTCCGGAT GAGATGGCAA GAGGCGATAA TCTGAAGTCA

....|....| ....|....| ....|....| ....|....| ....|....| ....|....|
                  1450       1460       1470       1480       1490       1500
SauSSy ORF    ATCCATTGTT ACATGAACGG AACTGGGGCT TCCGAGGAAG TTGCTCGTGA GCACATAAAG

SspiSSy OR    ATCCACTGTT ACATGAACGA AACTGGGGCT TCTGAGGAAG TTGCTCGTGA GCACATAAAA

SaSSy ORF     ATCCATTGTT ACATGAACGA AACTGGGGCT TCCGAGGAAG TTGCTCGTGA GCACATAAAG
```

Figure 10G

```
           ....|....| ....|....| ....|....| ....|....| ....|....| ....|....|
              1510       1520       1530       1540       1550       1560
SauSSy ORF GGAGTAATCG AGGAGAATTG GAAAATACTG AATCAGTGCT GCTTTGATCA ATCTCAGTTT

SspiSSy OR GGAATAATCG AGGAGAATTG GAAAATACTG AATCAGTGCT GCTTTGATCA ATCTCAGTTT

SaSSy ORF  GGAGTAATCG AGGAGAATTG GAAAATACTG AATCAGTGCT GCTTTGATCA ATCTCAGTTT

....|....| ....|....| ....|....| ....|....| ....|....| ....|....|
              1570       1580       1590       1600       1610       1620
SauSSy ORF CAGGAGCCTT TTATAACCTT CAATTTGAAC TCTGTTCGAG GGTCTCATTT CTTCTATGAA

SspiSSy OR CAGGAGCCTT TTATAACCTT CAATTTGAAC TCTGTTCGAG GGTCTCATTT CTTCTATGAA

SaSSy ORF  CAGGAGCCTT TTATAACCTT CAATTTGAAC TCTGTTCGAG GGTCTCATTT CTTCTATGAA

....|....| ....|....| ....|....| ....|....| ....|....| ....|....|
              1630       1640       1650       1660       1670       1680
SauSSy ORF TTTGGGGATG GCTTTGGGGT GACGGATAGC TGGACAAAGG TTGATATGAA GTCCGTTTTG

SspiSSy OR TTTGGGGATG GCTTTGGGGT GACAGATAGC TGGACAAAGG TTGATATGAA GTCTGTTTTG

SaSSy ORF  TTTGGGGATG GCTTTGGGGT GACGGATAGC TGGACAAAGG TTGATATGAA GTCCGTTTTG

....|....| ....|....| ....|....| ...
              1690       1700       1710
SauSSy ORF ATTGACCCTA TTCCTCTCGG CGAGGAGTAG TAA

SspiSSy OR ATCGACCCTA TTCCTCTCGG CGAGGAGTAG TAA

SaSSy ORF  ATCGACCCTA TTCCTCTCGG CGAGGAGTAG TAA
```

Figure 11A

Santalene synthase amino acid sequences of *S. austrocaledonicum*, *S. spicatum* and *S. album*.

```
            ....|....| ....|....| ....|....| ....|....| ....|....| ....|....|
                10         20         30         40         50         60
SauSSy ORF  MDSSTATAMT APFIDPTDHV NLKTDTDASE NRRMGNYKPS IWNYDFLQSL ATHHNIVEER

SspiSSy OR  MDSSTATATT APFIDHTDHV NLKIDNDSSE SRRMGNYKPS IWNYDFLQSL AIHHNIVEEK

SaSSy ORF   MDSSTATAMT APFIDPTDHV NLKTDTDASE NRRMGNYKPS IWNYDFLQSL ATHHNIVEER

....|....| ....|....| ....|....| ....|....| ....|....| ....|....|
                70         80         90        100        110        120
SauSSy ORF  HLKLAEKLKG QVKFMFGAPM EPLAKLELVD VVQRLGLNHR FETEIKEALF SIYKDESNGW

SspiSSy OR  HLKLAEKLKG QVMSMFGAPM EPLAKLELVD VVQRLGLNHQ FETEIKEALF SVYKDGSNGW

SaSSy ORF   HLKLAEKLKG QVKFMFGAPM EPLAKLELVD VVQRLGLNHL FETEIKEALF SIYKDGSNGW

....|....| ....|....| ....|....| ....|....| ....|....| ....|....|
               130        140        150        160        170        180
SauSSy ORF  WFGHLHATSL RFRLLRQCGL FIPQDVFKTF QNKTGEFDMK LCDNVKGLLS LYEASYLGWK

SspiSSy OR  WFGHLHATSL RFRLLRQCGL FIPQDVFKTF QSKTDEFDMK LCDNIKGLLS LYEASFLGWK

SaSSy ORF   WFGHLHATSL RFRLLRQCGL FIPQDVFKTF QNKTGEFDMK LCDNVKGLLS LYEASYLGWK

....|....| ....|....| ....|....| ....|....| ....|....| ....|....|
               190        200        210        220        230        240
SauSSy ORF  GENILDEAKA FATKYLKSAW ENISEKWLAK RVKHALALPL HWRVPRIEAR WFIEAYEQEA

SspiSSy OR  GENILDEAKA FATKYLKNAW ENISQKWLAK RVKHALALPL HWRVPRIEAR WFIEAYEQEE

SaSSy ORF   GENILDEAKA FTTKCLKSAW ENISEKWLAK RVKHALALPL HWRVPRIEAR WFIEAYEQEA
```

Figure 11B

```
             ....|....| ....|....| ....|....| ....|....| ....|....| ....|....|
                 250        260        270        280        290        300
SauSSy ORF   NMNPTLLKLA KLDFNMVQSI HQKEIGELAR WWVTTGLDKL AFARNNLLQS YMWSCAIASD
SspiSSy OR   NMNPTLLKLA KLDFNMVQSI HQKEIGELAR WWVTTGLDKL AFARNNLLQS YMWSCAIASD
SaSSy ORF    NMNPTLLKLA KLDFNMVQSI HQKEIGELAR WWVTTGLDKL AFARNNLLQS YMWSCAIASD ....|....| ....|....| ....|....| ....|....| ....|....| ....|....|
                 310        320        330        340        350        360
SauSSy ORF   PKFKLARETI VEIGSVLTVV DDAYDVYGSM DELDLYTSSV ERWSCVEIDK LPNTLKLIFM
SspiSSy OR   PKFKLARETI VEIGSVLTVV DDAYDVYGSM DELDHYTYSV ERWSCVEIDK LPNTLKLIFM
SaSSy ORF    PKFKLARETI VEIGSVLTVV DDGYDVYGSI DELDLYTSSV ERWSCVEIDK LPNTLKLIFM ....|....| ....|....| ....|....| ....|....| ....|....| ....|....|
                 370        380        390        400        410        420
SauSSy ORF   SMFNKTNEVG LRVQHERGYN SIPTFIKAWV QQCKSYQKEA RWFHGGHTPP LEEYSLNGLV
SspiSSy OR   SMFNKTNEVG LRVQHERGYN GIPTFIKAWV EQCKAYQKEA RWYHGGHTPP LEEYSLNGLV
SaSSy ORF    SMFNKTNEVG LRVQHERGYN SIPTFIKAWV EQCKSYQKEA RWFHGGHTPP LEEYSLNGLV ....|....| ....|....| ....|....| ....|....| ....|....| ....|....|
                 430        440        450        460        470        480
SauSSy ORF   SIGFPLLLIT GYVAIAENEA ALDKVHPLPD LLHYSSLLSR LINDIGTSPD EMARGDNLKS
SspiSSy OR   SIGFPLLLIT GYIAIAENEA ALDKVHPLPD LLHYSSLLSR LINDMGTSPD EMARGDNLKS
SaSSy ORF    SIGFPLLLIT GYVAIAENEA ALDKVHPLPD LLHYSSLLSR LINDIGTSPD EMARGDNLKS
```

SauSSy ORF   IHCYMNGTGA SEEVAREHIK GVIEENWKIL NQCCFDQSQF QEPFITFNLN SVRGSHFFYE

SspiSSy OR   IHCYMNETGA SEEVAREHIK GIIEENWKIL NQCCFDQSQF QEPFITFNLN SVRGSHFFYE

SaSSy ORF    IHCYMNETGA SEEVAREHIK GVIEENWKIL NQCCFDQSQF QEPFITFNLN SVRGSHFFYE

....|....| ....|....| ....|....| .
                 550        560        570

SauSSy ORF   FGDGFGVTDS WTKVDMKSVL IDPIPLGEE* *

SspiSSy OR   FGDGFGVTDS WTKVDMKSVL IDPIPLGEE* *

SaSSy ORF    FGDGFGVTDS WTKVDMKSVL IDPIPLGEE* *
```

Figure 12A

CLUSTAL 2.0.12 multiple sequence alignment

```
1SaSSy          ------------------------MDSSTATAMTAPF--IDPTDHVNLKTDTDASENRRMG  35

2SauSSy         ------------------------MDSSTATAMTAPF--IDPTDHVNLKTDTDASENRRMG  35

3SspiSSy        ------------------------MDSSTATATTAPF--IDHTDHVNLKIDNDSSESRRMG  35

4SaMono         -----------------------MDAFATSPTSALIKAVNCIAHVTPMAGEDSSENRPAS  37

27DQ785793.1    MSSLIMQVVIPKPAKFFHNNLFSLSSKKHRFSTTTTTRGGFWAFCSLQTGNEIQTERRTG  60

28DQ785794.1    ----------MPLNSLHN-LERKPSK--AWSTSCTAPAARLQASFSLQQEEPRQIRRSG  46
                                                  :         ::              :   ^*  ,

1SaSSy          NYKPSIWNYDFLQSLATHHNIVEERHLKLAEKLKGQVKFMFGAPMEPLAKLELVDVVQRL  95

2SauSSy         NYKPSIWNYDFLQSLATHHNIVEERHLKLAEKLKGQVKFMFGAPMEPLAKLELVDVVQRL  95

3SspiSSy        NYKPSIWNYDFLQSLAIHHNIVEEKHLKLAEKLKGQVMSMFGAPMEPLAKLELVDVVQRL  95

4SaMono         NYKPSTWDYEFLQSLATSHNTVQEKHMKMAEKLKEEVKSMIKGQMEPVAKLELINILQRL  97

27DQ785793.1    GYQPTLWDFSTIQSFDSEYK--EEKHLMRAAGMIDQVKMMLQEEVDSIRRLELIDDLRRL 118

28DQ785794.1    DYQPSLWDFNYIQSLNTPYK--EQRYVNRQAELIMQVFMLLKVKMEAIQQLELIDDLQYL 104
                 .*:*: *::. :*^*:  ::  :::::       :    :*   ::  ::   :*^*:: :: *

1SaSSy          GLNHLFETEIKEALFSIYKDGSNGWWFGHLHATSLRFRLLRQCGLFIPQDVFKTFQ-NKT 154

2SauSSy         GLNHRFETEIKEALFSIYKDESNGWWFGHLHATSLRFRLLRQCGLFIPQDVFKTFQ-NKT 154

3SspiSSy        GLNHQFETEIKEALFSVYKDGSNGWWFGHLHATSLRFRLLRQCGLFIPQDVFKTFQ-SKT 154

4SaMono         GLKYRFESEIKEELFSLYKDGTDAWWVDNLHATALRFRLLRENGIFVPQDVFETLK-DKS 156

27DQ785793.1    GISCHFEREIVEILNSKYYTNN-EIDERDLYSTALRFRLLRQYDFSVSQEVFDCFKNAKG 177

28DQ785794.1    GLSYFFFDEIKQILSSIHNEHR-YFHNNDLYLTALGFRILRQHGFNVSEDVFDCFKTEKC 163
                *:.  *  *^ * : * *  :           .*: *:* **:**: .: *..::**.  ::  *
```

Figure 12B

```
1SaSSy         GEFDMKLCDNVKGLLSLYEASYLGWKGENILDEAKAFTTKCLKSAWENISEK---WLAKR 211

2SauSSy        GEFDMKLCDNVKGLLSLYEASYLGWKGENILDEAKAFATKYLKSAWENISEK---WLAKR 211

3SspiSSy       DEFDMKLCDNIKGLLSLYEASFLGWKGENILDEAKAFATKYLKNAWENISQK---WLAKR 211

4SaMono        GKFKSQLCKDVRGLLSLYEASYLGWEGEDLLDEAKKFSTTNLNNVKESISSN---TLGRL 213

27DQ785793.1   TDFKPSLVDDTRGLLQLYEASFLSAQGEETLRLARDFATKFLQKRVLVDKD---INLLSS 234

28DQ785794.1   SDFNANLAQDTKGMLQLYEASFLLREGEDTLELARRFSTRSLREKLDEDGDEIDEDLSSW 223

*.  .*  .: :*:*.*****:*   :**:   *   *: *:*   *..            *

1SaSSy         VKHALALPLHWRVPRIEARWFIEAYEQEANMNPTLLKLAKLDFNMVQSIHQKEIGELARW 271

2SauSSy        VKHALALPLHWRVPRIEARWFIEAYEQEANMNPTLLKLAKLDFNMVQSIHQKEIGELARW 271

3SspiSSy       VKHALALPLHWRVPRIEARWFIEAYEQEENMNPTLLKLAKLDFNMVQSIHQKEIGELARW 271

4SaMono        VKHALNLPLHWSAARYEARWFIDEYEKEENVNPNLLKYAKLDFNIVQSIHQQELGNLARW 273

27DQ785793.1   IERALELPTHWRVQMPNARSFIDAYKRRPDMNPTVLELAKLDFNMVQAQFQQELKEASRW 294

28DQ785794.1   IRHSLDLPLHWRIQGLEARWFLDAYARRFDMNPLIFKLAKLNFNIVQATYQEELKDVSRW 283

:..::*  **  **      :**  *::  *   :. ::**  :::  ***:* *:*:* .*:*:  :  :**

1SaSSy         WVTTGL-DKLAFARNNLLQSYMWSCAIASDPKFKLARETIVEIGSVLTVVDDGYDVYGSI 330

2SauSSy        WVTTGL-DKLAFARNNLLQSYMWSCAIASDPKFKLARETIVEIGSVLTVVDDAYDVYGSM 330

3SspiSSy       WVTTGL-DKLAFARNNLLQSYMWSCAIASDPKFKLARETIVEIGSVLTVVDDAYDVYGSM 330

4SaMono        WVETGL-DKLSFVRNTLMQNFMWGCAMVFEPQYGKVRDAAVKQASLIAMVDDVYDVYGSL 332

27DQ785793.1   WNSTGLVHELPFVRDRIVECYYWTTGVVERRQHGYERIMLTKINALVTTIDDVFDIYGTL 354

28DQ785794.1   WNSSCLAEKLPFVRDRIVECFFWAIGAFEPHQYSYQRKMAAIIITFVTIIDDVYDVYGTL 343

```
1SaSSy        DELDLYTSSVERWSCVEIDKLPNTLKLIFMSMFNKTNEVGLRVQHERGYNSIPTFIKAWV 390

2SauSSy       DELDLYTSSVERWSCVEIDKLPNTLKLIFMSMFNKTNEVGLRVQHERGYNSIPTFIKAWV 390

3SspiSSy      DELDHYTYSVERWSCVEIDKLPNTLKLIFMSMFNKTNEVGLRVQHERGYNGIPTFIKAWV 390

4SaMono       EELEIFTDIVDRWDITGIDKLPRNISMILLTMFNTANQIGYDLLRDRGFNGIPHIAQAWA 392

27DQ785793.1  EELQLFTTAIQRWDIESMKQLPPYMQICYLALFNFVNEMAYDTLRDKGFDSTPYLRKVWV 414

28DQ785794.1  EELELFTDMIRRWDNISISQLPYYMQVCYLALYNFVSERAYDILKDQHFNSIPYLQRSWV 403

:**: :*   : **.    :.:**  :.:  ::::*  ..:  .    ::: ::. * : : *.

1SaSSy        EQCKSYQKEARWFHGGHTPPLEEYSLNGLVSIGFPLLLITGYVAIAENE----AALDKVH 446

2SauSSy       QQCKSYQKEARWFHGGHTPPLEEYSLNGLVSIGFPLLLITGYVAIAENE----AALDKVH 446

3SspiSSy      EQCKAYQKEARWYHGGHTPPLEEYSLNGLVSIGFPLLLITGYIAIAENE----AALDKVH 446

4SaMono       TLCKKYLKEAKWYHSGYKPTLEEYLENGLVSISFVLSLVTAYLQTEILENLTYESAAYVN 452

27DQ785793.1  GLIESYLIEAKWYYKGHKPSLEEYMKNSWISIGGIPILSHLFFRLTDSI--EEEAAESMH 472

28DQ785794.1  SLVEGYLKEAYWYYNGYKPSLEEYLNNAKISISAPTIISQLYFTLANST--DETVIESLY 461

: *  **  *::  *:.*.****  *. :**.       :   :.            :

1SaSSy        PLPDLLHYSSLLSRLINDIGTSPDEMARGDNLKSIHCYMNETGASEEVAREHIKGVIEEN 506

2SauSSy       PLPDLLHYSSLLSRLINDIGTSPDEMARGDNLKSIHCYMNGTGASEEVAREHIKGVIEEN 506

3SspiSSy      PLPDLLHYSSLLSRLINDMGTSPDEMARGDNLKSIHCYMNETGASEEVAREHIKGIIEEN 506

4SaMono       SVPPLVRYSGLLNRLYNDLGTSSAEIARGDTLKSIQCYMTQGATEEAAREHIKGLVHEA 512

27DQ785793.1  KYHDIVRASCTILRLADDMGTSLDEVERGDVPKSVQCYMNEKNASEEEAREHVRSLIDQT 532

28DQ785794.1  EYHNILYLSGTILRLADDLGTSQHELERGDVPKAIQCYMKDTNASEREAVEHVKFLIRET 521

```
1SaSSy              WKILNQCCFDQS-QFQEPFITFNLNSVRGSHFFYEF-GDGFGVTDSWTKVDMKSVLIDPI 564

2SauSSy             WKILNQCCFDQS-QFQEPFITFNLNSVRGSHFFYEF-GDGFGVTDSWTKVDMKSVLIDPI 564

3SspiSSy            WKILNQCCFDQS-QFQEPFITFNLNSVRGSHFFYEF-GDGFGVTDSWTKVDMKSVLIDPI 564

4SaMono             WKGMNKCLFEQT-PFAEPFVGFNVNTVRGSQFFYQH-GDGYAVTESWTKDLSLSVLIHPI 570

27DQ785793.1        WKMMNKEMMTS--SFSKYFVEVSANLARMAQWIYQHESDGFGMQHSLVNKMLRDLLFHRY 590

28DQ785794.1        WKEMNTVTTASDCPFTDDLVAVATNLARAAQFIYLD-GDGHGVQHSEIHQQMGGLLFQPY 580

** :*         .  * . ::  .  * ,* ::::*  .**..: ,*  :    .:*:.

1SaSSy              PLGEE- 569

2SauSSy             PLGEE- 569

3SspiSSy            PLGEE- 569

4SaMono             PLNEED 576

27DQ785793.1        E----- 591

28DQ785794.1        V----- 581
```

TERPENE SYNTHASES FROM *SANTALUM*

RELATED APPLICATIONS

This application is a continuation of U.S. patent application Ser. No. 13/998,045, now allowed, filed Sep. 24, 2013, which is a continuation of U.S. patent application Ser. No. 13/261,101, now U.S. Pat. No. 8,569,025, filed Apr. 18, 2012, which is the National Stage of International Application No. PCT/AU2010/000802, filed Jun. 25, 2010, which claims benefit of priority to AU2009903016, filed Jun. 29, 2009. The subject matter of each of the above-referenced applications is incorporated by reference in its entirety herein.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file was created on Jan. 30, 2015, is 33 kilobytes in size, and titled 206CseqUS1.txt.

FIELD OF THE INVENTION

The present invention relates to a novel terpene synthase. The invention further relates to nucleic acids encoding a terpene synthase, to methods for preparing variant terpene synthases, and to host-organisms expressing the polypeptides of the invention. The present invention further comprises methods for making a terpene synthase and methods for making terpenoids such as terpenes.

BACKGROUND

The following discussion of the background art is intended to facilitate an understanding of the present invention only. The discussion is not an acknowledgement or admission that any of the material referred to is or was part of the common general knowledge as at the priority date of the application.

Sandalwood, *Santalum album* (Santalaceae) is a small hemi-parasitic tropical tree of great economic value found growing in southern India, Sri Lanka, eastern Indonesia and northern Australia. The timber is highly sought after for its fine grain, high density and excellent carving properties. Sandalwood timber contains resins and essential oils, particularly the santalols, santalenes and dozens of other minor sesquiterpenoids. These chemicals provide the unique sandalwood fragrance. The fragrant wood is usually ground and steam distilled, with the essential oil serving as a fixative for many high-end perfumes.

Centuries of over-exploitation has led to the demise of sandalwood in natural stands. Large plantations are being established throughout northern Australia to satisfy demand and conserve remaining reserves. *Santalum album* heartwood contains up to 6% dry wt. sesquiterpene oils, predominantly α- and β-santalol, α-trans-bergamotol and epi-β-santalol, along with the sesquiterpene olefins α- and β-santalene, α-bergamotene and epi-β-santalene, β-bisabolene, α-, β- and γ-curcumene. The amount of heartwood oil produced in a tree varies considerably, even under near-identical growing conditions. Causes of this yield variation are not well understood, but it is likely to be the result of both genetic and environmental factors.

Little is known about the biosynthesis of sesquiterpenoids such as sesquiterpenes in *S. album* or how essential oil production is regulated.

The present invention addresses a need in the art for methods of producing terpenes similar to those produced by sandalwood.

SUMMARY

In one embodiment, the present invention provides an isolated nucleic acid molecule that encodes a terpene synthase and is selected from among:

(a) a nucleic acid molecule comprising the sequence of nucleotides set forth in SEQ ID NO: 1, SEQ ID NO: 3 or SEQ ID NO: 5;

(b) a nucleic acid molecule that is a fragment of (a);

(c) a nucleic acid molecule comprising a sequence of nucleotides that is complementary to (a) or (b); and (d) a nucleic acid molecule that encodes a terpene synthase having at least or at least about 60%, 65%, 70%, 75%, 80%, 85%, 90%, 95%, 96%, 97%, 98%, 99% identity to any one of (a)-(c);

wherein the nucleic acid molecule encodes a terpene synthase.

Other embodiments include: a polypeptide encoded by a nucleic acid of the invention; a host cell comprising a nucleic acid of the invention; a non-human organism modified to harbor a nucleic acid of the invention; and methods of producing a polypeptide comprising culturing host cells of the invention.

In one embodiment, the invention provides a method of making at least one terpene synthase comprising culturing a host cell modified to contain at least one nucleic acid sequence under conditions conducive to the production of said at least one terpene synthase.

The invention further provides an isolated terpene synthase, wherein the terpene synthase is a *Santalum* terpene synthase; and the terpene synthase catalyzes the production of a santalene.

In another embodiment, the invention provides an isolated terpene synthase, comprising:

(a) the sequence of amino acids set forth in SEQ ID NO: 2, SEQ ID NO: 4 or SEQ ID NO: 6;

(b) the sequence of amino acids encoded by the nucleic acid molecule of any of claims 1 to 5;

(c) a sequence of amino acids that is at least or at least about 60%, 65%, 70%, 75%, 80%, 85%, 90%, 95% or more identical to the sequence of amino acids set forth in SEQ ID NO:2; or (d) a fragment of (a), (b) or (c);

wherein the terpene synthase catalyzes the production of a terpene.

The invention further provides a terpene synthase, wherein the terpene synthase catalyzes the production of α-santalene, α-trans-bergamotene, epi-β-santalene and β-santalene concurrently.

The invention also provides methods for detecting the presence of a terpene synthase polypeptide or nucleic acid in a sample.

In a further embodiment, the invention provides a method of producing a terpene synthase, the method comprising the steps of:

(a) selecting a host organism and/or cell which does not express a nucleic acid molecule having a sequence set forth in SEQ ID NO: 1, SEQ ID NO: 3 or SEQ ID NO: 5;

(b) transforming the organism with a nucleic acid molecule having a sequence set forth in SEQ ID NO: 1, SEQ ID NO: 3 or SEQ ID NO: 5; and (c) culturing the organism under conditions conducive to the production of the terpene synthase encoded by said nucleic acid.

In an alternative embodiment, the invention provides a method of producing a terpene synthase, the method comprising the steps of:

(a) selecting a host organism and/or cell which does express a nucleic acid molecule having a sequence set forth in SEQ ID NO: 1, SEQ ID NO: 3 or SEQ ID NO: 5;

(b) transforming the organism with a nucleic acid molecule having a sequence set forth in SEQ ID NO: 1, SEQ ID NO: 3 or SEQ ID NO: 5 in higher quantity; and (c) culturing the organism under conditions conducive to the production of the terpene synthase encoded by said nucleic acid.

The invention further provides a method of making a terpene, comprising:

(a) contacting an acyclic pyrophosphate terpene precursor with the terpene synthase of the invention, and, (b) optionally, isolating the terpene produced in step (a).

Preferably the method is performed on a terpene synthase that is heterologously expressed in a cell; wherein the acyclic pyrophosphate terpene precursor is expressed in the same cell as the terpene synthase; and wherein the step of contacting the acyclic pyrophosphate terpene precursor occurs in the cell. More preferably, the at least one terpene is selected from among (+)-epi-β-santalene, (+β-santalene, (+)-β-santalene, (+)-α-santalene, (−)-α-santalene, cis-α-bergamotene, trans-α-bergamotene, trans-β-bergamotene and cis-β-bergamotene.

The terpenes produced by the terpene synthase of the present invention may be further processed to an alcohol, preferably α-santalol, β-santalol, α-trans-bergamotol and/or epi-β-santalol.

BRIEF DESCRIPTION OF THE DRAWINGS

FIG. 4: Nucleic acid sequence of the SaSSy terpene synthase of the present invention.

FIG. 5: Amino acid sequence of the SaSSy terpene synthase of the present invention.

FIGS. 6A and 6B: Clustal alignment of terpene synthases: FB299123-125—terpene synthase from *Vetiveria zizanoides* (WO 2006/134523), AF484125—5-epi-aristolochene synthase from *Nicotiana attenuata*, AB438045—linalool synthase from *Backhousia citriodora*, Santalene—SaSSy santalene synthase of the present invention from *Santalum album*.

FIGS. 10a-10g: Alignment of nucleic acid sequences of terpene synthases from *S. austrocaledonicum*, *S. spicatum* and *S. album*.

FIGS. 11a-11c: Alignment of amino acid sequences of terpene synthase proteins from *S. austrocaledonicum*, *S. spicatum* and *S. album*.

FIGS. 12a-12d: Alignment of amino acid sequences of terpene synthase proteins from *S. austrocaledonicum*, *S. spicatum* and *S. album*, compared to the amino acid sequences of DQ785793.1—cineole synthase from *Salvia fruticosa* and DQ785794.1—sabinene synthase from *Salvia pomifera*.

DETAILED DESCRIPTION

Figure 1:
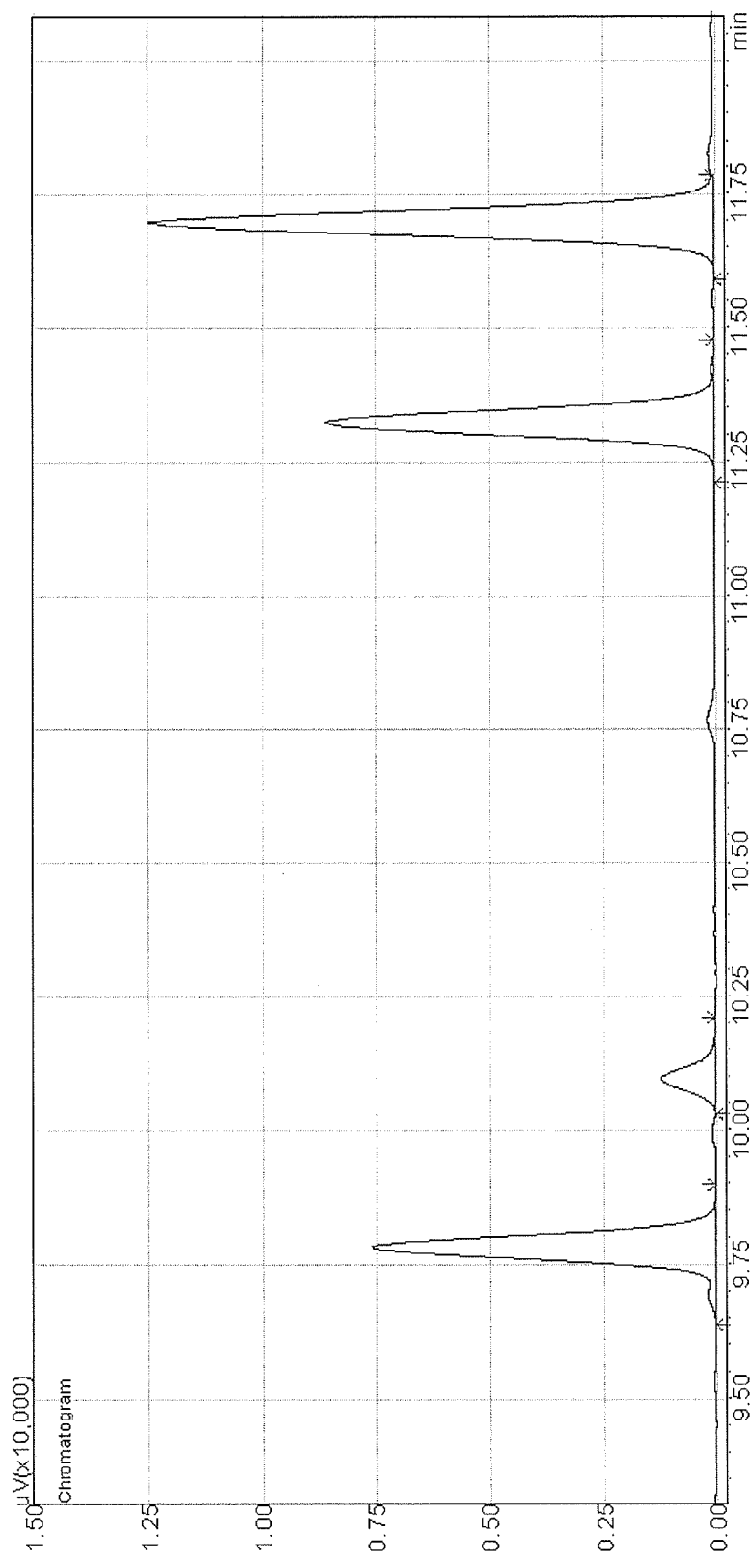
FIG. 1: Chromatogram of natural sandalwood oil from *S. album*. The 4 main peaks are α-santalene, E-α-bergamotene, epi-β-santalene and β-santalene.

In accordance with the present invention, a novel terpene synthase gene from *S. album* has been discovered, SaSSy. Orthologous genes from two other phylogenetically divergent species (SspiSSy from *S. spicatum* and SauSSy from *S. austrocaledonicum*) were also found. The novel genes are characterised by the DNA sequences shown in SEQ ID NO: 1, SEQ ID NO: 3 or SEQ ID NO: 5.

The novel gene disclosed in SEQ ID NO:1 is hereinafter generally referred to as SaSSy, the novel gene disclosed in SEQ ID NO:3 is hereinafter generally referred to as SauSSy, and the novel gene disclosed in SEQ ID NO:5 is hereinafter generally referred to as SspiSSy. The DNA and protein sequences of SaSSy, SauSSy and SspiSSy are very highly conserved, with 94-98% identity over the amino acids of the ORFs. Key domains of the gene are very highly conserved (see FIGS. 4 and 5).

The novel terpene synthase enzyme catalyses the production from FPP of terpenoids, preferably terpenes, more preferably sesquiterpenes chosen from the following: α-santalene, α-trans-bergamotene, epi-β-santalene and β-santalene.

More specifically, SaSSy, SauSSy and SspiSSy are sesquiterpene synthases and most specifically, santalene synthases. As used herein, a "terpene synthase" is an enzyme that catalyses the production of one or more terpenoids, or more preferably one or more terpenes from a substrate; a "sesquiterpene synthase" is an enzyme that catalyses the synthesis of a sesquiterpenoid, or more preferably a sesquiterpene and a "santalene synthase" is an enzyme that catalyses the synthesis of a santalene. The formation of terpenoids and/or terpenes from a substrate can be assessed using any method known in the art, including but not limited to, the enzyme assays and mass spectrometry described in Examples 6 and 7, below.

Terpenoids are defined herein as compounds derived from prenyl diphosphate substrates by activity of a terpene synthase and possible subsequent modification by other enzymes. Included with the term terpenoid are non-oxygenated terpene olefins (terpenes), oxygenated terpenes, as well as other derivatives such as terpenols.

As used herein, a terpene is an unsaturated hydrocarbon based on the isoprene unit ($C_5H_8$), and having a general formula $C_{10}H_{16}$. Terpenes can be acyclic, monocyclic or polycyclic. Terpenes include, but are not limited to, monoterpenes, which contain 10 carbon atoms; sesquiterpenes, which contain 15 carbon atoms; diterpenes, which contain 20 carbon atoms, and triterpenes, which contain 30 carbon atoms. Reference to a terpene includes stereoisomers of the terpene.

Reference to a santalene in the present invention includes α-santalene and β-santalene, and any stereoisomer thereof, including, for example, (+)-epi-β-santalene, (−)-β-santalene, (+)-β-santalene, (+)-α-santalene, and (−)-α-santalene.

This isolation of these novel terpene synthase genes will allow for the synthesis of sandalwood oil which is similar to the natural oil. To date, it is possible to synthesize some sesquiterpenes using sesquiterpene synthases from other sources, but the range of component sesquiterpenes and end ratio of each component is not similar to that of the natural sandalwood oil.

Preferably, the terpene synthase gene of the present invention is isolated from a member of the genus *Santalum*. More preferably, it is isolated from *S. album* (Indian Sandalwood, White Sandalwood, Chandana), *S. spicatum* (Australian Sandalwood) or *S. austrocaledonicum*. However, the gene may alternatively be isolated from a plant selected from the following: *S. acuminatum* (Desert Quandong, Sweet Quandong, Native Peach); *S. ellipticum* (Coast Sandalwood); *S. fernandezianum; S. freycinetianum; S. haleakalae; S. lanceolatum* (Northern Sandalwood); *S. macgregorii; S. murrayanum* (Bitter Quandong); *S. obtusifolium; S. paniculatum; S. salicifolium* (Willowleaf Sandalwood); or *S. yasi*.

Thus there is provided an isolated terpene synthase, wherein the terpene synthase is a *Santalum* terpene synthase, and the terpene synthase catalyzes the production of a santalene.

Preferably, such a terpene synthase comprises:
(a) a sequence of amino acids selected from among the sequences set forth in SEQ ID NO:2, SEQ ID NO:4 and SEQ ID NO: 6; or
(b) a sequence of amino acids that is at least or at least about 60%, 65%, 70%, 75%, 80%, 85%, 90%, 95% or more identical to the sequence of amino acids set forth in SEQ ID NO:2; or;
(c) a fragment of (a) or (b); wherein
the terpene synthase catalyzes the production of a santalene.

In another embodiment, the invention provides an isolated terpene synthase, comprising:
(a) the sequence of amino acids set forth in SEQ ID NO: 2, SEQ ID NO: 4 or SEQ ID NO: 6;
(b) the sequence of amino acids encoded by the nucleic acid molecule of any of claims 1 to 5;
(c) a sequence of amino acids that is at least or at least about 60%, 65%, 70%, 75%, 80%, 85%, 90%, 95% or more identical to the sequence of amino acids set forth in SEQ ID NO:2; or
(d) a fragment of (a), (b) or (c), where the terpene synthase catalyzes the production of a terpene.

Preferably, such a terpene synthase comprises amino acids selected from among amino acids corresponding to positions 32-42, 221-425, 321-325, 314-315 and 423-426 of SEQ ID NO:2.

More preferably, the terpene synthase catalyzes the production of a terpene selected from among monocyclic sequiterpenes, bicyclic sesquiterpenes and tricyclic sesquiterpenes, particularly wherein the terpene is synthesised from an acyclic pyrophosphate terpene precursor such as farnesyldiphosphate (FPP).

The nucleotide sequence of SEQ ID NO: 1, SEQ ID NO: 3 or SEQ ID NO: 5 encompasses a single ORF. The invention provides an isolated DNA nucleotide sequence corresponding to the terpene synthase gene SaSSy nucleotide sequence depicted in SEQ ID NO:1, the SauSSy nucleotide sequence depicted in SEQ ID NO: 3 or the SspiSSy nucleotide sequence depicted in SEQ ID NO: 5 or sequences substantially homologous to SEQ ID NO: 1, SEQ ID NO: 3 or SEQ ID NO: 5, or fragments thereof. The invention further provides a DNA sequence comprising the complement of SEQ ID NO: 1, SEQ ID NO: 3 or SEQ ID NO: 5, or sequences substantially homologous to SEQ ID NO: 1, SEQ ID NO: 3 or SEQ ID NO: 5, or fragments thereof.

The invention therefore provides an isolated nucleic acid molecule that encodes a terpene synthase and is selected from among:
(a) a nucleic acid molecule comprising the sequence of nucleotides set forth in SEQ ID NO: 1, SEQ ID NO: 3 or SEQ ID NO: 5;
(b) a nucleic acid molecule that is a fragment of a);
(c) a nucleic acid molecule comprising a sequence of nucleotides that is complementary to (a) or (b); and
(d) a nucleic acid molecule that encodes a terpene synthase having at least or at least about 60%, 65%, 70%, 75%, 80%, 85%, 90%, 95%, 96%, 97%, 98%, 99% identity to any one of (a)-(c);
wherein the nucleic acid molecule encodes a terpene synthase.

The isolated nucleic acid molecules that encode the terpene synthase preferably have at least or at least about 61%, 65%, 70%, 75%, 80%, 85%, 90%, 95%, 96%, 97%, 98%, 99% identity to the terpene synthase encoded by any one of (a)-(d), wherein the differences in the sequence are amino acid substitutions.

The nucleotide sequences of SaSSy, SauSSy and SspiSSy are very highly conserved (see FIG. 4).

The nucleotide sequence of SaSSy, as set forth in SEQ ID NO:1, encodes a polypeptide that has a proline at amino acid position 143 (SEQ ID NO:2). However, the encoded polypeptide may alternatively have a serine at position 143 (SEQ ID NO:7 and SEQ ID NO:8). The two variant sequences are substantially homologous, particularly as the two residues are both polar, and subsequent tests have shown that when the two proteins are assayed they have substantially the same activity and produced each compound in substantially the same proportions. Generally, the two variant proteins have identical activities and produced each compound in identical proportions.

The DNA sequence may also correspond to a fragment of SEQ ID NO: 1, SEQ ID NO: 3 or SEQ ID NO: 5. Preferably, the fragment is selected from the following locations of SEQ ID NO:1: position 961-975 (generally corresponding to the DDxxD motif), position 94-126 (generally corresponding to the R(R/P)$X_8$W motif). Without being bound to any particular theories, it is believed that the DDxxD motif is responsible for chelating the divalent metal ion (for example, magnesium) and if it is removed, the protein may be rendered completely non-functional. The R(R/P)$X_8$W motif at the start of the protein is also believed to be unique to terpene synthases and is understood to be involved in the specific ionisation of non-chiral FPP or GPP to chiral nerolidyl- and neryl diphosphate respectively.

Other regions which may be essential for the specific function of the three santalene synthases of the present invention are amino acid positions 314 and 315 (nucleotide positions 940 to 945), by inference of the work of Kampranis et al. (2007). Exchanging these residues with larger or smaller residues of similar polarity is likely to change the size of the active site, and hence the products produced upon catalysis. Amino acid residues 422 to 426 of the santalene synthases (nucleotides 1264 to 1278) may also be responsible for the final product profile, as Kampranis et al. demonstrated. The significance of the proline residue at the start of the α19 helix is to hold the substrate tightly, and removal of this may cause a lack of functionality. Amino acid positions 221-426 define a larger region encompassing many of the more important regions that are preferably retained. Thus, residues in these locations are preferably conserved for full function, or varied slightly for altered function. Therefore, preferably the DNA sequence may also correspond to a fragment of SEQ ID NO: 1, SEQ ID NO: 3 or SEQ ID NO: 5 selected from the following locations of SEQ ID NO:1: position 940-945, 661-1278 or 1264-1278.

Homologous nucleic acid molecules refer to a pre-determined number of identical or homologous nucleotides. Homology includes substitutions that do not change the encoded amino acid (i.e., "silent substitutions") as well identical residues. Substantially homologous nucleic acid molecules hybridize typically at moderate stringency or at high stringency all along the length of the nucleic acid or along at least about 70%, 80% or 90% of the full-length nucleic acid molecule of interest. Also contemplated are nucleic acid molecules that contain degenerate codons in place of codons in the hybridizing nucleic acid molecule.

Whether any two nucleic acid molecules have nucleotide sequences that are at least 80%, 85%, 90%, 95%, 96%, 97%, 98% or 99% "identical" can be determined using known computer algorithms such as the "FAST A" program, using for example, the default parameters as in Pearson et al. (Proc. Natl. Acad. Sci. USA 85:2444 (1988); other programs include the GCG program package (Devereux, J., et al., Nucleic Acids Research 12(I):387 (1984)), BLASTP, BLASTN, FASTA (Atschul, S. F., et al., J. Molec. Biol. 215:403 (1990); Guide to Huge Computers, Martin J. Bishop, ed., Academic Press, San Diego (1994), and Carillo et al., SIAM J. Applied Math 48:1073 (1988)). Other commercially or publicly available programs include DNAStar "MegAlign" program (Madison, Wis.) and the University of Wisconsin Genetics Computer Group (UWG) "Gap" program (Madison, Wis.)). Percent homology or identity of nucleic acid molecules can be determined, for example, by comparing sequence information using a GAP computer program (e.g., Needleman et al., J. Mol. Biol. 48: 443 (1970), as revised by Smith and Waterman (Adv. Appl. Math. 2:482 (1981)). Briefly, a GAP program defines similarity as the number of aligned symbols (i.e., nucleotides) which are similar, divided by the total number of symbols in the shorter of the two sequences. Default parameters for the GAP program can include: (1) a unary comparison matrix (containing a value of 1 for identities and 0 for non identities) and the weighted comparison matrix of Gribskov et al., Nucl. Acids Res. 14:6745 (1986), as described by Schwartz and Dayhoff, eds., Atlas of Protein Sequence and Structure, National Biomedical Research Foundation, pp. 353-358 (1979); (2) a penalty of 3.0 for each gap and an additional 0.10 penalty for each symbol in each gap; and (3) no penalty for end gaps.

Substantial homology or identity exists when polynucleotide sequence of the present invention, or fragment thereof, will specifically hybridise to another SaSSy, SauSSy or SspiSSy polynucleotide (or a complementary strand thereof) under selective hybridisation conditions. As used herein, "specifically hybridises" refers to annealing, by complementary base-pairing, of a nucleic acid molecule (e.g., an oligonucleotide) to a target nucleic acid molecule. Those of skill in the art are familiar with in vitro and in vivo parameters that affect specific hybridization, such as length and composition of the particular molecule. Parameters particularly relevant to in vitro hybridization further include annealing and washing temperature, buffer composition and salt concentration. Exemplary washing conditions for removing non-specifically bound nucleic acid molecules at high stringency are 0.1× SSPE, 0.1% SDS, 65° C., and at medium stringency are 0.2×SSPE, 0.1% SDS, 50° C. Equivalent stringency conditions are known in the art. The skilled person can readily adjust these parameters to achieve specific hybridization of a nucleic acid molecule to a target nucleic acid molecule appropriate for a particular application, under conditions that are low, medium or high stringency.

Typically, selective hybridisation will occur when there is at least about 55% identity over a stretch of at least about 14 nucleotides, preferably at least about 65%, more preferably at least about 75% and most preferably at least about 90%. The length of homology comparison, as described, may be over longer stretches and in certain embodiments will often be over a stretch of at least about nine nucleotides, usually at least about 20 nucleotides, more usually at least about 24 nucleotides, typically at least about 28 nucleotides, more typically at least about 32 nucleotides and preferably at least about 36 or more nucleotides.

Thus, the polynucleotide sequences of the invention preferably have at least 75%, more preferably at least 85%, more preferably at least 90% homology to the sequences shown in the sequence listings herein. More preferably there is at least 95%, more preferably at least 98%, homology. Nucleotide homology comparisons may be conducted as described below for polypeptides. A preferred sequence comparison program is the GCG Wisconsin Bestfit program.

In the context of the present invention, a homologous sequence is taken to include a nucleotide sequence which is at least 60, 70, 80 or 90% identical, preferably at least 95 or 98% identical at the nucleic acid level over at least 20, 50, 100, 200, 300, 500, 1000, 1500 or 1710 nucleotides with the corresponding nucleotide sequences set out in SEQ ID NO: 1, SEQ ID NO: 3 or SEQ ID NO: 5. In particular, homology should typically be considered with respect to those regions of the nucleic acid sequence that encode contiguous amino acid sequences known to be essential for the function of the terpene synthase gene, rather than non-essential neighboring sequences. For example, the nucleic acid sequence that codes for amino acid positions 32-42 (nucleotides 94-126) and/or amino acid positions 321-325 (nucleotides 961-975), and/or alternatively the nucleic acid sequence that codes for amino acid positions 221-426 (nucleotides 661-1278), position 314-315 (nucleotides 940-945) and/or position 422-426 (nucleotides 1264-1278).

SaSSy, SauSSy or SspiSSy polynucleotide sequence fragments of the invention will preferably be at least 15 nucleotides in length, more preferably at least 20, 30, 40, 50, 100 or 200 nucleotides in length. Generally, the shorter the length of the polynucleotide sequence, the greater the homology required to obtain selective hybridisation. Consequently, where a polynucleotide sequence of the invention consists of less than about 30 nucleotides, it is preferred that the percentage identity is greater than 75%, preferably greater than 90% or 95% compared with the polynucleotide sequences set out in the sequence listings herein. Conversely, where a polynucleotide sequence of the invention consists of, for example, greater than 50 or 100 nucleotides, the percentage identity compared with the polynucleotide sequences set out in the sequence listings herein may be lower, for example greater than 50%, preferably greater than 60 or 75%.

Nucleic acid sequences according to the present invention which are homologous to the sequences as represented by SEQ ID NO: 1, SEQ ID NO: 3 or SEQ ID NO: 5 can be characterized and isolated according to any of the techniques known in the art, such as amplification by means of sequence-specific primers, hybridization with sequence-specific probes under more or less stringent conditions, serological screening methods or via the LiPA typing system.

The genomic DNA sequence of SaSSy is provided in SEQ ID NO:9.

The RNA of the SaSSy, SauSSy and SspiSSy genes is also provided. The RNA sequence is preferably derived from the DNA sequences described above and provided in SEQ ID NO: 1, SEQ ID NO: 3 or SEQ ID NO: 5.

The invention also provides RNA fragments hybridisable with the genomic DNA of SaSSy, SauSSy or SspiSSy. The RNA or RNA fragment sequence may also be derived from the cDNA sequence of SaSSy, SauSSy or SspiSSy or fragments thereof.

Nucleic acid sequences and fragments, which include some deletions or mutations which would not substantially alter their ability to hybridize with SaSSy, SauSSy or SspiSSy, are also provided by the present invention. Such variants are to be considered as forming obvious equivalents of the DNA, RNA or fragments referred to above.

Other preferred variant nucleic acid sequences of the present invention include sequences which are redundant as a result of the degeneracy of the genetic code compared to any of the above-given nucleic acid sequences of the present invention. These variant nucleic acid sequences will thus encode the same amino acid sequences as the nucleic acid sequences they are derived from. Preferably, the DNA, RNA or cDNA of these variants are hybridisable to corresponding parts of the SaSSy, SauSSy or SspiSSy gene sequence.

Also included within the present invention are sequence variants of the DNA sequence of SEQ ID NO: 1, SEQ ID NO: 3 or SEQ ID NO: 5 or corresponding RNA sequences or fragments thereof, containing either deletions and/or insertions of one or more nucleotides, especially insertions or deletions of 1 or more codons.

Also included are substitutions of some non-essential nucleotides by others (including modified nucleotides and/or inosine).

Particularly preferred variant polynucleotides of the present invention also include sequences which hybridise under stringent conditions with any of the nucleic acid sequences of the present invention. Thus, sequences which show a high degree of homology (similarity) to any of the nucleic acid sequences of the invention as described above are preferred. Particularly preferred are sequences which are at least 80%, 85%, 90%, 95% or more homologous to said nucleic acid sequences of the invention. Preferably, said sequences will have less than 20%, 15%, 10%, or 5% variation of the original nucleotides of said nucleic acid sequences.

Primer and probes are further provided, which can be made starting from any DNA or RNA sequence or sequence fragment according to the invention. Preferably, such probes or primers are between about 5 to 50 nucleotides long, more preferably from about 10 to 25 nucleotides. Preferably, the probe or primer oligonucleotide contains at least or at least about 15, 20, 25, 30, 35, 40, 45, 50, 60 or more contiguous nucleotides from a terpene synthase nucleic acid molecule. Probes and primers of the present invention may be used in PCR, sequencing reactions, hybridisation reactions and other applications known to the skilled person. Preferably, the probes and/or primers will be generated from regions of high G and C content, which are readily identified by the skilled addressee.

The present invention also relates to an oligonucleotide primer comprising part of SEQ ID NO: 1, SEQ ID NO: 3 or SEQ ID NO: 5, said primer being able to act as a primer for specifically amplifying the nucleic acids of SaSSy, SauSSy or SspiSSy. Preferably, the primer is a single stranded DNA oligonucleotide sequence capable of acting as a point of initiation for synthesis of a primer extension product which is complementary to the nucleic acid strand to be copied. The specific length and sequence of the primer used will depend on the complexity of the required DNA or RNA targets, as well as on the conditions of primer use, such as temperature and ionic strength. The fact that amplification primers do not have to match exactly with corresponding template sequence to warrant proper amplification is amply documented in the literature (Kwok et al., 1990).

The amplification method used can be either polymerase chain reaction (PCR; Saiki et al., 1988), ligase chain reaction (LCR; Landgren et al., 1988; Wu & Wallace, 1989; Barany, 1991), nucleic acid sequence-based amplification (NASBA; Guatelli et al., 1990; Compton, 1991), transcription-based amplification system (TAS; Kwoh et al., 1989), strand displacement amplification (SDA; Duck, 1990; Walker et al., 1992) or amplification by means of Qβ replicase (Lizardi et al., 1988; Lomeli et al., 1989) or any other suitable method to amplify nucleic acid molecules using primer extension. During amplification, the amplified products can be conveniently labelled either using labelled primers or by incorporating labelled nucleotides. Labels may be isotopic ($^{32}$P, $^{35}$S, etc.) or non-isotopic (biotin, digoxigenin, etc.). The amplification reaction is repeated between 20 and 70 times, advantageously between 25 and 45 times.

The present invention also relates to an oligonucleotide probe comprising part of SEQ ID NO: 1, SEQ ID NO: 3 or SEQ ID NO: 5, with said probe being able to act as a hybridisation probe for the SaSSy, SauSSy or SspiSSy gene. Preferably, the probe is a single stranded sequence-specific oligonucleotide sequence which has a sequence that is complementary to the target sequence of the SaSSy, SauSSy or SspiSSy gene to be detected.

Those skilled in the art will recognize that the stringency of hybridisation will be affected by such conditions as salt concentration, temperature, or organic solvents, in addition to the base composition, length of the complementary strands and the number of nucleotide base mismatches between the hybridising nucleic acids. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. An example of stringent hybridisation conditions is 65° C. and 0.1×SSC (1×SSC=0.15 M NaCl, 0.015 M sodium citrate pH 7.0).

Optionally, the probe of the invention is labelled and/or attached to a solid substrate. The solid substrate can refer to any substrate to which an oligonucleotide probe can be coupled, provided that it retains its hybridization characteristics and provided that the background level of hybridization remains low. Usually the solid substrate will be a microtiter plate, a membrane (e.g., nylon or nitrocellulose) or a microsphere (bead). Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin or haptens.

The probes of the invention may include also an isolated polynucleotide attached to a label or reporter molecule and may be used to isolate other polynucleotide sequences, having sequence similarity by standard methods. For techniques for preparing and labelling probes see, e.g., Sambrook and Russell (2001) or Ausubel et al. (2001).

Oligonucleotides according to the present invention and used as primers or probes may also contain or consist of nucleotide analogues such as phosphorothioates (Matsukura et al., 1987), alkylphosphonates (Miller et al., 1979) or peptide nucleic acids (Nielsen et al., 1991; Nielsen et al., 1993), or may contain intercalating agents (Asseline et al., 1984). The introduction of these modifications may be advantageous in order to positively influence characteristics such as hybridization kinetics, reversibility of the hybrid-formation, biological stability of the oligonucleotide molecules, etc.

Recombinant DNAs containing fragments of the DNA sequence of the SaSSy, SauSSy or SspiSSy genes are also provided by the present invention, and may be used as, for example, probes. Preferably, the plasmid used to generate the recombinant DNA is a plasmid amplifiable in prokaryotic or eukaryotic cells and carrying said fragments. For example, using cloned DNA containing a DNA fragment of the SaSSy gene as a molecular hybridization probe, either by marking with radionucleotides or with fluorescent reagents, the gene may be detected directly, for example, in different tissues of a sandalwood tree.

SaSSy, SauSSy or SspiSSy polynucleotide sequences (preferably in the form of probes) may also be immobilised to a solid phase support for the detection of the SaSSy gene. In an alternate form of the invention, SaSSy, SauSSy or SspiSSy polynucleotide sequences together with other polynucleotide sequences (such as from other terpene synthase genes) may be immobilized on a solid support in such a manner as to permit identification of the presence of suitable terpene synthase genes and/or any of the other polynucleotide sequences bound onto the solid support in a material such as a tree sample.

Techniques for producing immobilized libraries of DNA molecules have been described in the art. Generally, most prior art methods describe the synthesis of single-stranded nucleic acid molecule libraries, using for example masking techniques to build up various permutations of sequences at the various discrete positions on the solid substrate. U.S. Pat. No. 5,837,832 describes an improved method for producing DNA arrays immobilized to silicon substrates based on very large scale integration technology. In particular, U.S. Pat. No. 5,837,832 describes a strategy called "tiling" to synthesize specific sets of probes at spatially defined locations on a substrate that may be used to produce the immobilized DNA libraries of the present invention. U.S. Pat. No. 5,837,832 also provides references for earlier techniques that may also be used. Thus, polynucleotide sequence probes may be synthesised in situ on the surface of the substrate.

Alternatively, single-stranded molecules may be synthesised off the solid substrate and each pre-formed sequence applied to a discrete position on the solid substrate. For example, polynucleotide sequences may be printed directly onto the substrate using robotic devices equipped with either pins or piezoelectric devices.

The library sequences are typically immobilized onto or in discrete regions of a solid substrate. The substrate may be porous to allow immobilization within the substrate or substantially non-porous, in which case the library sequences are typically immobilized on the surface of the substrate. The solid substrate may be made of any material to which polypeptides can bind, either directly or indirectly. Examples of suitable solid substrates include flat glass, silicon wafers, mica, ceramics and organic polymers such as plastics, including polystyrene and polymethacrylate. It may also be possible to use semi-permeable membranes such as nitrocellulose or nylon membranes, which are widely available. The semi-permeable membranes may be mounted on a more robust solid surface such as glass. The surfaces may optionally be coated with a layer of metal, such as gold, platinum or other transition metal. A particular example of a suitable solid substrate is the commercially available BiaCore™ chip (Pharmacia Biosensors).

Preferably, the solid substrate is generally a material having a rigid or semi-rigid surface. In preferred embodiments, at least one surface of the substrate will be substantially flat, although in some embodiments it may be desirable to physically separate regions for different polymers with, for example, raised regions or etched trenches. It is also preferred that the solid substrate is suitable for the high density application of DNA sequences in discrete areas of typically from 50 to 100 nm, giving a density of 10000 to 40000 dots/cm$^{-2}$.

The solid substrate is conveniently divided up into sections. This may be achieved by techniques such as photoetching, or by the application of hydrophobic inks, for example teflon-based inks (Cel-line, USA).

Attachment of the polynucleotide sequences to the substrate may be by covalent or non-covalent means. The polynucleotide sequences may be attached to the substrate via a layer of molecules to which the library sequences bind. For example, the polynucleotide sequences may be labelled with biotin and the substrate coated with avidin and/or streptavidin. A convenient feature of using biotinylated polynucleotide sequences is that the efficiency of coupling to the solid substrate can be determined easily. Since the polynucleotide sequences may bind only poorly to some solid substrates, it is often necessary to provide a chemical interface between the solid substrate (such as in the case of glass) and the nucleic acid sequences. Examples of suitable chemical interfaces include hexaethylene glycol. Another example is the use of polylysine coated glass, the polylysine then being chemically modified using standard procedures to introduce an affinity ligand. Other methods for attaching molecules to the surfaces of solid substrate by the use of coupling agents are known in the art, see for example WO 98/49557.

Binding of complementary polynucleotide sequences to the immobilized nucleic acid library may be determined by a variety of means such as changes in the optical characteristics of the bound polynucleotide sequence (i.e., by the use of ethidium bromide) or by the use of labelled nucleic acids, such as polypeptides labelled with fluorophores. Other detection techniques that do not require the use of labels include optical techniques such as optoacoustics, reflectometry, ellipsometry and surface plasmon resonance (see WO 97/49989).

Thus, the present invention provides a solid substrate having immobilized thereon at least one polynucleotide of the present invention, preferably two or more different polynucleotide sequences of the present invention. In a preferred embodiment the solid substrate further comprises polynucleotide sequences derived from genes other than the SaSSy, SauSSy or SspiSSy polynucleotide sequences.

Preferably, the transcription of the SaSSy, SauSSy or SspiSSy genes is up-regulated or promoted, for example in an artificial system such as host cells or recombinant plants, which may result in enhanced oil production. Such up-regulation or enhancement may be achieved by a myriad of means, such as inserting additional or alternative regulation sequences upstream and/or downstream of the genes in question, or generating mutants of the existing regulatory sequences which are capable of increasing transcription due to, for example, increased binding of regulatory elements.

The invention also covers polypeptides encoded by the above RNA and DNA nucleotide sequences and fragments thereof. The invention further provides an isolated SaSSy, SauSSy or SspiSSy amino acid sequence as shown in SEQ ID NO: 2, SEQ ID NO: 4 or SEQ ID NO: 6 and fragments thereof. More desirably, the SaSSy, SauSSy or SspiSSy amino acid sequences are provided in substantially purified form. Further provided are polypeptide fragments having lower molecular weights and having peptide sequences or fragments in common with those shown in SEQ ID NO: 2, SEQ ID NO: 4 or SEQ ID NO: 6.

As used herein, an "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the α-carbon has a side chain).

In keeping with standard polypeptide nomenclature described in J. Biol. Chem., 243:3557-3559 (1968), and adopted 37 C.F.R. §§1.821-1.822, abbreviations for the amino acid residues are shown in the below Table of Correspondence:

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glu and/or Gln |
| W | Trp | Tryptophan |
| R | Arg | Arginine |
| D | Asp | Aspartic acid |
| N | Asn | Asparagine |
| B | Asx | Asn and/or Asp |
| C | Cys | Cysteine |
| X | Xaa | Unknown or other |

It should be noted that all amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence and modified and unusual amino acids, such as those referred to in 37 C.F.R. §§1.821-1.822, and incorporated herein by reference. Furthermore, it should be noted that a dash at the beginning or end of an amino acid residue sequence indicates a peptide bond to a further sequence of one or more amino acid residues, to an amino-terminal group such as $NH_2$ or to a carboxyl-terminal group such as COOH.

As used herein, "naturally occurring amino acids" refer to the 20 L-amino acids that occur in polypeptides, and "non-natural amino acid" refers to an organic compound containing an amino group and a carboxylic acid group that is not one of the naturally-occurring amino acids listed in the Table of Correspondence. Non-naturally occurring amino acids thus include, for example, amino acids or analogs of amino acids other than the 20 naturally-occurring amino acids and include, but are not limited to, the D-isostereomers of amino acids. Non-naturally occurring amino acids can be incorporated into the terpene synthases and variants thereof provided herein.

The term "isolated" is used to describe an amino acid sequence of the present invention that has been separated from components that accompany it in its natural state. Further, an amino acid sequence of the present invention is "substantially purified" when at least about 60 to 75% of a sample exhibits a single SaSSy amino acid sequence. A substantially purified SaSSy, SauSSy or SspiSSy amino acid sequence will typically comprise about 60 to 90% W/W of a sample, more usually about 95%, and preferably will be over about 99% pure. Protein purity or homogeneity may be indicated by a number of means well known in the art, such as polyacrylamide gel electrophoresis of a protein sample, followed by visualizing a single amino acid sequence band upon staining the gel. For certain purposes, higher resolution may be provided by using HPLC or other means well known in the art which are utilised for application.

The invention further contemplates fragments of the SaSSy, SauSSy or SspiSSy amino acid sequences. An amino acid sequence fragment in accordance with this aspect of the invention is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

In a highly preferred form of the invention, the fragments exhibit ligand-binding, immunological activity and/or other biological activities characteristic of SaSSy, SauSSy or SspiSSy amino acid sequences. More preferably, the fragments possess immunological epitopes consistent with those present on native SaSSy, SauSSy and SspiSSy amino acid sequences.

As used herein, "epitope" refers to an antigenic determinant of a polypeptide. An epitope could comprise three amino acids in a spatial conformation that is unique to the epitope. Generally, an epitope consists of at least five amino acids, and more usually consists of at least 8-10 amino acids. Methods of determining the spatial conformation of such amino acids are known in the art.

Preferred SaSSy, SauSSy or SspiSSy amino acid sequences of the invention will have one or more biological properties (e.g., in vivo, in vitro or immunological properties) of the native full-length amino acid sequence. Alternatively, fragments of the full-length SaSSy, SauSSy or SspiSSy amino acid sequences may have one or more biological properties of the genes which the full length amino acid sequence encodes.

Antibodies to specific regions of the SaSSy, SauSSy or SspiSSy genes may be determined by those skilled in the art, using, for example, the techniques recited in: G. W. Turner, and R. Croteau, "Organization of monoterpene biosynthesis in Mentha. Immunocytochemical localizations of geranyl diphosphate synthase, limonene-6-hydroxylase, isopiperitenol dehydrogenase, and pulegone reductase," Plant Physiol. 136:4215-4227 (2004).

Amino acid sequences, including analogues, fragments and derivatives, of the SaSSy, SauSSy or SspiSSy genes can be prepared synthetically (e.g., using the well known techniques of solid phase or solution phase peptide synthesis). Preferably, solid phase synthetic techniques are employed. Alternatively, SaSSy, SauSSy or SspiSSy amino acid sequences of the invention can be prepared using well known genetic engineering techniques, as described infra. In yet another embodiment, the amino acid sequences can be purified (e.g., by immuno affinity purification) from a biological material such as tree heartwood, sap, etc.

Amino acid sequences and derived peptide biomarkers to specific regions of the SaSSy, SauSSy or SspiSSy genes may be determined by those skilled in the art, using, for example, the techniques recited in: Zulak, K. G., Lippert, D. N., Kuzyk, M., Domanski, D., Chou, T., Borchers, C. H. and J. Bohlmann, "Targeted proteomics using selected reaction monitoring (SRM) reveals the induction of specific terpene synthases in a multi-level study of methyl jasmonate treated Norway spruce (Picea abies)," The Plant Journal 60:1015-1030 (2009).

SaSSy, SauSSy or SspiSSy amino acid sequence analogues preferably include those having an amino acid sequence wherein one or more of the amino acids is substituted with another amino acid, which substitutions do not substantially alter the biological activity of the molecule.

Variants of the SaSSy, SauSSy or SspiSSy terpene synthases of the invention may be used to attain desired enhanced or reduced enzymatic activity, modified regiochemistry or stereochemistry, or altered substrate utilization or product distribution. A variant or site direct mutant may be made by any methods known in the art. Variants and derivatives of native polypeptides can be obtained by isolating naturally-occurring variants, or the nucleotide sequence of variants, of other or same plant lines or species, or by artificially programming mutations of nucleotide sequences coding for native sandalwood polypeptides.

In the context of the invention, a homologous sequence is taken to include a SaSSy, SauSSy or SspiSSy amino acid sequence which is at least 60, 70, 80 or 90% homologous, preferably at least 95 or 98% homologous at the amino acid level over at least 20, 50, 100, 200 or 570 amino acids, with the amino acid sequence set out in SEQ ID NO: 2, SEQ ID NO: 4 or SEQ ID NO: 6. In particular, homology should typically be considered with respect to those regions of the sequence that encode contiguous amino acid sequences known to be essential for the function of the terpene synthase gene, rather than non-essential neighbouring sequences. For example, amino acid positions 32-42 and/or amino acid positions 321-325, or alternatively amino acid positions 221-425, positions 314-315 and/or positions 422-426.

Although homology can be considered in terms of similarity (i.e., amino acid residues having similar chemical properties/functions), in the context of the present invention it is preferred to express homology in terms of sequence identity.

The terms "substantial homology" or "substantial identity," when referring to SaSSy amino acid sequences, indicate that the amino acid sequence in question exhibits at least about 70% identity with an entire naturally-occurring SaSSy, SauSSy or SspiSSy amino acid sequence or portion thereof, usually at least about 80% identity and preferably at least about 90 or 95% identity.

As used herein, "sequence identity" refers to the number of identical amino acids (or nucleotide bases) in a comparison between a test and a reference polypeptide or polynucleotide. "Homologous polypeptides" refer to a pre-determined number of identical or homologous amino acid residues. Homology includes conservative amino acid substitutions as well as identical residues. Sequence identity can be determined by standard alignment algorithm programs used with default gap penalties established by each supplier.

For determination of homology of proteins, conservative amino acids can be aligned as well as identical amino acids; in this case, percentage of identity and percentage homology varies. Whether any two polypeptides have amino acid sequences that are at least 80%, 85%, 90%, 95%, 96%, 97%, 98% or 99% "identical" can be determined using known computer algorithms such as the "FAST A" program, using for example, the default parameters as in Pearson et al. (Proc. Natl. Acad. Sci. USA 85:2444 (1988); other programs include the GCG program package (Devereux, J., et al., Nucleic Acids Research 12(I):387 (1984)), BLASTP, BLASTN, FASTA (Atschul, S. F., et al., J. Molec. Biol. 215:403 (1990); Guide to Huge Computers, Martin J. Bishop, ed., Academic Press, San Diego (1994), and Carillo et al., SIAM J. Applied Math 48:1073 (1988)). For example, the BLAST function of the National Center for Biotechnology Information database can be used to determine identity. Other commercially or publicly available programs include DNAStar "MegAlign" program (Madison, Wis.) and the University of Wisconsin Genetics Computer Group (UWG) "Gap" program (Madison, Wis.)).

Percent homology or identity of proteins and/or nucleic acid molecules can be determined, for example, by comparing sequence information using a GAP computer program (e.g., Needleman et al., J. Mol. Biol. 48:443 (1970), as revised by Smith and Waterman (Adv. Appl. Math. 2:482 (1981)). Briefly, a GAP program defines similarity as the number of aligned symbols (i.e., nucleotides or amino acids) which are similar, divided by the total number of symbols in the shorter of the two sequences. Default parameters for the GAP program can include: (1) a unary comparison matrix (containing a value of 1 for identities and 0 for non identities) and the weighted comparison matrix of Gribskov et al., Nucl. Acids Res. 14:6745 (1986), as described by Schwartz and Dayhoff, eds., Atlas of Protein Sequence and Structure, National Biomedical Research Foundation, pp. 353-358 (1979); (2) a penalty of 3.0 for each gap and an additional 0.10 penalty for each symbol in each gap; and (3) no penalty for end gaps.

Therefore, as used herein, the term "identity" represents a comparison between a test and a reference polypeptide or polynucleotide. In one non-limiting example, "at least 90% identical to" refers to percent identities from 90 to 100% relative to the reference polypeptides. Identity at a level of 90% or more is indicative of the fact that, assuming for exemplification purposes a test and reference polynucleotide length of 100 amino acids are compared, no more than 10% (i.e., 10 out of 100) of amino acids in the test polypeptide differs from that of the reference polypeptides. Such differences can be represented as point mutations randomly distributed over the entire length of an amino acid sequence or they can be clustered in one or more locations of varying length up to the maximum allowable, e.g., 10/100 amino acid difference (approximately 90% identity). Differences are defined as amino acid substitutions, insertions or deletions. At the level of homologies or identities above about 85-90%, the result should be independent of the program and gap parameters set; such high levels of identity can be assessed readily, often without relying on software.

In a highly preferred form of the invention, a SaSSy, SauSSy or SspiSSy amino acid sequence analogue will have 80% or greater amino acid sequence identity to the SaSSy, SauSSy or SspiSSy amino acid sequence set out in SEQ ID NO: 2, SEQ ID NO: 4 or SEQ ID NO: 6. Examples of such amino acid sequence analogues within the scope of the invention include the amino acid sequence of SEQ ID NO: 2, SEQ ID NO: 4 or SEQ ID NO: 6 wherein: (a) one or more aspartic acid residues is substituted with glutamic acid; (b) one or more isoleucine residues is substituted with leucine; (c) one or more glycine or valine residues is substituted with alanine; (d) one or more arginine residues is substituted with histidine; (e) one or more tyrosine or phenylalanine residues is substituted with tryptophan; or (f) one or more proline residues are substituted with serine residues.

Naturally-occurring peptide variants are also encompassed by the invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides encoded by the sequences of the invention.

SaSSy, SauSSy or SspiSSy amino acid sequence derivatives are also provided by the invention and include amino acid sequences, analogues or fragments thereof which are substantially homologous in primary structure but which include chemical and/or biochemical modifications or unusual amino acids. Such modifications include, for example, acetylation, carboxylation, phosphorylation, glycosylation, hydroxylation, sulfation, ubiquitination, labelling (e.g., with radionuclides), and various enzymatic modifications, as will be readily appreciated by those well skilled in the art.

The terpene synthases of the present invention may also be provided in the form of a "chimeric protein" or "fusion protein." Such proteins are polypeptides operatively-linked to a different polypeptide. A chimeric or fusion protein provided herein can include one or more terpene synthase polypeptides, or a portion thereof, and one or more other polypeptides for any one or more of a transcriptional/translational control signals, signal sequences, a tag for localization, a tag for purification, part of a domain of an immunoglobulin G, and/or a targeting agent. These chimeric or fusion proteins include those produced by recombinant means as fusion proteins, those produced by chemical means, such as by chemical coupling, through, for example, coupling to sulfhydryl groups, and those produced by any other method whereby at least one polypeptide (i.e., terpene synthase), or a portion thereof, is linked, directly or indirectly via linker(s) to another polypeptide.

Where the SaSSy, SauSSy or SspiSSy amino acid sequences are to be provided in a labelled form, a variety of methods for labelling amino acid sequences are well known in the art and include radioactive isotopes such as $^3H$ or $^{14}C$, ligands which bind to labelled anti-ligands (e.g., antibodies), fluorophores, chemiluminescent agents, enzymes and anti-ligands which can serve as specific binding pair members for a labelled ligand. The choice of label depends on the sensitivity required, stability requirements, and available instrumentation. Methods of labelling amino acid sequences are well known in the art [See, e.g., Sambrook et al., Molecular Cloning: A Laboratory Manual, Second Edition, Cold Spring Harbor Laboratory Press, Cold Spring Harbor, N.Y. (1989); and Ausubel, F., Brent, R., Kingston, R. E., Moore, D. D., Seidman, J. G., Smith, J. A., Struhl, K., Current protocols in molecular biology, Greene Publishing Associates/Wiley Intersciences, New York (2001)].

The SaSSy, SauSSy and SspiSSy amino acid sequences of the invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

The invention also provides for fusion polypeptides, comprising SaSSy, SauSSy or SspiSSy amino acid sequences and fragments. Thus SaSSy, SauSSy or SspiSSy amino acid sequences may be fusions between two or more amino acid sequences of the present invention or between an amino acid sequence from SaSSy, SauSSy or SspiSSy and a related protein. Likewise, heterologous fusions may be constructed which would exhibit a combination of properties or activities of the derivative proteins. For example, ligand-binding or other domains may be "swapped" between different fusion polypeptides or fragments. Such homologous or heterologous fusion polypeptides may display, for example, altered strength or specificity of binding. Fusion partners include immunoglobulins, bacterial beta-galactosidase, trpE, protein A, beta-lactamase, alpha amylase, alcohol dehydrogenase and yeast alpha mating factor.

Modified SaSSy, SauSSy or SspiSSy amino acid sequences may be synthesised using conventional techniques, or may be encoded by a modified polynucleotide sequence and produced using recombinant nucleic acid methods. The modified polynucleotide sequence may also be prepared by conventional techniques. Fusion proteins will typically be made by either recombinant nucleic acid methods or may be chemically synthesised.

Variants of the terpene synthases of the invention may be used to attain desired enhanced or reduced enzymatic activity, modified regiochemistry or stereochemistry, or altered substrate utilization or product distribution. Furthermore, variants may be prepared to have at least one modified property, for example an increased affinity for the substrate, an improved specificity for the production of one or more desired compounds, a different product distribution, a different enzymatic activity, an increase of the velocity of the enzyme reaction, a higher activity or stability in a specific environment (pH, temperature, solvent, etc.), or an improved expression level in a desired expression system. A variant or site direct mutant may be made by any method known in the art.

As stated above, the invention provides recombinant and non-recombinant, isolated and purified polypeptides. Variants and derivatives of native polypeptides can be obtained by isolating naturally-occurring variants, or the nucleotide sequence of variants, of other or same plant lines or species, or by artificially programming mutations of nucleotide sequences coding for native terpene synthases. Alterations of the native amino acid sequence can be accomplished by any of a number of conventional methods.

Polypeptide variants resulting from a fusion of additional peptide sequences at the amino and carboxyl terminal ends of the polypeptides of the invention can be used to enhance expression of the polypeptides, aid in the purification of the protein or improve the enzymatic activity of the polypeptide in a desired environment or expression system. Such additional peptide sequences may be signal peptides, for example. Accordingly, the present invention encompasses variants of the polypeptides of the invention, such as those obtained by fusion with other oligo- or polypeptides and/or polypeptides which are linked to signal peptides.

Therefore, in an embodiment, the present invention provides a method for preparing a variant polypeptide having a desired terpene synthase activity, the method comprising the steps of:

(a) selecting any of the nucleic acids from the group consisting of SEQ ID NO: 1, SEQ ID NO: 3 or SEQ ID NO: 5, fragments or variants thereof as described above;

(b) modifying the selected nucleic acid to obtain at least one mutant nucleic acid;

(c) transforming host cells with the mutant nucleic acid sequence to express a polypeptide encoded by the mutant nucleic acid sequence;

(d) screening the polypeptide for a functional polypeptide having at least one modified property; and, (e) optionally, if the polypeptide has no desired variant terpene synthase activity, repeat the process steps (a) to (d) until a polypeptide with a desired variant terpene synthase activity is obtained (i.e., DNA shuffling).

In step (b), a large number of mutant nucleic acid sequences may be created, for example by random mutagenesis, site-specific mutagenesis, or DNA shuffling. The detailed procedures of gene shuffling are found in Stemmer, W. P., "DNA shuffling by random fragmentation and reassembly: in vitro recombination for molecular evolution," Proc. Natl. Acad. Sci. U.S.A. 91(22):10747-1075 (1994). In short, DNA shuffling refers to a process of random recombination of known sequences in vitro, involving at least two nucleic acids selected for recombination. For example mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered gene wherein predetermined codons can be altered by substitution, deletion or insertion.

Accordingly, any of SEQ ID NO: 1, SEQ ID NO: 3 or SEQ ID NO: 5, fragments and variants thereof may be recombined with a different sequence selected from any of SEQ ID NO: 1, SEQ ID NO: 3 or SEQ ID NO: 5, fragments and variants thereof, and/or with other terpene synthases encoding nucleic acids, for example isolated from an organism other than *S. album, S. austrocaledonicum* or *S. spicatum*. Thus, mutant nucleic acids may be obtained and separated, which may be used for transforming a host cell according to standard procedures.

In step (d), the polypeptide obtained in step (c) is screened for a modified property, for example a desired modified enzymatic activity. Examples of desired enzymatic activities for which an expressed polypeptide may be screened include enhanced or reduced enzymatic activity, as measured by $K_M$ or $V_{max}$ value, for example, modified regio-chemistry or stereochemistry, altered substrate utilization or product distribution. The screening of enzymatic activity can be performed according to procedures familiar to the skilled person. Methods for determining kinetic data and analysis of terpene products are given in, for example, Examples 13 and 14.

Step (e) provides for repetition of process steps (a)-(d), which may, preferably, be performed in parallel. Accordingly, by creating a significant number of mutant nucleic acids, many host cells may be transformed with different mutant nucleic acids at the same time, allowing for the subsequent screening of an elevated number of polypeptides. The chances of obtaining a desired variant polypeptide may thus be increased at the discretion of the skilled person.

In an embodiment, the present invention provides a method for preparing a nucleic acid encoding a variant polypeptide having terpene synthase activity, the method comprising the steps (a)-(e) disclosed above and further comprising the step of:

(f) if a polypeptide having desired variant terpene synthase activity was identified, acquiring the mutant nucleic acid obtained in step (c), which was used to transform host cells to express the variant terpene synthase following steps (c) and (d).

Preferably, the terpene synthase polypeptides of the invention catalyse the production of mono-, bi- and/or tricyclic sesquiterpenes. Preferably, the terpene synthase produces or synthesises the sesquiterpenes from an acyclic pyrophosphate terpene precursor substrate. An acyclic pyrophosphate terpene precursor is any acyclic pyrophosphate compound that is a precursor to the production of at least one terpene including, but not limited to, geranyl-pyrophosphate (GPP), farnesyl-diphosphate (FPP) and geranylgeranyl-pyrophosphate (GGPP). Generally, GPP is the precursor for the monoterpenes, FPP for the sesquiterpenes, and GGPP for the diterpenes. Preferably, the precursor is FPP.

As used herein, "catalyses the production of terpene(s)" or "catalyses the production of santalene(s)" refers to the ability of a terpene synthase to produce a terpene or a mixture thereof or specifically santalene or a mixture thereof, respectively, from a substrate, such as an acyclic terpene precursor. The formation of terpenes, such as santalene, from a substrate by a terpene synthase can be assessed using any method known in the art, including, but not limited to, the enzyme assays and mass spectrometry methods described in Examples 6 and 7, below.

Typically, a polypeptide that "catalyses the production of terpenes" produces a santalene or mixture thereof in an amount that is at least or at least about 1%, 2%, 3%, 4%, 5%, 10%, 15%, 20%, 25%, 30%, 35%, 40%, 45%, 50%, 55%, 60%, 65%, 70%, 75%, 80%, 85%, 90% or more of the total terpenes, by weight, from a particular substrate as measured using an in vitro assay, such as those assays described in Examples 6, 7, 13 and 14, wherein the terpene synthase, such as a santalene synthase, is mixed with a substrate, such as FPP, in the presence of $Mg^{2+}$. The santalenes produced by the synthase can include α-santalene and/or β-santalene, including (+)-epi-β-santalene, (−)-β-santalene, (+)-β-santalene, (+)-α-santalene, and (−)-α-santalene. For example, included among the terpene synthases provided herein are *Santalum* species terpene synthases that catalyze the production of α-santalene from FPP, wherein the amount of α-santalene produced from FPP at least is or is at least about 1%, 2%, 3%, 4%, 5%, 10%, 15%, 20%, 25%, 30%, 35%, 40%, 45%, 50%, 55%, 60%, 65%, 70%, 75%, 80%, 85%, 90% or more of the total terpenes (by weight) produced from FPP. In other examples, the terpene synthase catalyses the production of β-santalene from FPP, wherein the amount of β-santalene produced from FPP is at least or is at least about 1%, 2%, 3%, 4%, 5%, 10%, 15%, 20%, 25%, 30%, 35%, 40%, 45%, 50%, 55%, 60%, 65%, 70%, 75%, 80%, 85%, 90% or more of the total terpenes (by weight) produced from FPP.

Preferably, the isolated polypeptides of the present invention are capable of forming a bisabolyl cation from FPP and capable of further creating a bond between the $C_3$ and the $C_7$ carbon atom of FPP to produce a bicyclic or tricyclic sesquiterpene comprising a $C_3$-$C_7$ bond. Similarly, the polypeptide of the present invention is capable of forming a bisabolyl cation from FPP and capable of further creating a bond between the $C_2$ and the $C_7$ carbon atom of FPP to produce a bicyclic or tricyclic sesquiterpene comprising a $C_2$-$C_7$ bond.

The term "capable of synthesising" a compound, such as a specific sesquiterpene, and the terms "terpene synthase activity," preferably "sesquiterpene synthase activity," refers to polypeptides of the present invention, as well as nucleic acids encoding these polypeptides, which are capable of synthesizing a terpene, preferably a sesquiterpene, more preferably a santalene and most preferably the sesquiterpene and/or santalene compounds mentioned herein from at least one starting compound, which preferably is an acyclic pyrophosphate terpene precursor. Preferably, the acyclic terpene precursor is FPP which is given in the formula (I) below with standard numeration of the carbon skeleton of sesquiterpenes. OPP refers to pyrophosphate.

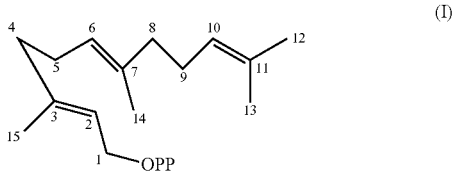

(I)

Preferably, the isolated terpene synthase polypeptides are capable of synthesising at least one sesquiterpene, more preferably at least one sesquiterpene having a santalene or bergamotene carbon skeleton. In a preferred embodiment, the polypeptide is capable of forming a bisabolyl cation from FPP, and capable of further creating a bond between the $C_3$ or $C_2$ and the $C_7$ carbon atom of FPP to produce one or several bi-cyclic and/or tricyclic sesquiterpenes.

The term "bond" refers to a single covalent bond.

The present invention relates to nucleic acids encoding polypeptides, as well as to the polypeptides themselves, capable of synthesising at least one bicyclic and/or tricyclic sesquiterpene comprising a $C_3$-$C_7$ bond. Preferably, the sesquiterpenes comprising a $C_3$-$C_7$ bond constitute at least about 1%, 2%, 3%, 4%, 5%, 10%, 15%, 20%, 25%, 30%, 35%, 40%, 45%, 50%, 55%, 60%, 65%, 70%, 80% or more of the total amount of sesquiterpene products synthesised by the terpene synthase. The quantitative sesquiterpene product distribution of a terpene synthase, for the purpose of the present invention, may be determined by employing the procedure detailed in Example 7, or by determination of the % by composition using techniques well known to those skilled in the art.

Accordingly, the present invention relates to isolated polypeptides capable of forming compounds having a $C_3$-$C_7$ bond of formulae (II) and/or (III) below,

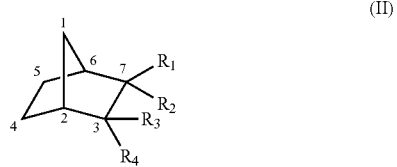

(II)

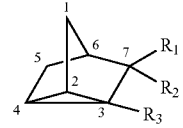

(III)

in which $R_1$, $R_2$, $R_3$, $R_4$ are, independently of each other a linear or branched alkyl or alkylene group from $C_1$ to $C_{20}$, and whereby $R_1$ and $R_2$ and/or $R_3$ and $R_4$ may form a double bond instead of two individual single bonds.

Preferably, $R_1$, $R_2$, $R_3$, and $R_4$ are, independently of each other, a linear or branched alkyl or alkylene group from $C_1$ to $C_{15}$, more preferably from $C_1$ to $C_{10}$, most preferably, from $C_1$ to $C_8$.

In particular, the polypeptides of the present invention are capable of forming compounds of formulae (IV), (V) and/or (VI) below,

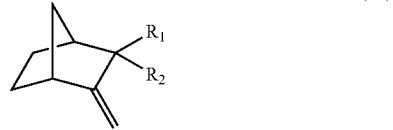

(IV)

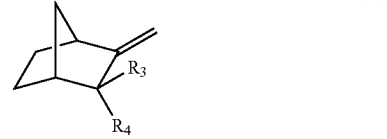

(V)

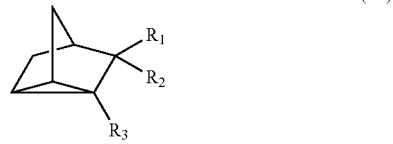

(VI)

in which $R_1$, $R_2$, $R_3$, $R_4$ are defined as above.

Preferably, in formula (IV) and/or (VI), either $R_1$ or $R_2$ is a $C_1$-$C_5$ alkyl and the other is a $C_2$-$C_8$ alkylene. In addition, $R_3$ in formula (VI) preferably is a $C_1$-$C_5$, more preferably a $C_1$-$C_3$ alkyl. Preferably, in formula (V), $R_3$ and $R_4$ are defined as $R_1$ and $R_2$ in formula (IV) above. Most preferably, $R_3$ of compound VI is a methyl group and $R_1$ and $R_2$ are alternately a methyl and a $C_6$ linear alkyl group.

Preferably the sesquiterpene is a santalene, more preferably an α-santalene or β-santalene. The santalene may be a stereoisomer selected from among (+)-epi-β-santalene, (−)-β-santalene, (+)-β-santalene, (+)-α-santalene, and (−)-α-santalene.

Preferably, the terpene synthase catalyzes the production of α-santalene, and the amount of α-santalene produced is at least or at least about 1%, 2%, 3%, 4%, 5%, 10%, 15%, 20%, 25%, 30%, 35%, 40%, 45%, 50%, 55%, 60%, 65%, 70%, 80% or more of the total amount of terpene produced.

The present invention relates to nucleic acids encoding a polypeptide, and to the polypeptide itself, capable of forming at least one sesquiterpene having a $C_2$-$C_7$ bond. According to a preferred embodiment, sesquiterpenes comprising a $C_2$-$C_7$ bond constitute at least about 1%, 2%, 3%, 4%, 5%, 10%, 15%, 20%, 25%, 30%, 35%, 40%, 45%, 50%, 55%, 60%, 65%, 70%, 80% or more of the total amount of sesquiterpene products synthesised by the terpene synthase.

The sesquiterpenes may be bergamotene, santalene and/or one of the isomers of these compounds, preferably stereoisomers. Preferably, the product is predominantly one stereoisomer, although it may further comprise a lesser amount of the other stereoisomer or enantiomer.

According to an embodiment, the present invention relates to isolated polypeptides capable of forming compounds having a $C_2$-$C_7$ bond according to the formulae (VII) and/or (VIII) below,

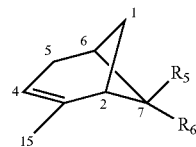

(VII)

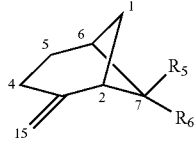

(VIII)

in which $R_5$ and $R_6$ are defined as $R_1$ and $R_2$ above. Preferably, $R_5$ is a methyl and $R_6$ is a $C_2$-$C_{10}$ alkenyl, or vice versa.

Preferably, at least one alkenyl possibly present in one of the residues $R_1$, $R_2$, $R_3$, $R_4$, $R_5$ or $R_6$ mentioned above is 4-methyl-3-pentenyl, while another residue linked to the same carbon atom is methyl.

The polypeptides capable of synthesizing the compounds of formulae (II), (III), (IV), (V), (VI), (VII) and/or (VIII) above preferably are the polypeptides having the amino acid sequences of SEQ ID NO: 2, SEQ ID NO: 4 or SEQ ID NO: 6, or polypeptide variants thereof.

Preferably, the sesquiterpenes having a $C_2$-$C_7$ bond are bergamotene, including its stereoisomers, in particular, cis-α-bergamotene, trans-α-bergamotene, trans-β-bergamotene and cis-β-bergamotene, for example.

Preferably, the terpene synthase catalyzes the production of bergamotene, and the amount of bergamotene produced is at least or at least about 1%, 2%, 3%, 4%, 5%, 10%, 15%, 20%, 25%, 30%, 35%, 40%, 45%, 50%, 55%, 60%, 65%, 70%, 80% or more of the total amount of terpene produced.

In a further aspect, the invention provides isolated polypeptides capable of synthesizing santalene and/or bergamotene. In a preferred embodiment, the invention provides isolated polypeptides capable of synthesizing one or more of the following: α-santalene, α-trans-bergamotene, epi-β-santalene, β-santalene and trans-trans-farnesol. Preferably, the isolated polypeptides are capable of synthesising at least β-santalene.

Most preferably, the SaSSy, SauSSy and SspiSSy terpene synthases of the present invention are able to synthesise at least two or more terpenes, preferably a terpene selected from among (+)-epi-β-santalene, (−)-β-santalene, (+)-β-santalene, (+)-α-santalene, and (−)-α-santalene, E-α-bergamotene, γ-curcumene, β-bisabolene, β-curcumene, α-curcumene, trans-trans-farnesol, α-pinene, camphene, limonene and α-terpinolene, more preferably α-santalene, α-trans-bergamotene, epi-β-santalene and β-santalene. Most preferably, the terpene synthase can synthesise two or more of the above compounds concurrently.

The enzymes may preferably be able to synthesise at least the four compounds listed above in the same reaction mixture under the same reaction conditions. Thus, it is preferable that the enzymes are able to convert FFP to at least the four listed terpenes under a single set of conditions, without need for further input of different starting compounds, different additional factors or alteration of reaction conditions to obtain one or more of the terpenes.

In a further aspect, the invention provides a vector comprising a nucleic acid of the invention.

A "vector," as used herein, includes prokaryotic vectors, viral vectors, or eukaryotic vectors and/or any recombinant vectors including, but not limited to, bacteriophages and plasmids. The vector may further be an expression vector. An expression vector includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. Viral vectors are engineered viruses that are operatively linked to exogenous genes to transfer (as vehicles or shuttles) the exogenous genes into cells.

The skilled person is capable of selecting a suitable vector according to the expression system. In one embodiment, the expression vectors include a cDNA sequence encoding the polypeptide operably linked to regulatory sequences such as transcriptional promoters, operators, or enhancers, mRNA ribosomal binding sites, and appropriate sequences which control transcription and translation initiation and termination for example.

Nucleotide sequences are "operably linked" when the regulatory sequence functionally relates to the cDNA sequence of the invention. Operably or operatively linking DNA segments means that the segments are arranged so that they function in concert for their intended purposes, e.g., transcription initiates in the promoter and proceeds through the coding segment to the terminator.

The vectors of the present invention may be used in the methods for preparing a genetically modified host organisms and/or cells, in host organisms and/or cells harbouring the nucleic acids of the invention and in the methods for producing or making terpene synthases, as is set out further below. Thus the invention provides a cell comprising the vectors of the present invention.

In an aspect, the present invention provides a method for preparing a terpene synthase comprising the steps of: culturing a host organism and/or cell modified to contain at least one nucleic acid sequence under conditions that provide for the expression of said encoded terpene synthase, wherein said at least one nucleic acid is a nucleic acid according to the invention. The terpene synthase can then optionally be purified. Examples of such production methods are provided in, for example, Examples 4, 5 and 12.

For example, the method of producing a terpene synthase may comprise the steps of:

(a) selecting a host organism and/or cell which does not express a nucleic acid having a sequence set forth in SEQ ID NO: 1, SEQ ID NO: 3 or SEQ ID NO: 5;

(b) transforming the organism with a nucleic acid molecule having a sequence set forth in SEQ ID NO: 1, SEQ ID NO: 3 or SEQ ID NO: 5; and (c) culturing the organism under conditions conducive to the production of the terpene synthase encoded by said nucleic acid.

The present invention also provides a method of producing a terpene synthase, the method comprising the steps of:

(a) selecting a host organism and/or cell which does express a nucleic acid molecule having a sequence set forth in SEQ ID NO: 1, SEQ ID NO: 3 or SEQ ID NO: 5;

(b) transforming the organism to express the nucleic acid molecule having a sequence set forth in SEQ ID NO: 1, SEQ ID NO: 3 or SEQ ID NO: 5 in higher quantity; and (c) culturing the organism under conditions conducive to the production of the terpene synthase encoded by said nucleic acid.

There is also provided a method of making a terpene, comprising contacting an acyclic pyrophosphate terpene precursor with the terpene synthase of the present invention, wherein the terpene synthase is heterologously expressed in a cell; the acyclic pyrophosphate terpene precursor is expressed in the same cell as the terpene synthase; and the step of contacting the acyclic pyrophosphate terpene precursor occurs in the cell.

There is also provided a method of making at least one terpene comprising: cultivating a cell under conditions conducive to the production of a terpene, wherein the cell heterologously expresses the terpene synthase of the invention; and the cell expresses an acyclic pyrophosphate terpene precursor.

The terpene synthases so produced may optionally be further isolated.

The acyclic pyrophosphate terpene precursor may be selected from among geranyl-pyrophosphate (GPP), farnesyl-diphosphate (FPP) and geranylgeranyl-pyrophosphate (GGPP).

Furthermore, the terpene is selected from among a sesquiterpene, a diterpene and a monoterpene, such as a bicyclic or tricyclic sesquiterpene, including preferably the terpene is selected from among α-santalene, α-trans-bergamotene, epi-β-santalene, β-santalene, γ-curcumene, β-bisabolene, β-curcumene, α-curcumene, trans-trans-farnesol, α-pinene, camphene, limonene and α-terpinolene.

The terpene may preferably be selected from among (+)-epi-β-santalene, (−)-β-santalene, (+)-β-santalene, (+)-α-santalene, and (−)-α-santalene.

In a further aspect, two or more terpenes may be produced.

When the terpene is α-santalene, the amount of α-santalene produced is preferably at least or at least about 1%, 2%, 3%, 4%, 5%, 10%, 15%, 20%, 25%, 30%, 35%, 40%, 45%, 50%, 55%, 60%, 65%, 70%, 80% or more of the total amount of terpene(s) that is produced.

When the terpene is β-santalene, the amount of β-santalene produced is preferably at least or at least about 1%, 2%, 3%, 4%, 5%, 10%, 15%, 20%, 25%, 30%, 35%, 40%, 45%, 50%, 55%, 60%, 65%, 70%, 80% or more of the total amount of terpene(s) that is produced.

Most preferably, at least four terpenes are produced; the four terpenes include α-santalene, α-trans-bergamotene, epi-β-santalene and β-santalene; and α-santalene, α-trans-bergamotene, epi-β-santalene and β-santalene are produced with the following proportions relative to each other: α-santalene (38.0%), α-trans-bergamotene (12.1%), epi-β-santalene (4.7%) and β-santalene (45.2%). The terpenes so produced may be converted to an alcohol, for example an alcohol selected from among α-santalol, β-santalol, α-trans-bergamotol and epi-β-santalol. Such alcohols may, upon further processing, have the following proportions relative to each other: α-santalol (25-65%), α-trans-bergamotol (1-20%), epi-β-santalol (1-15%) and β-santalol (20-50%); or more preferably, α-santalol (59.28%), α-trans-bergamotol (7.32%), epi-β-santalol (3.45%) and β-santalol (29.0%).

In a further aspect, the present invention provides a recombinant host organism and/or cell transformed to harbour the nucleic acid of the invention. The host organism may be a unicellular or a multi-cellular organism, but is non-human. The host may, for example, be a cell of a multicellular organism. Preferably, the host organism heterologously comprises a nucleic acid of the invention. The host cells of the present invention may thus be prokaryotic, bacterial, or eukaryotic cells (e.g., yeast cells or plant cells).

As used herein, heterologous nucleic acid is nucleic acid that is not normally produced in vivo by the cell in which it is expressed, or that is normally produced by the cell but is at a different locus or expressed differently or that mediates or encodes mediators that alter expression of endogenous nucleic acid, such as DNA, by affecting transcription, translation, or other regulatable biochemical processes. Heterologous nucleic acid is generally not endogenous to the cell into which it is introduced, but has been obtained from another cell or prepared synthetically. Heterologous nucleic acid also can be endogenous, but is nucleic acid that is expressed from a different locus or altered in its expression. Generally, although not necessarily, such nucleic acid encodes RNA and proteins that are not normally produced by the cell or in the same way in the cell in which it is expressed. Heterologous nucleic acid, such as DNA, also can be referred to as foreign nucleic acid, such as DNA. Thus, heterologous nucleic acid or foreign nucleic acid includes a nucleic acid molecule not present in the exact orientation or position as the counterpart nucleic acid molecule, such as DNA, is found in a genome. It also can refer to a nucleic acid molecule from another organism or species (i.e., exogenous).

Heterologous expression refers to the expression in a host cell of a polypeptide encoded by heterologous nucleic acid that has been introduced, such as by transformation, electroporation, transduction, or any other means, into the host cell.

Preferably, the host organism is a bacterium, for example *E. coli*.

Further preferred host organisms include fungi, preferably yeasts, most preferably *Saccharomyces cerevisiae*. Other suitable host cells include the BTR yeast strain described in U.S. Pat. No. 6,531,303.

Suitable host organisms for expression of polypeptides of the invention may alternatively be a higher eukaryotic cell, preferably a plant or plant cell. Preferably, the plant is a species belonging to the family of the Solaniaceae or Lamiaceae, more preferably the genus of *Nicotiana*; or alternatively, a member of the genus *Catharanthus* such as *Catharanthus vinca*. The host organism may alternatively be a species of the *Santalum* genus, such as *S. album* or *S. spicatum*.

In an aspect, the present invention provides a recombinant host organism or cell expressing the polypeptide of the present invention. Preferably, the host organism is transformed to express the polypeptide in a higher quantity than in the same organism not so transformed.

The term "transformed" refers to the fact that the host was subjected to genetic engineering to comprise one, two, or more copies of any of the nucleic acids of the invention. Preferably, the host heterologously expresses the nucleic acids and/or polypeptides of the invention.

Accordingly, in an embodiment, the present invention provides a transformed organism in which the polypeptide of the invention is expressed in a higher quantity than in the same organism not so transformed.

There are several methods known in the art for the creation of transgenic, recombinant host organisms or cells such as plants, yeasts, bacteria, or cell cultures of higher eukaryotic organisms. For example, appropriate cloning and expression vectors for use with bacterial, fungal, yeast, and mammalian cellular hosts are described, for example, in Pouwels et al., "Cloning Vectors: A Laboratory Manual," Elsevier, New York (1985); and Sambrook et al., cited above. Cloning and expression vectors for higher plants and/or plant cells in particular are available to the skilled person (see, for example, Schardl et al., Gene 61:1-11 (1987)).

Methods for transforming host-organisms, for example, producing transgenic plants, modifying host organisms or cells to harbor transgenic nucleic acids, such as those of the present invention, are familiar to the skilled person. For the creation of transgenic plants, for example, current methods include: electroporation of plant protoplasts, liposome-mediated transformation, *agrobacterium*-mediated transformation, polyethylene-glycol-mediated transformation, particle bombardment, microinjection of plant cells, and transformation using viruses.

In one embodiment, transformed DNA is integrated into a chromosome of a non-human host organism and/or cell such that a stable recombinant system results. Any chromosomal integration method known in the art may be used in the practice of the invention, including, but not limited to, recombinase-mediated cassette exchange (RMCE), viral site-specific chromosomal insertion, adenovirus, homologous recombination by host-mediated processes and pronuclear injection.

The host cell of the present invention may preferably naturally produce the FPP substrate for the terpene synthase. Alternatively, the host cells can be engineered by, for example, transformation using a heterologous FPP gene, to produce FPP if they do not naturally produce such a compound. Further, host cells can be engineered to produce more FPP that they would naturally, thereby providing larger amounts of the substrate than the terpene synthase of the present invention uses (see, for example, U.S. Pat. No. 6,531,303 or WO 2009/109597).

It is anticipated that the sesquiterpene products of the enzymes of the present invention may be further processed by hydroxylation at the $C_{12}$ position to form santalols and bergamotols. For example, the α-santalene would be further processed to yield α-santalol, α-trans-bergamotene would yield α-trans-bergamotol, epi-β-santalene would yield epi-β-santalol and β-santalene would yield β-santalol. The SaSSy, SauSSy or SspiSSy terpene synthases of the present invention are preferably able to synthesise α-santalene, α-trans-bergamotene, epi-β-santalene and β-santalene in proportions relative to each other such that, on further processing of the compounds to the equivalent alcohols, the yield of santalols and bergamotols would be similar to that of the natural oil of, for example, *S. album* sandalwood.

Generally, sandalwood oil from *S. album* is composed of compounds as shown in Table 1, with the given proportions.

TABLE 1

Example of the composition of natural sandalwood oil (from *S. album*)

| Compound | % composition by GC |
|---|---|
| α-santalene | 1.26 |
| β-santalene | 0.22 |
| E-α-bergamotene | 1.28 |
| epi-β-santalene | 1.81 |
| γ-curcumene | 0.049 |
| β-bisabolene | 0.029 |
| β-curcumene | 0.226 |
| α-curcumene | 0.180 |
| α-bisabolol | 0.01 |
| Z-α-santalol | 51.48 |
| Z-α-trans-bergamotol | 6.36 |
| Z-epi-β-santalol | 3.80 |
| Z-β-santalol | 25.0 |
| E-β-santalol | 0.211 |
| Z-lanceol | 1.76 |
| Z-nuciferol | 1.30 |

It can be determined from Table 1 above that the proportions of α-santalol, α-trans-bergamotol, epi-β-santalol and β-santalol relative to each other (minus other oil components) are: α-santalol (59.28%), α-trans-bergamotol (7.32%), epi-β-santalol (4.35%) and β-santalol (29.0%).

The terpene synthases of the present invention preferably synthesize α-santalene, α-trans-bergamotene, epi-β-santalene and β-santalene such that, on further processing, the compounds yield the respective alcohols in the following proportions relative to each other: α-santalol (25-65%), α-trans-bergamotol (1-20%), epi-β-santalol (1-15%) and β-santalol (20-50%).

Most preferably, the terpene synthases of the present invention synthesise the sesquiterpene compounds such that, on further processing, the compounds yield the respective alcohols in the following relative proportions: α-santalol (34.7%), α-trans-bergamotol (11.1%), epi-β-santalol (4.3%) and β-santalol (41.3%). The remaining 8.6% of compounds are generally made up of a range of other compounds in small amounts. If the proportion of the other minor compounds is eliminated, the remaining four major compounds, on further processing to yield the respective alcohols, are preferably generated in the following proportions relative to each other: α-santalene (38.0%), α-trans-bergamotene (12.1%), epi-β-santalene (4.7%) and β-santalene (45.2%).

The relative proportions of the four major components in the oil produced using an isolated SaSSy terpene synthase and converted to the respective santalols was determined by both GC-MS and GC-FID. It is known that GC-MS tends to bias some compounds based on ease of ionization. However, both methods indicate that the relative composition of the products of the terpene synthases of the present invention are reflective of the composition of the respective alcohols in sandalwood oil (see Table 2).

TABLE 2

| Compound | Relative % composition in native oil (GC-MS) | Relative % composition in oil produced by SaSSy (GC-MS) | Relative % composition in oil produced by SaSSy (GC-FID) | Relative % composition in oil produced by SauSSy (GC-FID) | Relative % composition in oil produced by SspiSSy (GC-FID) |
| --- | --- | --- | --- | --- | --- |
| α-santalol | 59.28 | 38.0 | 45.3 | 51.3 | 47.3 |
| β-santalol | 29.0 | 45.2 | 31.5 | 27.4 | 26.3 |
| E-α-bergamotol | 7.32 | 12.1 | 16.0 | 14.5 | 19.2 |
| epi-β-santalol | 4.35 | 4.7 | 4.7 | 4.8 | 4.2 |

The further processing may be carried out by any means known to the skilled person, such as use of an appropriate cytochrome P450 enzyme, or chemical reactions such as alkaline metalation, borylation and oxidation, to yield the correct cis alcohols. Cytochrome P450 technology is established for other sesquiterpenoids, most notably artemisinin production.

The nucleic acid probes of the present invention may be used to select suitable trees for breeding programs or strain improvement programs in relation to S. album or other members of the Santalum genus. It is known that not all S. austrocaledonicum, S. spicatum and S. album trees produce sandalwood oil in equivalent quantities, and the relative proportion of terpenes in the oil may be the subject of variation between trees, particularly in relation to the control, expression transcription and/or translation of the nucleic acids of the SaSSy, SauSSy or SspiSSy genes.

Therefore, the nucleic acid probes of the present invention may be used to determine which trees of a given set are expressing SaSSy, SauSSy or SspiSSy genes at high levels, using methods described herein and/or those well known to the skilled addressee. Alternatively, the level of expression of SaSSy, SauSSy or SspiSSy amino acids may be determined to assess which trees are producing large amounts of desirable terpenes. Preferably, probes may be used to detect trees that express a gene for a terpene synthase that produces one or more of the following terpenes: α-santalene, α-trans-bergamotene, epi-β-santalene, β-santalene and trans-trans-farnesol.

Alternatively, the polypeptides or polypeptide fragments of the present invention may be used to generate antibodies against specific regions of the SaSSy, SauSSy or SspiSSy genes. These antibodies may then be used to screen samples from trees to determine which trees are expressing the synthase genes, and the level of that expression. Again, such methods of detection may be used to select trees that produce large amounts of desirable terpenes, or desirable proportions of different terpenes.

The invention thus provides a method for detecting the presence of a terpene synthase in a sample, comprising the steps of:

(a) contacting a sample suspected of containing terpene synthase of the invention with an antibody that specifically binds to the terpene synthase under conditions which allow for the formation of reaction complexes comprising the antibody and the terpene synthase; and (b) detecting the formation of reaction complexes comprising the antibody and the terpene synthase in the sample, wherein detection of the formation of reaction complexes indicates the presence of the terpene synthase amino acid sequence in the sample.

The method may comprise the further step of evaluating the amount of reaction complexes formed, thereby determining the amount of terpene synthase in the biological sample.

Preferably, the antibody used in these methods is derived from an affinity-purified polyclonal antibody, and more preferably a mAb. In addition, it is preferable that the antibody molecules used herein be in the form of Fab, Fab', F(ab')$_2$ or F(v) portions or whole antibody molecules.

Particularly preferred methods for detecting the terpene synthase genes of the invention based on the above methods include enzyme-linked immunosorbent assays, radioimmunoassays, immunoradiometric assays and immunoenzymatic assays, including competitive and sandwich assays using monoclonal and/or polyclonal antibodies.

In each instance, the amino acid sequences of the present invention form complexes with one or more antibody(ies) or binding partners and one member of the complex is labelled with a detectable label. The fact that a complex has formed and, if desired, the amount thereof, can be determined by known methods applicable to the detection of labels.

The labels most commonly employed for these studies are radioactive elements, enzymes, chemicals that fluoresce when exposed to ultraviolet light, and others.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The SaSSy, SauSSy or SspiSSy amino acid sequences or their binding partners can also be labelled with a radioactive element or with an enzyme. The radioactive label can be detected by any of the currently available counting procedures.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred enzymes are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labelling material and methods.

Other preferred methods for detecting the terpene synthase genes and proteins of the invention based on the above methods include selective reaction monitoring or multiple reaction monitoring, as discussed in Zulak, K. G., Lippert, D. N., Kuzyk, M., Domanski, D., Chou, T., Borchers, C. H. and J. Bohlmann, "Targeted proteomics using selected reaction monitoring (SRM) reveals the induction of specific terpene synthases in a multi-level study of methyl jasmonate treated Norway spruce (Picea abies)," The Plant Journal 60:1015-1030 (2009).

The present invention further provides methods for detecting the presence of a terpene synthase nucleic acid molecule in a biological sample, which comprise the steps of:

(a) bringing the biological sample into contact with a polynucleotide probe or primer comprising a terpene synthase polynucleotide of the invention under suitable hybridising conditions; and (b) detecting any duplex formed between the probe or primer and nucleic acid sequences in the sample.

According to one embodiment of the invention, detection of the SaSSy, SauSSy or SspiSSy genes may be accomplished by directly amplifying the terpene synthase polynucleotide sequences from a biological sample, using known techniques, and then detecting the presence of the SaSSy, SauSSy or SspiSSy polynucleotide sequences.

The present invention thus also relates to a method for the detection of a terpene synthase in a biological sample, comprising:

(a) amplifying the nucleic acid molecule with at least one primer or oligonucleotide as defined above; and (b) detecting the amplified nucleic acid molecules.

Preferably, the nucleic acid is extracted and/or purified (e.g., from a tissue sample) prior to amplification.

The present invention also relates to a method for the detection of SaSSy, SauSSy or SspiSSy nucleic acids present in a biological sample, comprising:

(a) hybridizing the nucleic acids of the biological sample at appropriate conditions with one or more probes as defined above;

(b) washing under appropriate conditions; and (c) detecting the hybrids formed.

Preferably, the hybridizing conditions are denatured conditions.

Preferably, the nucleic acid is extracted and/or purified (e.g., from a tissue sample) prior to hybridisation. More preferably, the nucleic acid sample is amplified with at least one primer as defined above, after extraction or at least prior to hybridisation. Preferably, said probes are attached to a solid substrate or detected in a liquid phase by photometric or fluorogenic detection or by other methods of visualisation such as by agarose gel electrophoresis.

The present invention also relates to a method as defined above, wherein said nucleic acids are labelled during or after amplification.

Suitable assay methods for purposes of the present invention to detect hybrids formed between the oligonucleotide probes and the nucleic acid sequences in a sample may comprise any of the assay formats known in the art, such as the conventional dot-blot format, sandwich hybridization or reverse hybridization. For example, the detection can be accomplished using a dot blot format, the unlabelled amplified sample being bound to a membrane, the membrane being incorporated with at least one labelled probe under suitable hybridization and wash conditions, and the presence of bound probe being monitored.

An alternative and preferred method is a "reverse" dot-blot format, in which the amplified sequence contains a label. In this format, the unlabelled oligonucleotide probes are bound to a solid support and exposed to the labelled sample under appropriate stringent hybridization and subsequent washing conditions. It is to be understood that also any other assay method which relies on the formation of a hybrid between the nucleic acids of the sample and the oligonucleotide probes according to the present invention may be used.

In one form of the invention, the target nucleic acid sequence is amplified by PCR and then detected using any of the specific methods mentioned above. Other useful diagnostic techniques for detecting the presence of SaSSy, SauSSy or SspiSSy polynucleotide sequences include, but are not limited to: 1) allele-specific PCR; 2) single stranded conformation analysis; 3) denaturing gradient gel electrophoresis; 4) RNase protection assays; 5) the use of proteins which recognize nucleotide mismatches, such as the $E.\ coli$ mutS protein; 6) allele-specific oligonucleotides; and 7) fluorescent in situ hybridisation.

In addition to the above methods, SaSSy, SauSSy or SspiSSy polynucleotide sequences may be detected using conventional probe technology. When probes are used to detect the presence of the SaSSy, SauSSy or SspiSSy polynucleotide sequences, the biological sample to be analysed, such as woody tissue particularly heartwood tissue, may be treated, if desired, to extract the nucleic acids. The sample polynucleotide sequences may be prepared in various ways to facilitate detection of the target sequence, e.g., denaturation, restriction digestion, electrophoresis or dot blotting. The targeted region of the sample polynucleotide sequence usually must be at least partially single-stranded to form hybrids with the targeting sequence of the probe. Denaturation of the target sequence will probably be required and can be carried out by various techniques known in the art.

Sample polynucleotide sequences and probes are incubated under conditions that promote stable hybrid formation of the target sequence in the probe with the putative SaSSy, SauSSy or SspiSSy polynucleotide sequence in the sample. Preferably, high stringency conditions are used in order to prevent false positives.

Detection, if any, of the resulting hybrid is usually accomplished by the use of labelled probes. Alternatively, the probe may be unlabelled, but may be detectable by specific binding with a ligand that is labelled, either directly or indirectly. Suitable labels and methods for labelling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labelled moiety.

Preferably, the probe is labelled. More preferably, the probe is radiolabelled or fluorescent- or enzyme-labelled.

Once suitable trees have been identified, they may be used in selective breeding programs, or simply identified as trees which may be harvested for sandalwood oil production.

In a still further aspect, the present invention provides processes and/or methods for making terpenoids.

Accordingly, the present invention provides a method of making at least one terpenoid comprising:

(a) contacting at least one acyclic pyrophosphate terpene precursor with at least one polypeptide of the invention or encoded by any of the nucleic acids of the invention; and (b) optionally, isolating at least one terpenoid produced in step (a).

Furthermore, the present invention provides a method of making at least one terpenoid comprising:

(a) cultivating a non-human organism transformed to express or increasingly express a polypeptide of the invention under conditions conducive to the production of terpenoids; and (b) optionally, isolating at least one terpenoid from the non-human organism.

According to a preferred embodiment, the method further comprises the step of: transforming a non-human organism with a recombinant nucleic acid to express or increasingly express a polypeptide of the invention, before step (a).

Preferably, the at least one terpenoid is selected from the following: α-santalene, α-trans-bergamotene, epi-β-santalene and β-santalene.

The method of making at least one terpenoid comprises the step of contacting at least one acyclic pyrophosphate terpene precursor with at least one polypeptide of the invention. For example, polypeptides as obtained in the above methods for producing terpene synthases may be used. Such polypeptides may be extracted from host organisms expressing the nucleic acids of the invention according to standard protein or enzyme extraction technologies. If the host organism is a unicellular organism or cell releasing the polypeptide of the invention into the culture medium, the polypeptide may be collected from the culture medium, for example, by centrifugation, optionally followed by washing steps and resuspension in suitable buffer solutions.

If the host organism is a plant or a unicellular organism or cell accumulating the polypeptide of the invention within the cell, the polypeptide may be obtained by disruption or lysis of the cells and extracting the polypeptide from the cell lysate.

The isolated polypeptide may then be suspended in a buffer solution at optimal pH and temperature. If adequate, salts, BSA and other kinds of enzymatic co-factors may be added in order to optimize enzyme activity.

The terpene precursor may be added to a polypeptide suspension or solution, followed by incubation at optimal temperature, for example 300° C. After incubation, the terpenoid compound may be isolated from the incubated solution by standard isolation procedures, such as solvent extraction and distillation, preferably after removal of polypeptides from the solution.

In a step of the process for making at least one terpenoid compound, the host organism or cell is cultivated under conditions conducive to the production of terpenoids. Accordingly, if the host is a transgenic plant, optimal growing conditions are provided, such as optimal light, water and nutrient conditions, for example. If the host is a unicellular organism, conditions conducive to the production of the terpenoid may comprise addition of suitable cofactors to the culture medium of the host. In addition, a culture medium may be selected which proves to maximize terpenoid synthesis. External factors such as optimized pH and temperature are usually also conducive to terpenoid production in a given expression system.

Other factors such as elicitors can also be used to upregulate transcription of certain genes, in particular terpenes, which can be associated with plant defense mechanisms. Elicitors may therefore be used to upregulate the transcription of the terpene synthase gene of the present invention, in sandalwood or other host organisms, including hosts trees. A range of elicitors are well known to those skilled in the art and can be readily purchased. Preferably, the elicitor chosen is one that upregulates the expression of the terpene synthase gene of the present invention in the specific environment in which the gene is provided. Examples of suitable elicitors include methyl jasmonate and salicylic acid. The terpene synthase gene may further provide a means to assess whether upregulation of transcription has occurred following treatment of, for example, a sandalwood tree, with elicitors. Such assessment may further include the measurement of oil levels in such trees to determine if the elicitor applied has an upregulating effect.

In a further embodiment of this invention, kits may be prepared to determine the presence or absence of a SaSSy, SauSSy or SspiSSy gene in sandalwood trees and/or the activity of the gene.

In accordance with the testing techniques discussed above, one class of such kits for the detection of the SaSSy, SauSSy or SspiSSy proteins will contain at least a labelled SaSSy, SauSSy or SspiSSy amino acid sequence binding partner, for instance an antibody specific thereto, and directions depending upon the method selected, e.g., "competitive," "sandwich," "DASP," and the like. The kits may also contain peripheral reagents such as buffers, stabilizers, etc.

Accordingly, a test kit may be prepared for the demonstration of the presence of the SaSSy, SauSSy or SspiSSy enzymes comprising:

(a) a predetermined amount of at least one labelled immunochemically reactive component obtained by the direct or indirect attachment of a SaSSy, SauSSy and SspiSSy amino acid sequence specific binding partner to a detectable label;

(b) other reagents; and (c) directions for use of said kit.

The labelled binding partner (such as an antibody) may be generally bound to a solid phase.

The invention also provides kits for detecting SaSSy, SauSSy or SspiSSy nucleic acid sequences.

Accordingly, the invention provides a kit for demonstrating the presence of SaSSy, SauSSy or SspiSSy nucleic acid sequences comprising:

(a) a predetermined amount of at least one labelled nucleic acid sequence derived from the SaSSy, SauSSy or SspiSSy gene sequence;

(b) other reagents; and (c) directions for use of said kit.

For example, the polynucleotide sequence may be one or more primers, such as those exemplified above, and the instructions for use may be instructions to perform PCR on RNA or DNA extracted from a tissue sample from a subject.

In another aspect, the invention provides a kit for demonstrating the presence of a terpene synthase comprising:

(a) a predetermined amount of at least one ligand that binds to the terpene synthase of the present invention, wherein the ligand comprises a detectable label;

(b) other reagents; and (c) directions for use of said kit.

In a further aspect there is provided a kit for demonstrating the presence of nucleic acid molecules encoding a terpene synthase, comprising:

(a) a predetermined amount of at least one labelled nucleic acid molecule or primer of the present invention;

(b) other reagents; and (c) directions for use of said kit.

The above kits may use samples from a sandalwood tree. The method may be performed on at least two samples from two different sandalwood trees; and the amount of terpene synthase or nucleic acid encoding terpene synthase in each sample is determined; then the sandalwood tree from which the sample with the most amount of a terpene synthase or a nucleic acid encoding a terpene synthase was derived, is selected; and the selected sandalwood tree is selectively bred or harvested for sandalwood oil.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

As used herein, the terms "derived" and "derived from" shall be taken to indicate that a specific integer may be obtained from a particular source, albeit not necessarily directly from that source.

As used herein, the singular forms "a," "an" and "the" include plural references unless the context clearly dictates otherwise. Thus, for example, reference to a terpene synthase that catalyzes the formation of a terpene includes synthases that catalyze the productions of one or a plurality of terpenes.

Throughout this specification, unless the context requires otherwise, the word "comprise," or variations such as "comprises" or "comprising," will be understood to imply the inclusion of a stated integer or group of integers, but not the exclusion of any other integer or group of integers.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. Hence "about 80%" means "about 80%" and also "80%." At the very least, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

The following examples serve to more fully describe the manner of using the above-described invention, as well as to set forth the best modes contemplated for carrying out various aspects of the invention. It is understood that these methods in no way serve to limit the true scope of this invention, but rather are presented for illustrative purposes.

EXAMPLES

All reagents, solvents, antibiotics and precursor chemicals were purchased from commercial sources. Farnesyl diphosphate and geranyl diphosphate were from Sigma (St. Louis, Mo., USA). Restriction endonucleases and T4 DNA ligase were from New England Biolabs (Ipswich, Mass.).

Example 1

Plant Material Collection and RNA Extraction

Several holes were drilled into one mature *Santalum album* tree growing in the FPC Kununurra arboretum, Kununurra, Wash. Wood shavings from the transition zone of the xylem were collected and frozen immediately in liquid nitrogen and transported to UWA, Perth.

RNA was extracted using a modified protocol (Kolosova, N., et al., "Isolation of high-quality RNA from gymnosperm and angiosperm trees," BioTechniques 36:821-824 (2004)). Wood shavings (50 g) were ground in liquid nitrogen and added to RNA extraction buffer (200 mM Tris-HCl, pH 8.5, 1.5% lithium dodecyl sulphate, 300 mM LiCl, 10 mM EDTA, 1% w/v sodium deoxycholate, 1% w/v Tergitol Nonidet® P-40). 5 mM thiourea, 1 mM aurintricarboxylic acid, 10 mM dithiothreitol, and 2% (w/v) polyvinylpolypyrrolidone (PVPP) were added just prior to use. All solutions were prepared from DEPC treated and/or autoclaved water. Several tubes were combined at the TE/NaCl resuspension step to concentrate the RNA sample. After precipitation, RNA was stored at −80° C. until transported to UBC Vancouver, Canada for cDNA library construction.

Example 2 cDNA Synthesis and Library Construction 1.4 μg of *S. album* xylem total RNA was reverse transcribed with SuperScript III reverse transcriptase (Invitrogen) at 42° C. for 1 hour using the Clontech oligo dT primer and SMART 5' oligo. cDNA was amplified using the M1 primer supplied in the kit.

The amplified cDNA was then digested with Sfi1 restriction enzyme (New England Biolabs). The resulting mixture was passed through a Chromaspin size exclusion column, eluting the largest sized fragments first. cDNA was collected in 200 mL aliquots and those which had the desired high molecular weight range were combined and eluted on a Qiagen MinElute spin column.

The digested cDNA fragments were then cloned into pre-cut pDNR-LIB vector and transformed by electroporation into 25 μL of phage resistant electrocompetent *E. coli* cells. The cells were shaken at 37° C. for 1 h in SOC media before being mixed with glycerol and stored at −80° C. Aliquots were plated onto agar containing chloramphenicol at 30 mg/mL. cDNA library was titrated to approximately 3×10⁶ colony forming units per mL. The library was sent to the Genome Sciences Centre, Vancouver Canada for 5' and 3' sequencing.

Example 3

Identification of Terpene Synthase Genes from an *S. album* Xylem EST Library

Reads were assembled using the CAP3 program with default settings. The EST library was compared by BLAST searching to the NCBI database for genes homologous to previously published terpene synthase (TPS) and cytochrome P450 gene sequences. Several candidate genes were identified, including one full length gene with modest identity to limonene synthase from *Ricinus communis* and linalool synthase *Backhousia citriodora*. About 12 putative cytochrome P450 oxidase enzymes were also discovered, some of which were full length.

Example 4

Bacterial Expression

Colonies producing a positive hit to known terpene synthase (TPS) genes were plasmid purified to yield pDNR-LIB bound full length cDNAs. One gene, labelled SaSSy, was selected. Alignment of the deduced amino acid sequence of SaSSy with other angiosperm genes are shown in FIG. 6 and alignment of the deduced amino acid sequence of SaSSy, SauSSy and SspiSSy with other angiosperm terpene synthase genes are shown in FIG. 12.

Two versions of the SaSSy gene were located, differing only at position 143, with clone P143 having a proline residue at position 143 and clone S143 having a serine residue at that location. The two proteins produced from these clones were later found to have identical activity, indicating that switching one polar residue with another at position 143 has little to no effect on catalysis.

SaSSy features motifs typical of the monoterpene synthase gene TPS-b subfamily (Bohlmann, J., et al., "Plant terpenoid synthases: molecular biology and phylogenetic analysis," Proc. Natl. Acad. Sci. U.S.A. 95:4126-4133 (1998)), including the aspartate-rich DDxxD metal ion binding site (positions 321-325) and the $RRX_8W$ motif (positions 32-42), which is implicated in diphosphate group migration (Williams, D. C., et al., "Truncation of limonene synthase preprotein provides a fully active 'pseudomature' form of this monoterpene cyclase and reveals the function of the aminoterminal arginine pair," Biochem. 37:12213-12220 (1998)).

The two full length SaSSy gene sequences located above in Example 4 (P143 and S143) were cloned into pET28b (+) expression vectors (Novagen, San Diego, Calif.) with a C-terminal histidine tag. The vectors were cut with NcoI and XhoI, to create overhangs suitable for ligation into similarly digested cDNA. The circular plasmids, which contained the sesquiterpene synthase gene in frame with a Ni-affinity tag ($His_6$) were first transformed into chemically competent cells and grown on LB plates with kanamycin (50 μg/mL).

Transformants were grown on selective LB plates (kanamycin 50 μg/mL), and the DNA extracted via plasmid preparation (Invitrogen). pET28b (+) vectors containing the insert were sequence verified and transformed into chemically competent C41 *E. coli* cells (Avidis, Saint-Beauzire, France) containing the pRARE 2 plasmid isolated from Rosetta 2 competent cells (Novagen). Colonies were grown on LB plates containing kanamycin and chloramphenicol (50 μg/mL).

Independent colonies were picked and grown in a shaker overnight at 37° C. in 5 mL of LB with the same antibiotics. 2 mL of this culture was added to 4 lots of 100 mL of TB containing kanamycin and chloramphenicol. The cell suspension was grown for 4 hours with shaking at 37° C. until the $OD_{600}$=0.8. Isopropyl-β-D-thiogalacto-pyranoside (IPTG) was added to a final concentration of 0.2 mM and the mixture was shaken overnight at 16° C. Cell suspension was harvested by centrifugation at 4° C. and the cell pellet frozen at −80° C. for future use.

Cell pellets (~7 g) were resuspended in 5 mL of lysis buffer (25 mg lysozyme, 0.25 mg DNAse, 0.25 mg RNAse, 19.3 mg DTT, 5 μL protease inhibitor cocktail [PMSF and thiourea] and 250 μL of 100 mM $MgCl_2$). While on ice, the mixture was stirred thoroughly with a glass rod for 30 min. Lysate was then sonicated on ice using a Bronson ultrasonic probe until translucent. The mixture was centrifuged at 20,000×g at 4° C. for 30 min. Supernatant was decanted and stored on ice.

Example 5

Protein Purification

The cleared lysate supernatant (~3 mL) was sequentially loaded onto HisTrap Spin columns (GE Healthcare) and spun at 1000 rpm for 2 min at 4° C. After washing with fresh binding buffer the protein was eluted twice with 300 μL of elution buffer (20 mM HEPES pH 7.5, 150 mM NaCl and 350 mM imidazole) to a final volume of 600 μL.

The eluates from each of the two SaSSy terpene synthase variants (P143 and S143) solutions were desalted on a 2 mL sephadex desalting column (BioRad, Hercules Calif., USA) into elution buffer which lacked imidazole.

The eluent was analysed by spectrophotometry to determine approximate protein concentrations. Final concentration was ~8 mg/mL. These solutions were used for assays. Aliquots of the purified proteins were mixed with 80% glycerol (1:1) and frozen in liquid $N_2$. These were stored at −80° C. until use. Proteins were analysed using SDS-PAGE, western blotting and immunolabelling with $His_6$ antibody (Sigma). Antibody was visualised by the NBT/BCIP assay (Roche, USA). The recombinant protein for each of P143 and S143 was confirmed to be of the expected size of ~66 kDa.

Example 6

Enzyme Assays

Enzyme assays for both recombinant isoenzyme proteins P143 and S143 were done in duplicate using GC vials as per O'Maille, P. E., et al. ("A single-vial analytical and quantitative gas chromatography-mass spectrometry assay for terpene synthases," Anal. Biochem. 335:210-217 (2004)). For each assay, 20 μL of protein (8 mg/mL) was added to 450 μL of reaction buffer containing 25 mM HEPES, 10% glycerol, 5 mM DTT and 10 mM of $Mg^{2+}$. 20 μL of substrates FPP and GPP (~1 mg/mL) were added and the mixture gently shaken. Final enzyme concentration was 0.3 mg/mL. Vials were overlaid with 500 μL of pentane to trap volatile products and incubated at 30° C. for 2 h.

Example 7

GC-MS Analysis and Product Identification

The product mixture of the SaSSy enzyme was analysed on an Agilent 6890 GC with a 5973 MSD using helium as carrier gas. Peak identification was done using an HP5-MS capillary column (30 m, 0.25 mm ID, 0.25 mm film thickness). Injector temperature was 240° C., detector temperature was set at 250° C., injection volume was 1 μL and column flow rate was 1 mL/min. Oven temperature program was as follows: oven program was held for 1 min at 40° C., then ramped at 7.5° C./min to 250° C. and held. All mass spectra were detected at 70 eV in multiple ion scan mode.

The identities of products from SaSSy incubations were confirmed by comparison of mass spectra retention times to authentic sandalwood oil in the NIST 2005 library, see publications by Adams, R. P. ("Identification of essential oil components by gas chromatography/mass spectrometry," Allured Publishing Corporation, Carol Stream, Ill. (1995)) and MassFinder (www.massfinder.com).

Enzyme assays using recombinant SaSSy enzyme with GPP as substrate in the presence of $Mn^{2+}$ produced a mixture of α-pinene, camphene, limonene and α-terpinolene, along with other monoterpene products as determined by GC-MS.

Figure 2A:
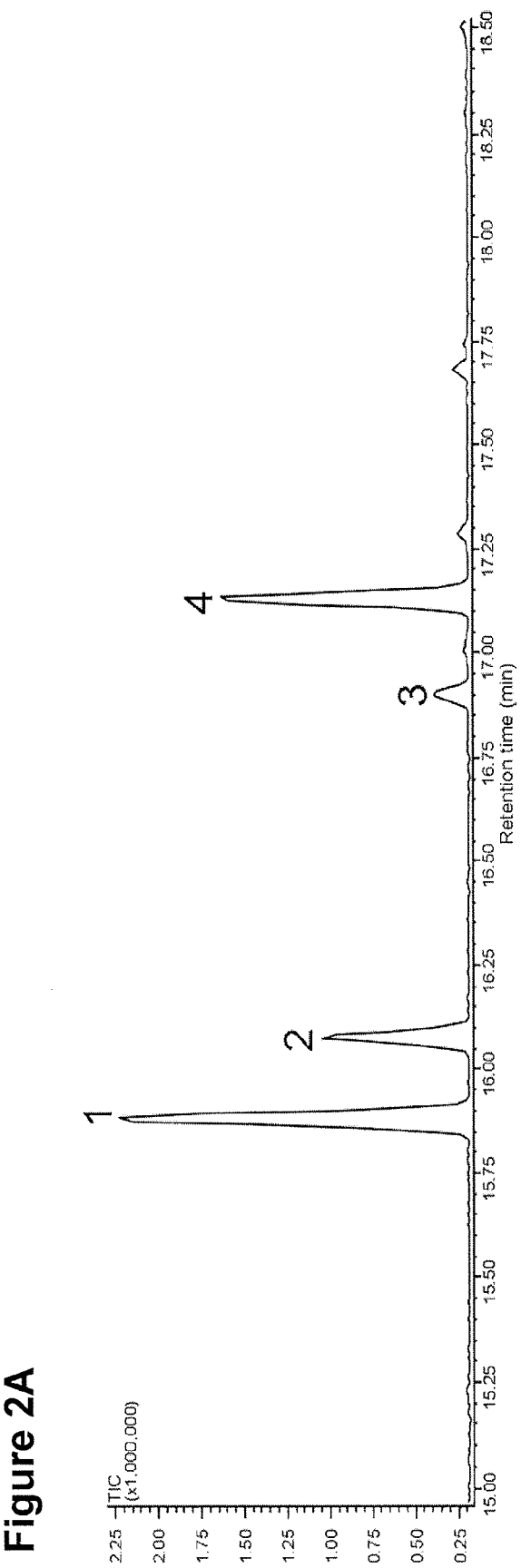
FIGS. 2A and 2B: GC trace of SaSSy product profile after incubation with FPP, with mass spectrum data for α-santalene, α-trans-bergamotene, epi-β-santalene and β-santalene from the SaSSy product profile after incubation with FPP as detected by GC-MS.
Figure 2B:
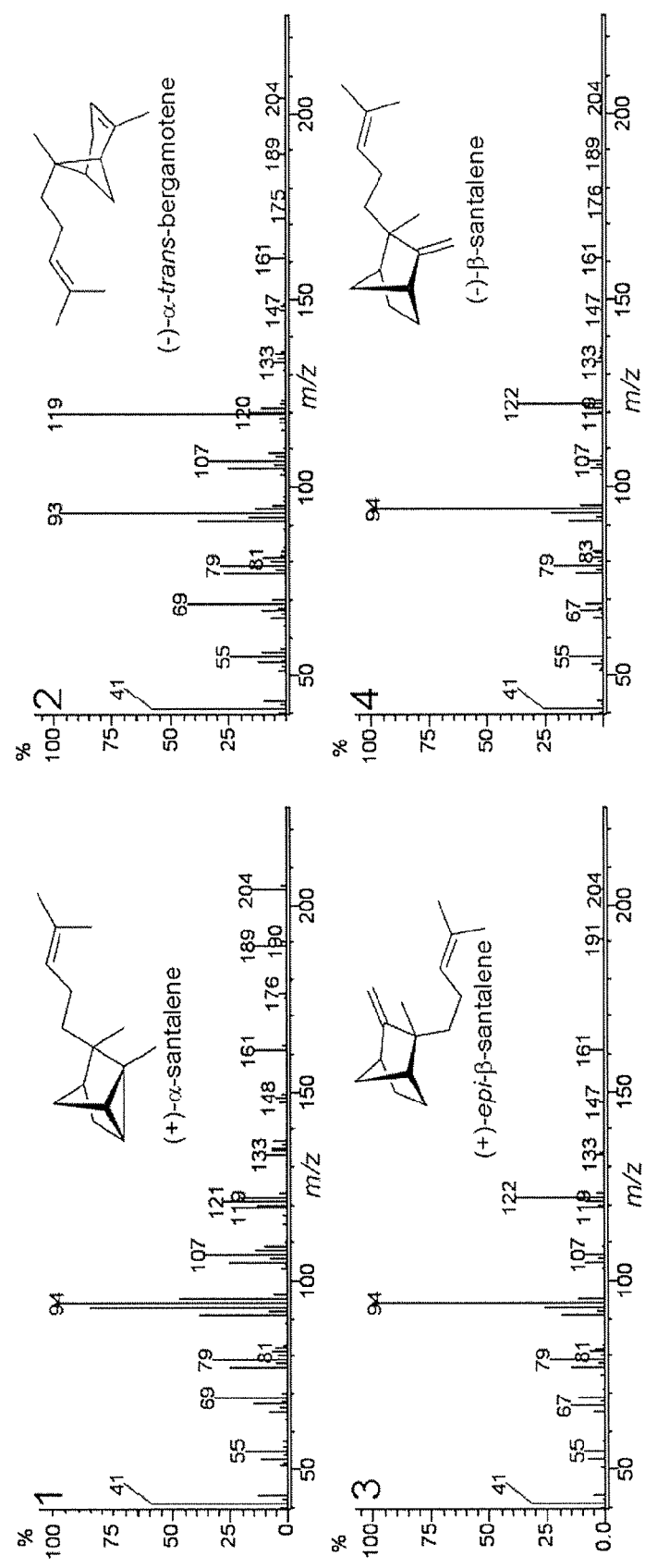
Figure 3A:
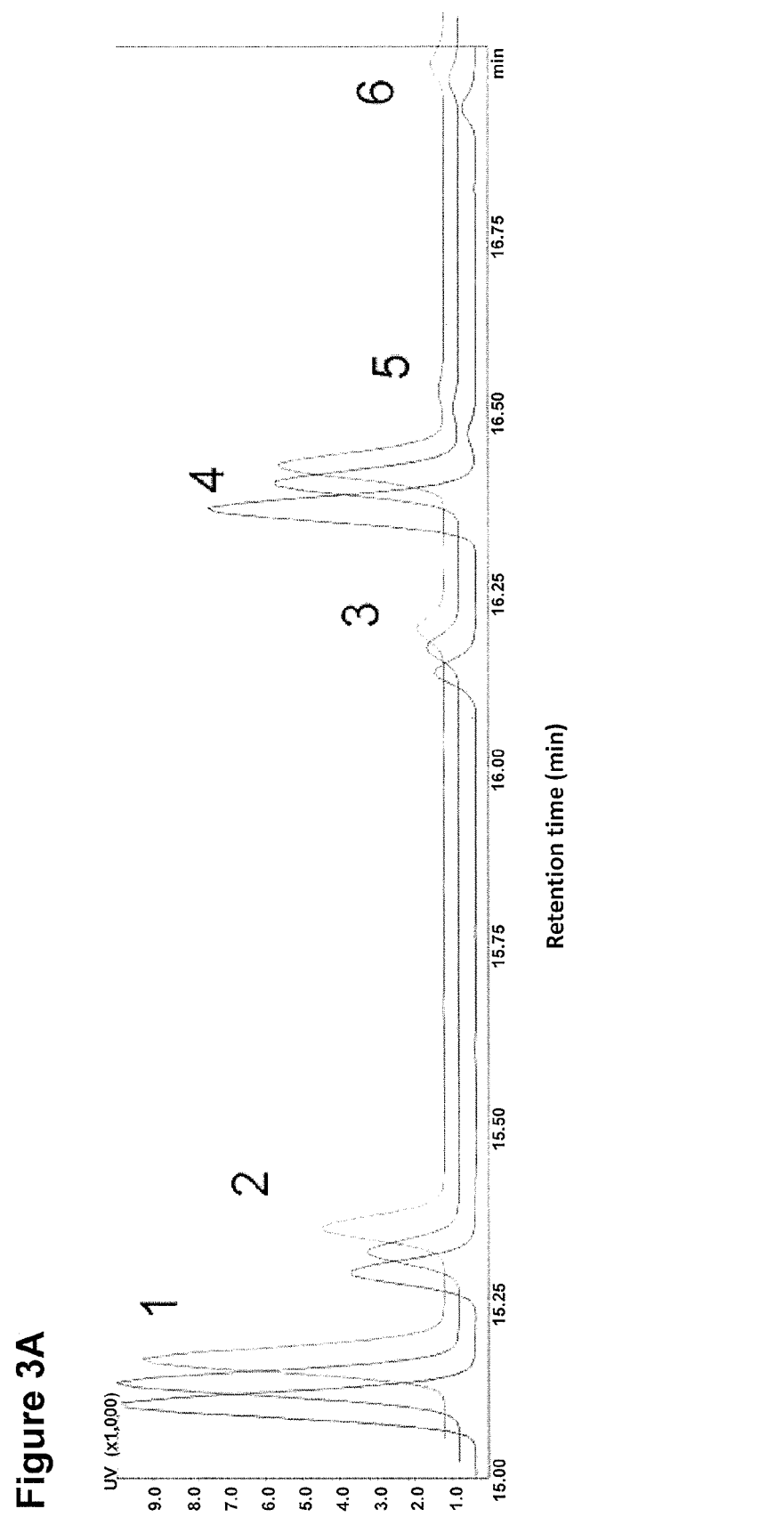
FIGS. 3A and 3B: Superposed GC traces of SaSSY, SauSSy and SspiSSy product profiles after incubation with FPP, with mass spectrum data for α-santalene, α-trans-bergamotene, epi-β-santalene, β-santalene, cis-β-farnesene and trans-β-farnesene from the SaSSy product profile after incubation with FPP as detected by GC-MS.
Figure 3B:
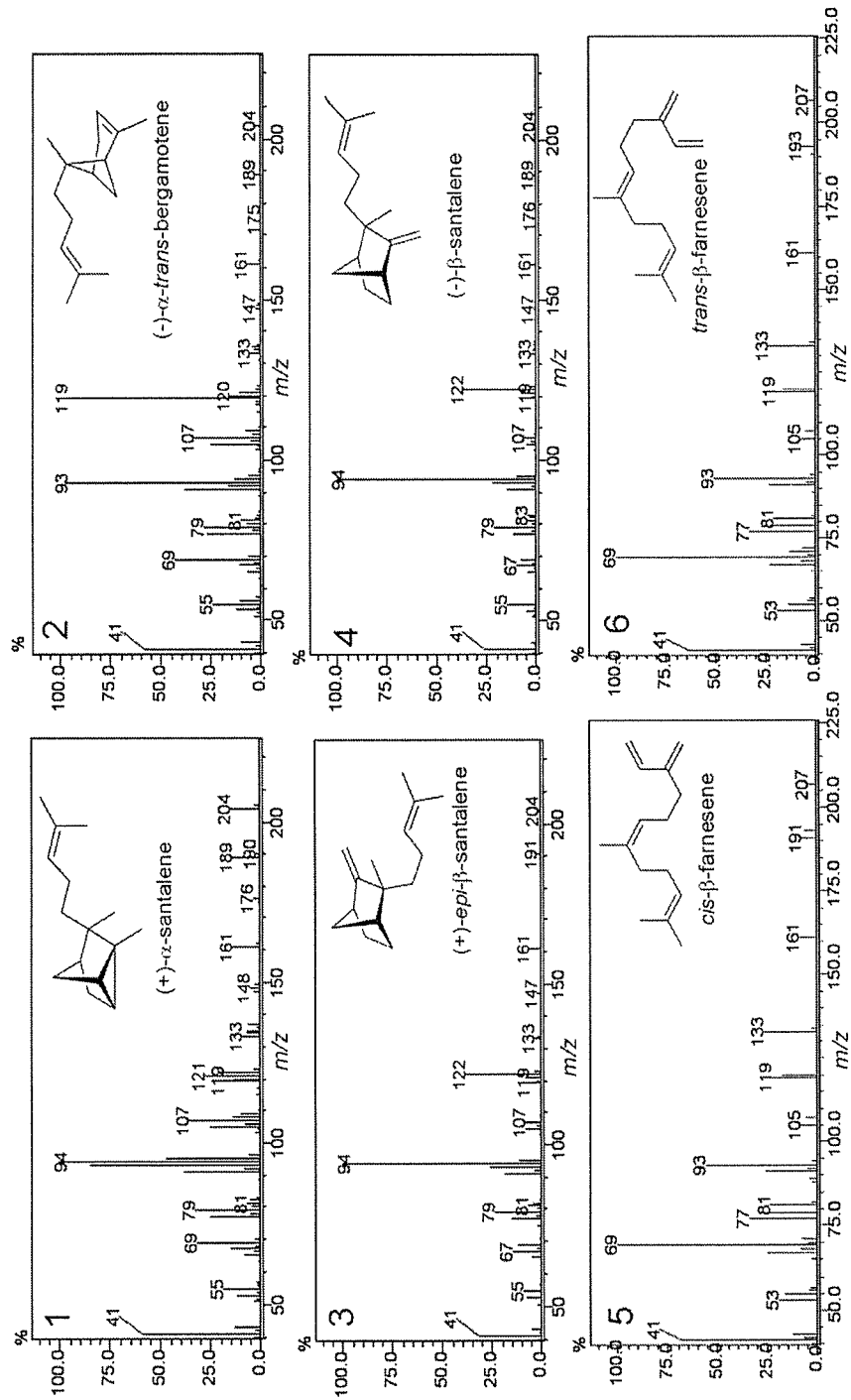
Figure 7:
FIG. 7: Phylogenetic tree of proteins aligned in FIG. 6.
Figure 8:
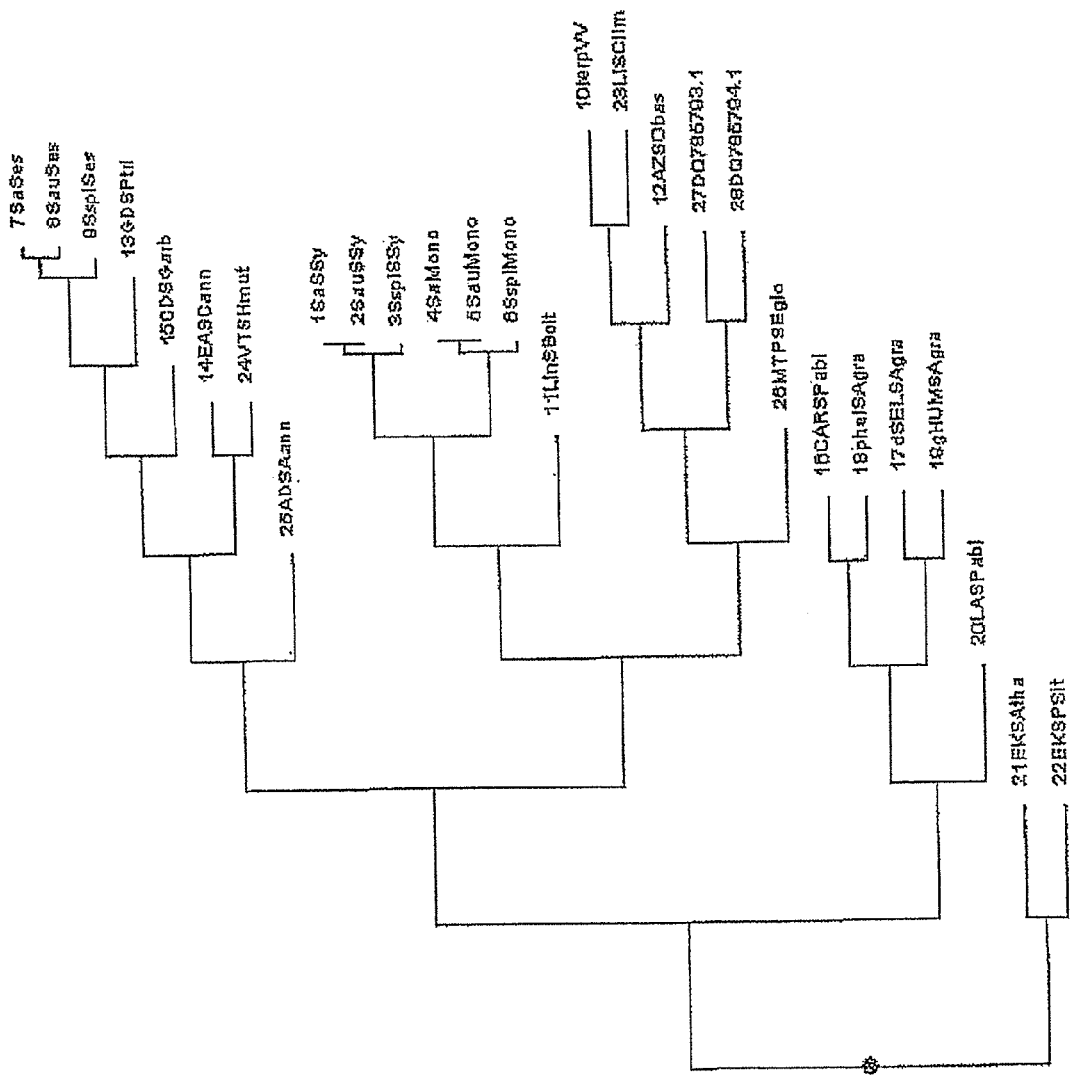
FIG. 8: UPGMA alignment tree of 28 different terpene synthase genes. Reference codes as follows: 1 SaSSy [*Santalum album*]; 2 SauSSy [*Santalum austrocaledonicum*]; 3 SspiSSy [*Santalum spicatum*]; 4 ACF24767.1 monoterpene synthase [*Santalum album*]; 5 SauMonoTPS1 [*Santalum austrocaledonicum*]; 6 SspiMonoTPS1 [*Santalum spicatum*]; 7 ACF24768.1 SaSesquiTPS1 [*Santalum album*]; 8 SausSesquiTPS1 [*Santalum austrocaledonicum*]; 9 SspiSesquiTPS1 [*Santalum spicatum*]; 10 AAS79351.1 (−)-a-terpineol synthase [*Vitis vinifera*]; 11 BAG82825.1 linalool synthase [*Backhousia citriodora*]; 12 AAV63788.1 alpha-zingiberene synthase [*Ocimum basilicum*]; 13 AAR99061.1 (−)-germacrene D synthase [*Populus trichocarpa×Populus deltoides*]; 14 CAA06614.1 5-epi-aristolochene synthase [*Capsicum annuum* var. *annuum*]; 15 CAA77191.1 (+)-delta-cadinene synthase [*Gossypium arboreum*]; 16 AA073863.1 (+)-3-carene synthase [*Picea abies*]; 17 AACO5727.1 d-selinene synthase [*Abies grandis*]; 18 AAF61453.1 beta-phellandrene synthase [*Abies grandis*]; 19 AACO5728.1 gamma-humulene synthase [*Abies grandis*]; 20 AAS47691.1 LAS [*Picea abies*]; 21 AAC39443.1 ent-kaurene synthase [*Arabidopsis thaliana*]; 22 ADB55710.1 (−)-ent-kaurene synthase [*Picea sitchensis*]; 23 AAM53944.1AF514287__1 (+)-limonene synthase 1 [*Citrus limon*]; 24 AAA86337.1 vetispiradiene synthase [*Hyoscyamus muticus*]; 25 AAF61439.1 amorpha-4,11-diene synthase [*Artemisia annua*]; 26 BAF02832.1 monoterpene synthase [*Eucalyptus globulus*]; 27 Cineole synthase [*Salvia fruticosa*]; 28 Sabinene synthase [*Salvia pomifera*].
Figure 9:
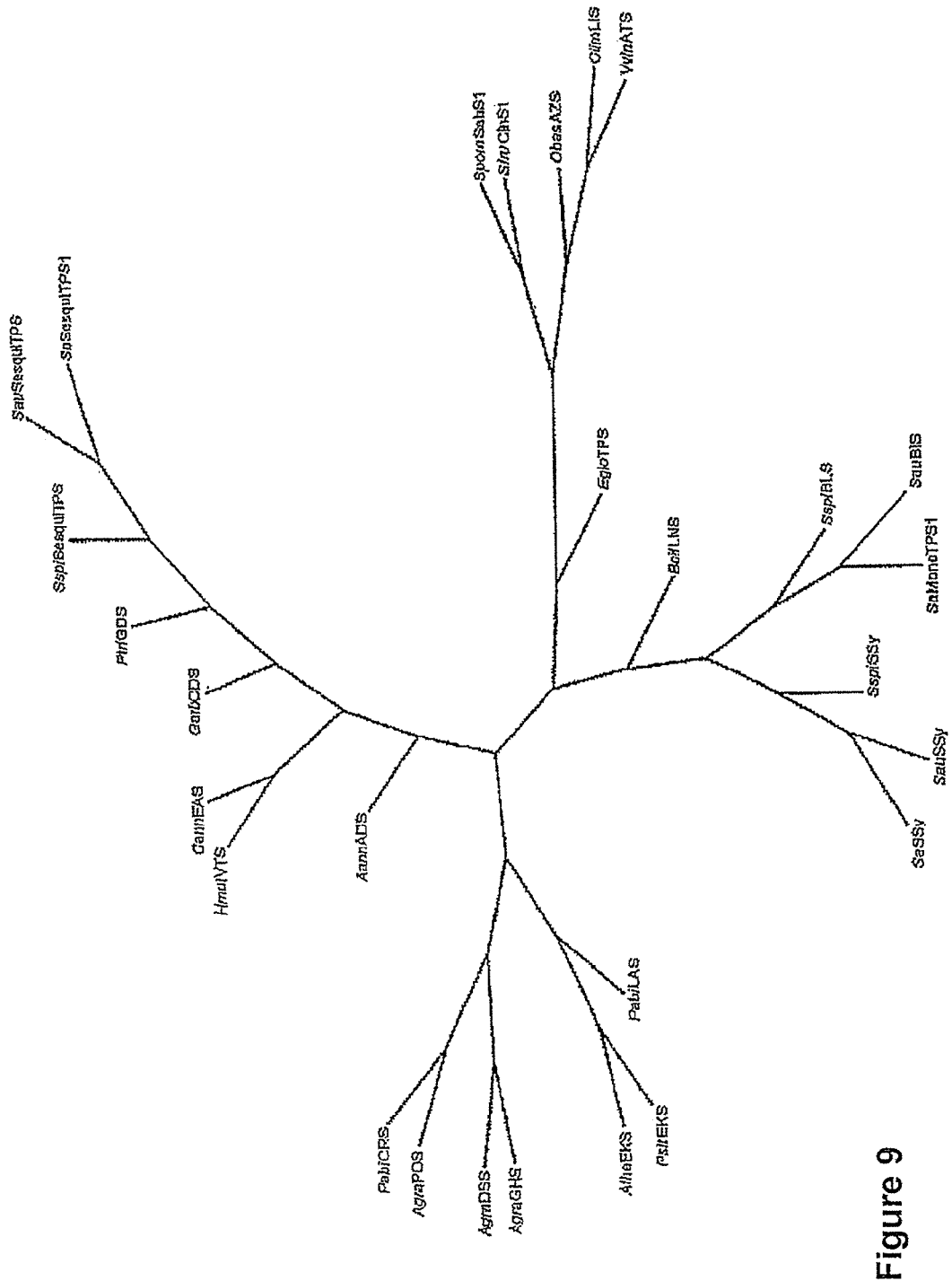
FIG. 9: Neighbor joining alignment tree of 28 different terpene synthase genes. Reference codes as for FIG. 8.

Enzyme assays using SaSSy with FPP as the substrate and $Mg^{2+}$ ion containing buffer produced a mixture of α-santalene (34.7%), α-trans-bergamotene (11.1%), epi-β-santalene (4.3%), β-santalene (41.3%) and small amounts of several other compounds as determined by GC-MS (FIG. 2A). The mass spectrum of the four compounds produced by the SaSSy enzyme (shown in FIG. 2A) are the same as those of natural β-santalene produced in sandalwood trees (see Adams (1995), cited above, for comparison profiles).

Incubation of FPP with heat-denatured enzyme resulted in no detectable products, indicating the enzyme was essential for product conversions.

Example 8

Comparison of Nucleic Acid Sequence

A Clustal multiple sequence alignment of terpene synthases (FB299123-125—terpene synthase from *Vetiveria zizanoides* (WO 2006/134523); AF484125—5-epi-aristolochene synthase from *Nicotiana attenuate*; AB438045—linalool synthase from *Backhousia citriodora*; Santalene—SaSSy santalene synthase of the present invention from *Santalum album*) is shown in FIG. 6. Linalool synthase from *Backhousia citriodora* is the most homologous protein; however, there is a general lack of similarity between santalene and the other TPS genes. An overhead single line indicates approximate regions indicated by Back and Chappell (Proc. Natl. Acad. Sci. U.S.A. 93:6841-6845 (1996)) as being important for specific product formation, and double lines for the ratio specific region of TEAS.

On the amino acid level, SaSSy santalene synthase was 56% identical to the previously discovered monoterpene synthase SamonoTPS1 (EU798692.1), 48% identical to a putative limonene synthase from *Ricinus communis* (EQ973796.1), and 45% identical to a linalool synthase from *Backhousia citriodora* (BAG82825.1).

Example 9

Plant Material Collection and RNA Extraction

Several 25 mm holes were drilled into mature *S. album, S. austrocaledonicum* and *S. spicatum* trees growing in plantations managed by the Forest Products Commission of WA. Wood shavings from the heartwood-sapwood transition zone were collected and frozen immediately in liquid nitrogen. The samples were transported to the lab where RNA was extracted using a modified protocol (N. Kolosova, B. Miller, S. Ralph, B. Ellis, C. Douglas, K. Ritland, J. Bohlmann, BioTechniques 36:821-824 (2004)). Wood shavings (10 g) were ground in liquid nitrogen and added to RNA extraction buffer (200 mM Tris-HCl, pH 8.5, 1.5% lithium dodecyl sulphate, 300 mM LiCl, 10 mM EDTA, 1% w/v sodium deoxycholate, 1% w/v Tergitol Nonidet P-40). RNAse inhibitors (5 mM thiourea, 1 mM aurintricarboxylic acid, 10 mM dithiothreitol, and 2% polyvinylpolypyrrolidone) were added to the buffer just prior to use. All solutions were prepared from DEPC treated, autoclaved water. Where possible, samples from the same tree were combined at the TE/NaCl resuspension step to concentrate the RNA sample. After LiCl precipitation, RNA was stored at −800° C. until transported to UBC Vancouver, Canada, for cDNA library construction.

Example 10

*Santalum album* cDNA Library Construction 1.4 μg of *S. album* xylem total RNA was used to create a cDNA library using the Clontech SMART-Creator library construction kit. RNA was reverse transcribed using SuperScript III reverse transcriptase (Invitrogen). cDNA was amplified using Phusion high-fidelity DNA polymerase and the universal primer (Clontech). This was digested with SfiI restriction endonuclease and cloned into pre-cut pDNR-LIB vector. The mixture was transformed by electroporation into 25 μL of phage resistant electrocompetent *E. coli* cells. The library titre was determined and sent to the Genome Sciences Centre, Vancouver, Canada, for bidirectional Sanger DNA sequencing. Reads were assembled using the CAP3 program with default settings. The sequences (6000 unique reads) were compared to the GenBan database for key specialised metabolism genes, particularly TPS genes and cytochrome P450s.

Example 11

Orthologous TPS Gene Discovery by RACE cDNA was generated for *S. austrocaledonicum* and *S. spicatum* in the same manner as before, except the cDNA was used directly as template for PCR. Primers based on the ORF of each gene were used for amplification (Table 3). Where products could not be amplified, 5'- and 3'-RACE were used to obtain the respective UTRs for more specific primer design. SesquiTPS1 gene orthologs were amplified in two rounds using a nested primer approach.

TABLE 3

Primers

| Open reading frame primers | | |
|---|---|---|
| Gene | Forward primer | Reverse primer |
| SaSSy | ATGGATTCTTCCACCGCCACCGCC | CGAGCTTACTACTCCTCGCCGAGAGG |
| SauSSy | ATGGATTCTTCCACCGCCACCGCC | CGAGCTTACTACTCCTCGCCGAGAGG |
| SspiSSy | ATGGATTCTTCCACCGCCACCGCC | CGAGCTTACTACTCCTCGCCGAGAGG |

| pET28b(+) cloning primers with incorporated restriction sites underlined | | |
|---|---|---|
| Gene | Forward primer | Reverse primer |
| SaSSy | AT<u>CCATGG</u>ATTCTTCCACCGCC | AT<u>CTCGAG</u>CTCCTCGCCGAGAGG |
| SauSSy | AT<u>CCATGG</u>ATTCTTCCACCGCC | AT<u>CTCGAG</u>CTCCTCGCCGAGAGG |
| SspiSSy | AC<u>GGATCC</u>AATGGATTCTTCCACCGCCAC | TA<u>CTCGAG</u>TTACTACTCCTCGCCGAG |

All products were first cloned into a high-copy storage vector (TOPO Zero Blunt, Invitrogen) for sequencing before being cloned into an expression vector. TPS genes amplified from several genotypes of *S. album* and *S. spicatum* were cloned and sequenced to examine potential nucleotide polymorphisms in the ORFs. Genomic DNA sequences for all three TPS genes were also cloned and sequenced for all three *Santalum* species. The same ORF primers used for successful cDNA amplifications were used on genomic DNA extracted from the same individuals from which RNA extractions were performed. These larger gDNA fragments (3-4 kb) were cloned and sent for sequencing (Macrogen, Korea).

Example 12

Bacterial Expression and Protein Isolation

All TPS genes were cloned into the pET28b(+) expression vector (Novagen, San Diego, Calif.) with a poly-histidine tag in frame. Depending on the restriction sites available, the $His_6$ tag was either N-terminal or C-terminal. Primers with appropriate restriction sites were used to amplify each gene, which was then digested, gel-purified and cloned into the pET28b (+) vector (Table 3). All pET28b(+) constructs were sequence-verified before proceeding to recombinant protein expression.

Expression vectors containing the TPS genes were transformed into chemically competent C41 *E. coli* cells (Avidis, Saint-Beauzire, France) containing the pRARE 2 plasmid isolated from Rosetta 2 competent cells (Novagen). Colonies were grown on LB plates containing kanamycin and chloramphenicol (50 µg/mL). Three independent colonies were picked and grown in a shaker overnight at 37° C. in 5 ml of LB with the same antibiotics. This culture was used to inoculate 400 mL of selective Terrific Broth. The cell suspension was grown with shaking at 37° C. until the $OD_{600}$=0.8. Isopropyl-β-D-thiogalacto-pyranoside (IPTG) was added to a final concentration of 0.2 mM and the mixture was shaken overnight at 16° C. Cell suspension was harvested by centrifugation at 4° C. and the cell pellet (~1 g) was frozen at −80° C. for future use.

Cell pellets were resuspended in 5 mL of lysis buffer containing 1 mg/mL lysozyme, 1 mM $MgCl_2$, 5 mM DTT, 0.01 mg/mL DNAse1 and RNAse1, 100 µL protease inhibitor cocktail (Sigma) and made in His-trap binding buffer (20 mM $Na_2HPO_4$ pH 7.4, 500 mM NaCl, 30 mM imidazole pH 7.4). On ice, the cell suspension was stirred thoroughly with a glass rod for 30 min. Lysate was then homogenized using a high pressure cell cruncher until the mixture was translucent, and rinsed with a further 5 mL of lysis buffer. The lysate was centrifuged at 12000×g at 4° C. for 1.25 h before being decanted. The cleared lysate (~12 mL) was purified using $Ni^{2+}$ affinity chromatography (GE healthcare) and eluted in 600 µL of elution buffer (20 mM $Na_2HPO_4$ pH 7.4, 500 mM NaCl, 500 mM imidazole pH 7.4). The eluted protein was desalted on a PD-10 desalting column (GE Healthcare) using 25 mM HEPES pH 7.4, 10% glycerol and 100 mM KCl. Fractions of a 3.5 mL elution were collected, with the middle being the most concentrated. Protein concentrations were determined using a NanoDrop spectrophotometer with extinction coefficients calculated by amino acid composition (ProtParam). SDS-PAGE was used to visualise the purified proteins.

Example 13

Enzyme Functional Characterisation and Kinetic Assays

Enzyme assays for all recombinant proteins were done in triplicate using the GC vial method described by O'Maille et al. (Anal. Biochem. 335:210-2175 (2004). For enzyme assays where only product identification was needed, 10 µg of protein was used in a final volume of 500 µL of reaction buffer (25 mM HEPES, 10% glycerol, 5 mM DTT and 10 mM of either $Mg^{2+}$ or $Mn^{2+}$. Substrates (FPP and GPP) were added to a final reaction concentration of 100 µM. Vials were overlaid with 500 µL of hexane to trap volatile products and incubated at 30° C. for 2 h. Mixtures were vortexed for 1 min to extract all volatiles and the vials were centrifuged to separate the organic layer.

For determination of steady-state enzyme kinetic constants, conditions were as described previously except the enzyme concentration was kept at 10 nM. Substrate concentrations ranged from 1 uM to 100 uM, and reactions were incubated at 30° C. for exactly 5 mins. Reactions were quenched by the addition of 500 µL 0.5 M EDTA, pH 8.0 and vortexed as above.

The kinetic properties of the three santalene synthases are very similar with a $K_m$ around 1.65 µM for each enzyme when FPP is used as substrate. $V_{max}$ for assays using FPP ranged from 0.42 µM $min^{-1}$ for SaSSy to 0.54 µM $min^{-1}$ for SauSSy. $K_{cat}$ was 0.67 $min^{-1}$ for SaSSy and 1.66 $min^{-1}$ for SauSSy, which are similar to those of other published synthases.

Example 14

GC-MS Analysis and Product Identification

Product mixtures were analysed by GC-MS in scan mode for product identification. A standard containing the three santalenes and α-trans-bergamotene was prepared by flash chromatography of 2 mL of neat *S. album* oil over silica and eluted in hexane. A final yield of 25 mg was resuspended in EtOAc and purity was confirmed by GC-FID with conditions described below. All mass spectra were compared to the NIST 2005 library and the literature. Retention indices were determined for all compounds using an n-alkane standard and compared to the literature (R. P. Adams, "Identification of essential oil components by gas chromatography/mass spectrometry," Allured Publishing Corporation, Carol Stream, Ill. (1995)).

GC-FID was performed on a Shimadzu GC2010 with a 30 m 0.25 mm ID, 0.25 µm film DB-WAX column with He as the carrier gas. Splitless injection (2 µL) was used for all analyses. Conditions were as follows: injector 200° C., detector 250° C., column flow rate 1 mL/min. Oven program: 40° C. for 3 min, then 8° C./min to 180° C., held 5 min, then 10° C./min to 220° C., held 10 min. Needle height was adjusted to only draw from the upper organic layer of all sample vials. GC-MS was performed on a Shimadzu GC2010 with the same DB-WAX column and using He as the carrier gas. Conditions were as follows: injector 200° C., MS interface 240° C., ion source 200° C. Oven program: 40° C. for 3 min, then 8° C./min to 180° C., held 5 min, then 10° C./min to 220° C., held 10 min. Solvent cut time was set to 5 min. For product identification, total ion monitoring was used, scanning from m/z 45 to m/z 300. For kinetic assays, single ion monitoring of the sesquiterpene base ions m/z 91, 93 and 94 were used. Likewise monoterpene base ions (m/z 69, 71 and 93) were monitored. An internal standard (isobutyl benzene, 30 µM) was added to the hexane used to overlay each reaction. Detector response factors were calculated based on the santalene standard prepared earlier and used to determine the product concentrations for kinetic analysis.

TABLE 4

GC-FID determination of reaction products of terpene synthases from FFP in the presence of magnesium or manganese

|  | Retention time | 1 | 2 | 3 | mean | 1 | 2 | 3 | mean |
|---|---|---|---|---|---|---|---|---|---|
|  |  | SaSSy with FPP Mg | | | | SaSSy with FPP Mn | | | |
| α-santalene | 15.101 | 46.4 | 43.8 | 45.6 | 45.3 | 9.5 | 9.9 | 10.1 | 9.8 |
| α-E-bergamotene | 15.288 | 16.3 | 15.3 | 16.4 | 16.0 | 75.7 | 73.4 | 74.9 | 74.7 |
| epi-β-santalene | 16.132 | 4.6 | 5.1 | 4.3 | 4.7 | 0.9 | 0.8 | 0.5 | 0.7 |
| β-santalene | 16.362 | 30.4 | 33.1 | 31.2 | 31.5 | 6.0 | 7.3 | 6.4 | 6.6 |
| Z-β-farnesene | 16.468 | 0.7 | 1.0 | 0.7 | 0.8 | 0.6 | 0.5 | 0.5 | 0.5 |
| E-β-farnesene | 16.927 | 1.7 | 1.7 | 1.7 | 1.7 | 7.4 | 8.0 | 7.5 | 7.6 |
|  |  | SauSSy with FPP Mg | | | | SauSSy with FPP Mn | | | |
| α-santalene | 15.093 | 51.7 | 51.5 | 50.7 | 51.3 | 10.3 | 10.5 | 9.7 | 10.2 |
| α-E-bergamotene | 15.278 | 13.8 | 14.6 | 15.2 | 14.5 | 72.5 | 73.8 | 74.4 | 73.6 |
| epi-β-santalene | 16.123 | 4.7 | 4.6 | 5.1 | 4.8 | 1.4 | 0.8 | 1.2 | 1.2 |
| β-santalene | 16.352 | 27.8 | 27.5 | 27.0 | 27.4 | 5.3 | 5.5 | 5.1 | 5.3 |
| Z-β-farnesene | 16.458 | 0.6 | 0.6 | 0.5 | 0.6 | 0.9 | 0.9 | 0.9 | 0.9 |
| E-β-farnesene | 16.917 | 1.5 | 1.3 | 1.5 | 1.4 | 8.3 | 8.5 | 8.6 | 8.5 |
|  |  | SspiSSy with FPP Mg | | | | SspiSSy with FPP Mn | | | |
| α-santalene | 15.093 | 46.3 | 47.4 | 48.1 | 47.3 | 7.2 | 7.4 | 7.3 | 7.3 |
| α-E-bergamotene | 15.28 | 19.6 | 19.2 | 18.9 | 19.2 | 79.0 | 78.6 | 79.1 | 78.9 |
| epi-β-santalene | 16.125 | 4.6 | 4.2 | 4.0 | 4.2 | 1.4 | 1.7 | 0.7 | 1.3 |
| β-santalene | 16.354 | 26.4 | 26.4 | 26.3 | 26.3 | 3.3 | 3.4 | 3.5 | 3.4 |
| Z-β-farnesene | 16.46 | 0.7 | 0.6 | 0.8 | 0.7 | 1.0 | 1.0 | 1.0 | 1.0 |
| E-β-farnesene | 16.919 | 2.5 | 2.2 | 2.0 | 2.2 | 8.1 | 8.0 | 8.4 | 8.2 |

Modifications of the above-described modes of carrying out the various embodiments of this invention will be apparent to those skilled in the art based on the above teachings related to the disclosed invention. The above embodiments of the invention are merely exemplary and should not be construed to be in any way limiting.

SEQUENCE LISTING

```
<160> NUMBER OF SEQ ID NOS: 9

<210> SEQ ID NO 1
<211> LENGTH: 1713
<212> TYPE: DNA
<213> ORGANISM: Santalum album
<220> FEATURE:
<223> OTHER INFORMATION: SaSSy DNA

<400> SEQUENCE: 1
atggattctt ccaccgccac cgccatgaca gctccattca ttgatcctac tgatcatgtg      60
aatctcaaaa ctgatacgga tgcctcagag aatcgaagga tgggaaatta taaacccagc     120
atttggaatt atgattttt acaatcactt gcaactcatc acaatattgt ggaagagagg      180
catctaaagc tagctgagaa gctgaagggc caagtgaagt ttatgtttgg ggcaccaatg     240
gagccgttag caaagctgga gcttgtggat gtggttcaaa ggcttgggct aaaccaccta     300
tttgagacag agatcaagga agcgctgttt agtatttaca aggatgggag caatggatgg     360
tggtttggcc accttcatgc gacatctctc cgatttaggc tgctacgaca gtgtgggctt     420
tttattcccc aagatgtgtt taaaacgttc caaaacaaga ctggggaatt tgatatgaaa     480
ctttgtgaca acgtaaaagg gctgctgagc ttatatgaag cttcatactt gggatggaag     540
ggtgaaaaca tcctagatga agccaaggcc ttcaccacca agtgcttgaa aagtgcatgg     600
gaaaatatat ccgaaaagtg gttagccaaa agagtgaagc atgcattggc tttgcctttg     660
cattggagag tccctcgaat cgaagctaga tggttcattg aggcatatga gcaagaagcg     720
aatatgaacc aacactact caaactcgca aaattagact ttaatatggt gcaatcaatt     780
catcagaaag agattgggga attagcaagg tggtgggtga ctactggctt ggataagtta     840
```

```
gcctttgcca ggaataattt actgcagagc tatatgtgga gctgcgcgat tgcttccgac    900
ccgaagttca aacttgctag agaaactatt gtcgaaatcg aagtgtact cacagttgtt    960 gacgatggat atgacgtcta tggttcaatc gacgaacttg atctctacac aagctccgtt   1020
gaaaggtgga gctgtgtgga aattgacaag ttgccaaaca cgttaaaatt aatttttatg   1080
tctatgttca acaagaccaa tgaggttggc cttcgagtcc agcatgagcg aggctacaat   1140
agcatcccta cttttatcaa agcgtgggtt gaacagtgta atcatacca gaaagaagca   1200 agatggttcc acggggaca cacgcctcca ttggaagaat atagcttgaa tggacttgtt   1260
tccataggat tccctctctt gttaatcacg ggctacgtgg caatcgctga gaacgaggct   1320
gcactggata agtgcacccc ccttcctgat cttctgcact actcctccct ccttagtcgc   1380
ctcatcaatg ataggaac gtctccggat gagatggcaa gaggcgataa tctgaagtca   1440
atccattgtt acatgaacga aactggggct tccgaggaag ttgctcgtga gcacataaag   1500
ggagtaatcg aggagaattg gaaaatactg aatcagtgct gctttgatca atctcagttt   1560
caggagcctt ttataacctt caatttgaac tctgttcgag ggtctcattt cttctatgaa   1620
tttggggatg gctttgtggt gacggatagc tggacaaagg ttgatatgaa gtccgttttg   1680 atcgaccta ttcctctcgg cgaggagtag taa                                 1713

<210> SEQ ID NO 2
<211> LENGTH: 569
<212> TYPE: PRT
<213> ORGANISM: Santalum album
<220> FEATURE:
<223> OTHER INFORMATION: SaSSy Protein

<400> SEQUENCE: 2

Met Asp Ser Ser Thr Ala Thr Ala Met Thr Ala Pro Phe Ile Asp Pro
  1               5                  10                  15

Thr Asp His Val Asn Leu Lys Thr Asp Thr Asp Ala Ser Glu Asn Arg
             20                  25                  30

Arg Met Gly Asn Tyr Lys Pro Ser Ile Trp Asn Tyr Asp Phe Leu Gln
         35                  40                  45

Ser Leu Ala Thr His His Asn Ile Val Glu Glu Arg His Leu Lys Leu
     50                  55                  60

Ala Glu Lys Leu Lys Gly Gln Val Lys Phe Met Phe Gly Ala Pro Met
 65                  70                  75                  80

Glu Pro Leu Ala Lys Leu Glu Leu Val Asp Val Val Gln Arg Leu Gly
                 85                  90                  95

Leu Asn His Leu Phe Glu Thr Glu Ile Lys Glu Ala Leu Phe Ser Ile
            100                 105                 110

Tyr Lys Asp Gly Ser Asn Gly Trp Trp Phe Gly His Leu His Ala Thr
        115                 120                 125

Ser Leu Arg Phe Arg Leu Leu Arg Gln Cys Gly Leu Phe Ile Pro Gln
    130                 135                 140

Asp Val Phe Lys Thr Phe Gln Asn Lys Thr Gly Glu Phe Asp Met Lys
145                 150                 155                 160

Leu Cys Asp Asn Val Lys Gly Leu Leu Ser Leu Tyr Glu Ala Ser Tyr
                165                 170                 175

Leu Gly Trp Lys Gly Glu Asn Ile Leu Asp Glu Ala Lys Ala Phe Thr
            180                 185                 190

Thr Lys Cys Leu Lys Ser Ala Trp Glu Asn Ile Ser Glu Lys Trp Leu
        195                 200                 205
```

Ala Lys Arg Val Lys His Ala Leu Ala Leu Pro Leu His Trp Arg Val
210             215                 220

Pro Arg Ile Glu Ala Arg Trp Phe Ile Glu Ala Tyr Glu Gln Glu Ala
225                 230                 235                 240

Asn Met Asn Pro Thr Leu Leu Lys Leu Ala Lys Leu Asp Phe Asn Met
                245                 250                 255

Val Gln Ser Ile His Gln Lys Glu Ile Gly Glu Leu Ala Arg Trp Trp
            260                 265                 270

Val Thr Thr Gly Leu Asp Lys Leu Ala Phe Ala Arg Asn Asn Leu Leu
        275                 280                 285

Gln Ser Tyr Met Trp Ser Cys Ala Ile Ala Ser Asp Pro Lys Phe Lys
290                 295                 300

Leu Ala Arg Glu Thr Ile Val Glu Ile Gly Ser Val Leu Thr Val Val
305                 310                 315                 320

Asp Asp Gly Tyr Asp Val Tyr Gly Ser Ile Asp Glu Leu Asp Leu Tyr
                325                 330                 335

Thr Ser Ser Val Glu Arg Trp Ser Cys Val Glu Ile Asp Lys Leu Pro
                340                 345                 350

Asn Thr Leu Lys Leu Ile Phe Met Ser Met Phe Asn Lys Thr Asn Glu
            355                 360                 365

Val Gly Leu Arg Val Gln His Glu Arg Gly Tyr Asn Ser Ile Pro Thr
370                 375                 380

Phe Ile Lys Ala Trp Val Glu Gln Cys Lys Ser Tyr Gln Lys Glu Ala
385                 390                 395                 400

Arg Trp Phe His Gly Gly His Thr Pro Pro Leu Glu Glu Tyr Ser Leu
                405                 410                 415

Asn Gly Leu Val Ser Ile Gly Phe Pro Leu Leu Leu Ile Thr Gly Tyr
                420                 425                 430

Val Ala Ile Ala Glu Asn Glu Ala Ala Leu Asp Lys Val His Pro Leu
            435                 440                 445

Pro Asp Leu Leu His Tyr Ser Ser Leu Leu Ser Arg Leu Ile Asn Asp
450                 455                 460

Ile Gly Thr Ser Pro Asp Glu Met Ala Arg Gly Asp Asn Leu Lys Ser
465                 470                 475                 480

Ile His Cys Tyr Met Asn Glu Thr Gly Ala Ser Glu Glu Val Ala Arg
                485                 490                 495

Glu His Ile Lys Gly Val Ile Glu Glu Asn Trp Lys Ile Leu Asn Gln
            500                 505                 510

Cys Cys Phe Asp Gln Ser Gln Phe Gln Glu Pro Phe Ile Thr Phe Asn
        515                 520                 525

Leu Asn Ser Val Arg Gly Ser His Phe Phe Tyr Glu Phe Gly Asp Gly
    530                 535                 540

Phe Gly Val Thr Asp Ser Trp Thr Lys Val Asp Met Lys Ser Val Leu
545                 550                 555                 560

Ile Asp Pro Ile Pro Leu Gly Glu Glu
                565

<210> SEQ ID NO 3
<211> LENGTH: 1713
<212> TYPE: DNA
<213> ORGANISM: Santalum austrocaledonicum
<220> FEATURE:
<223> OTHER INFORMATION: SauSSy DNA

<400> SEQUENCE: 3

```
atggattctt ccaccgccac cgccatgaca gctccattca ttgatcctac tgatcatgtg    60
aatctcaaaa ctgatactga tgcctcagag aatcgaagga tggggaatta taaacccagc   120
atttggaatt atgatttttt acaatcactt gcaactcatc acaatattgt ggaagagagg   180
catctaaagc tagctgagaa gctgaagggc aagtgaagt tatgtttgg ggcaccaatg    240 gagccgttag caaagctgga gcttgtggat gtggttcaaa ggctcgggct aaaccaccga   300
tttgagacag agatcaagga agcgctattt agtatttata aggacgagag caatggatgg   360
tggtttggcc accttcatgc gacatctctc cgatttaggc tgctacgaca gtgtgggctt   420
tttatccccc aggatgtgtt taaaacgttc aaaacaaaa ctggtgaatt tgatatgaaa    480
ctgtgtgaca acgtaaaagg gctgctgagc ttatatgaag cttcatactt gggatggaag   540
ggtgaaaaca tcctagatga agccaaggcc ttcgccacca agtacttgaa aagtgcatgg   600
gaaaatatat ctgaaaagtg gttagccaaa agagtgaagc atgcattggc tttacctttg   660
cattggagag tccctcgaat cgaagctaga tggttcattg aggcatatga gcaagaagcg   720
aatatgaacc caacactact caaactcgca aaattagact ttaatatggt gcaatcaatt   780
catcagaaag agattgggga attagcaagg tggtgggtga ctactggctt ggataagtta   840
gcctttgcta ggaataattt actgcaaagc tatatgtgga gctgcgcgat tgcttccgac   900
ccgaagttca aacttgctag agaaactatt gtcgaaatcg gaagtgtact cacagttgtt   960
gatgatgcat atgacgtcta tggttcaatg gacgaacttg atctctacac aagctccgtt  1020
gaaaggtgga gctgtgtaga aattgacaag ttgccaaaca cgttaaaatt gattttatg   1080 tctatgttta ataagaccaa tgaggttggc cttcgagtcc agcatgagcg aggctacaat  1140
agcatcccta cttttatcaa agcgtgggtt caacagtgta atcatacca gaaagaagca  1200 agatggttcc acggggaca cacgcctccg ttggaagaat atagcttgaa tggacttgtt   1260
tccataggat ccctctctct gttgatcacc ggctacgtgg caatcgctga aacgaggct   1320 gcactggata aagtgcaccc ccttcctgat cttctgcact actcctccct ccttagtcgc  1380
ctcatcaatg ataggaac gtctccggat gagatggcaa gaggcgataa tctgaagtca  1440
atccattgtt acatgaacgg aactgggct tccgaggaag ttgctcgtga gcacataaag   1500
ggagtaatcg aggagaattg gaaaatactg aatcagtgct gctttgatca atctcagttt  1560
caggagcctt tataaccctt caatttgaac tctgttcgag ggtctcattt cttctatgaa  1620
tttggggatg gctttggggt gacggatagc tggacaaagg ttgatatgaa gtccgttttg  1680
attgacccta ttcctctcgg cgaggagtag taa                                1713
```

<210> SEQ ID NO 4
<211> LENGTH: 569
<212> TYPE: PRT
<213> ORGANISM: Santalum austrocaledonicum
<220> FEATURE:
<223> OTHER INFORMATION: SauSSy Protein

<400> SEQUENCE: 4

Met Asp Ser Ser Thr Ala Thr Ala Met Thr Ala Pro Phe Ile Asp Pro
1               5                   10                  15

Thr Asp His Val Asn Leu Lys Thr Asp Thr Asp Ala Ser Glu Asn Arg
            20                  25                  30

Arg Met Gly Asn Tyr Lys Pro Ser Ile Trp Asn Tyr Asp Phe Leu Gln
        35                  40                  45

Ser Leu Ala Thr His His Asn Ile Val Glu Glu Arg His Leu Lys Leu

-continued

```
            50                  55                  60
Ala Glu Lys Leu Lys Gly Gln Val Lys Phe Met Phe Gly Ala Pro Met
 65                  70                  75                  80

Glu Pro Leu Ala Lys Leu Glu Leu Val Asp Val Gln Arg Leu Gly
                 85                  90                  95

Leu Asn His Arg Phe Glu Thr Glu Ile Lys Glu Ala Leu Phe Ser Ile
                100                 105                 110

Tyr Lys Asp Glu Ser Asn Gly Trp Trp Phe Gly His Leu His Ala Thr
                115                 120                 125

Ser Leu Arg Phe Arg Leu Leu Arg Gln Cys Gly Leu Phe Ile Pro Gln
130                 135                 140

Asp Val Phe Lys Thr Phe Gln Asn Lys Thr Gly Glu Phe Asp Met Lys
145                 150                 155                 160

Leu Cys Asp Asn Val Lys Gly Leu Leu Ser Leu Tyr Glu Ala Ser Tyr
                165                 170                 175

Leu Gly Trp Lys Gly Glu Asn Ile Leu Asp Glu Ala Lys Ala Phe Ala
                180                 185                 190

Thr Lys Tyr Leu Lys Ser Ala Trp Glu Asn Ile Ser Glu Lys Trp Leu
                195                 200                 205

Ala Lys Arg Val Lys His Ala Leu Ala Leu Pro Leu His Trp Arg Val
210                 215                 220

Pro Arg Ile Glu Ala Arg Trp Phe Ile Glu Ala Tyr Glu Gln Glu Ala
225                 230                 235                 240

Asn Met Asn Pro Thr Leu Leu Lys Leu Ala Lys Leu Asp Phe Asn Met
                245                 250                 255

Val Gln Ser Ile His Gln Lys Glu Ile Gly Glu Leu Ala Arg Trp Trp
                260                 265                 270

Val Thr Thr Gly Leu Asp Lys Leu Ala Phe Ala Arg Asn Asn Leu Leu
                275                 280                 285

Gln Ser Tyr Met Trp Ser Cys Ala Ile Ala Ser Asp Pro Lys Phe Lys
                290                 295                 300

Leu Ala Arg Glu Thr Ile Val Glu Ile Gly Ser Val Leu Thr Val Val
305                 310                 315                 320

Asp Asp Ala Tyr Asp Val Tyr Gly Ser Met Asp Glu Leu Asp Leu Tyr
                325                 330                 335

Thr Ser Ser Val Glu Arg Trp Ser Cys Val Glu Ile Asp Lys Leu Pro
                340                 345                 350

Asn Thr Leu Lys Leu Ile Phe Met Ser Met Phe Asn Lys Thr Asn Glu
                355                 360                 365

Val Gly Leu Arg Val Gln His Glu Arg Gly Tyr Asn Ser Ile Pro Thr
                370                 375                 380

Phe Ile Lys Ala Trp Val Gln Gln Cys Lys Ser Tyr Gln Lys Glu Ala
385                 390                 395                 400

Arg Trp Phe His Gly Gly His Thr Pro Leu Glu Glu Tyr Ser Leu
                405                 410                 415

Asn Gly Leu Val Ser Ile Gly Phe Pro Leu Leu Ile Thr Gly Tyr
                420                 425                 430

Val Ala Ile Ala Glu Asn Glu Ala Ala Leu Asp Lys Val His Pro Leu
                435                 440                 445

Pro Asp Leu Leu His Tyr Ser Ser Leu Leu Ser Arg Leu Ile Asn Asp
450                 455                 460

Ile Gly Thr Ser Pro Asp Glu Met Ala Arg Gly Asp Asn Leu Lys Ser
465                 470                 475                 480
```

```
Ile His Cys Tyr Met Asn Gly Thr Gly Ala Ser Glu Glu Val Ala Arg
                485                 490                 495

Glu His Ile Lys Gly Val Ile Glu Glu Asn Trp Lys Ile Leu Asn Gln
            500                 505                 510

Cys Cys Phe Asp Gln Ser Gln Phe Gln Glu Pro Phe Ile Thr Phe Asn
        515                 520                 525
Leu Asn Ser Val Arg Gly Ser His Phe Phe Tyr Glu Phe Gly Asp Gly
    530                 535                 540

Phe Gly Val Thr Asp Ser Trp Thr Lys Val Asp Met Lys Ser Val Leu
545                 550                 555                 560
Ile Asp Pro Ile Pro Leu Gly Glu Glu
                565
```

```
<210> SEQ ID NO 5
<211> LENGTH: 1713
<212> TYPE: DNA
<213> ORGANISM: Santalum spicatum
<220> FEATURE:
<223> OTHER INFORMATION: SspiSSy DNA

<400> SEQUENCE: 5
atggattctt ccaccgccac cgccacgaca gctccattta ttgatcatac tgatcatgtg     60
aatcttaaaa ttgataatga ttcctccgag agtcgaagga tgggcaatta taaacccagt    120
atttggaatt atgattttct gcaatcactt gcaatccatc acaatattgt ggaagagaag    180
catctaaagc tagctgagaa gctgaagggc caagtgatgt ctatgtttgg ggcaccaatg    240
gagccgttag caaagctgga gcttgtggat gtggttcaaa ggcttgggct aaaccaccaa    300
tttgagacag agatcaagga agccctattt agtgtttaca aggatgggag caatggatgg    360
tggtttggcc accttcatgc aacatctctt cgatttaggc tactacgaca gtgtgggctt    420
tttatccccc aggatgtgtt taaaacgttc cagagcaaaa ctgatgaatt tgatatgaaa    480
ctgtgtgaca acataaaagg gttgttgagc ttgtatgaag cttcattcct ggggtggaag    540
ggtgaaaaca tcctagatga agccaaggcc ttcgccacca agtacttgaa aaatgcatgg    600
gaaaatatat cccaaaagtg gctagccaaa agagtgaagc atgcactggc tttgcctctg    660
cactggagag tccctcgaat cgaggctaga tggttcattg aggcatatga gcaagaagag    720
aacatgaacc caacactact caaacttgca aaattagact ttaacatggt gcaatcaatt    780
catcagaaag agattgggga attagcaagg tggtgggtga ctactggctt ggataagtta    840
gcctttgcta ggaataattt actgcaaagc tatatgtgga gctgcgcgat tgcttccgac    900
ccaaagttca aacttgctag agaaactatt gtcgaaatcg gaagtgtact cacagttgtg    960
gacgatgcat atgatgtcta tggttcaatg gatgaacttg atcactacac atactccgtt   1020
gaaaggtgga gctgtgtaga aattgacaag ctgccaaaca cgttaaaatt gatttttatg   1080
tctatgttca acaagaccaa tgaggttggc cttcgagtcc agcatgagcg aggctacaac   1140
ggcatcccta cttttatcaa agcatgggtt gaacagtgta aagcatacca gaaagaggca   1200
agatggtacc atgggggaca cacgcctcca ttggaggaat atagcttgaa tggacttgtt   1260
tccataggat tccctctctt gttgatcacc ggctacatcg caatcgctga gaacgaggct   1320
gcactggata aagtgcaccc ccttcctgat cttctgcact actcctccct ccttagtcgc   1380
ctcatcaatg acatgggaac gtctccggac gagatggcaa gaggtgacaa tctgaagtca   1440
atccactgtt acatgaacga aactggggct tctgaggaag ttgctcgtga gcacataaaa   1500
```

```
ggaataatcg aggagaattg gaaaatactg aatcagtgct gctttgatca atctcagttt    1560
caggagcctt ttataacctt caatttgaac tctgttcgag ggtctcattt cttctatgaa    1620
tttggggatg gctttggggt gacagatagc tggacaaagg ttgatatgaa gtctgttttg    1680
atcgaccctc ttcctctcgg cgaggagtag taa                                 1713
```

<210> SEQ ID NO 6
<211> LENGTH: 569
<212> TYPE: PRT
<213> ORGANISM: Santalum spicatum
<220> FEATURE:
<223> OTHER INFORMATION: SspiSSy Protein

<400> SEQUENCE: 6

```
Met Asp Ser Ser Thr Ala Thr Ala Thr Thr Ala Pro Phe Ile Asp His
 1               5                  10                  15

Thr Asp His Val Asn Leu Lys Ile Asp Asn Asp Ser Ser Glu Ser Arg
                20                  25                  30

Arg Met Gly Asn Tyr Lys Pro Ser Ile Trp Asn Tyr Asp Phe Leu Gln
            35                  40                  45

Ser Leu Ala Ile His His Asn Ile Val Glu Glu Lys His Leu Lys Leu
        50                  55                  60

Ala Glu Lys Leu Lys Gly Gln Val Met Ser Met Phe Gly Ala Pro Met
 65                  70                  75                  80

Glu Pro Leu Ala Lys Leu Glu Leu Val Asp Val Val Gln Arg Leu Gly
                85                  90                  95

Leu Asn His Gln Phe Glu Thr Glu Ile Lys Glu Ala Leu Phe Ser Val
               100                 105                 110

Tyr Lys Asp Gly Ser Asn Gly Trp Trp Phe Gly His Leu His Ala Thr
            115                 120                 125

Ser Leu Arg Phe Arg Leu Leu Arg Gln Cys Gly Leu Phe Ile Pro Gln
        130                 135                 140

Asp Val Phe Lys Thr Phe Gln Ser Lys Thr Asp Glu Phe Asp Met Lys
145                 150                 155                 160

Leu Cys Asp Asn Ile Lys Gly Leu Leu Ser Leu Tyr Glu Ala Ser Phe
                165                 170                 175

Leu Gly Trp Lys Gly Glu Asn Ile Leu Asp Glu Ala Lys Ala Phe Ala
            180                 185                 190

Thr Lys Tyr Leu Lys Asn Ala Trp Glu Asn Ile Ser Gln Lys Trp Leu
        195                 200                 205

Ala Lys Arg Val Lys His Ala Leu Ala Leu Pro Leu His Trp Arg Val
    210                 215                 220

Pro Arg Ile Glu Ala Arg Trp Phe Ile Glu Ala Tyr Glu Gln Glu Glu
225                 230                 235                 240

Asn Met Asn Pro Thr Leu Leu Lys Leu Ala Lys Leu Asp Phe Asn Met
                245                 250                 255

Val Gln Ser Ile His Gln Lys Glu Ile Gly Glu Leu Ala Arg Trp Trp
            260                 265                 270

Val Thr Thr Gly Leu Asp Lys Leu Ala Phe Ala Arg Asn Asn Leu Leu
        275                 280                 285

Gln Ser Tyr Met Trp Ser Cys Ala Ile Ala Ser Asp Pro Lys Phe Lys
    290                 295                 300

Leu Ala Arg Glu Thr Ile Val Glu Ile Gly Ser Val Leu Thr Val Val
305                 310                 315                 320

Asp Asp Ala Tyr Asp Val Tyr Gly Ser Met Asp Glu Leu Asp His Tyr
```

```
                    325                 330                 335
Thr Tyr Ser Val Glu Arg Trp Ser Cys Val Glu Ile Asp Lys Leu Pro
            340                 345                 350
Asn Thr Leu Lys Leu Ile Phe Met Ser Met Phe Asn Lys Thr Asn Glu
                355                 360                 365
Val Gly Leu Arg Val Gln His Glu Arg Gly Tyr Asn Gly Ile Pro Thr
            370                 375                 380
Phe Ile Lys Ala Trp Val Glu Gln Cys Lys Ala Tyr Gln Lys Glu Ala
385                 390                 395                 400
Arg Trp Tyr His Gly His Thr Pro Leu Glu Glu Tyr Ser Leu
                405                 410                 415
Asn Gly Leu Val Ser Ile Gly Phe Pro Leu Leu Ile Thr Gly Tyr
            420                 425                 430
Ile Ala Ile Ala Glu Asn Glu Ala Ala Leu Asp Lys Val His Pro Leu
                435                 440                 445
Pro Asp Leu Leu His Tyr Ser Ser Leu Leu Ser Arg Leu Ile Asn Asp
450                 455                 460
Met Gly Thr Ser Pro Asp Glu Met Ala Arg Gly Asp Asn Leu Lys Ser
465                 470                 475                 480
Ile His Cys Tyr Met Asn Glu Thr Gly Ala Ser Glu Glu Val Ala Arg
                485                 490                 495
Glu His Ile Lys Gly Ile Ile Glu Asn Trp Lys Ile Leu Asn Gln
                500                 505                 510
Cys Cys Phe Asp Gln Ser Gln Phe Gln Glu Pro Phe Ile Thr Phe Asn
            515                 520                 525
Leu Asn Ser Val Arg Gly Ser His Phe Phe Tyr Glu Phe Gly Asp Gly
            530                 535                 540
Phe Gly Val Thr Asp Ser Trp Thr Lys Val Asp Met Lys Ser Val Leu
545                 550                 555                 560
Ile Asp Pro Ile Pro Leu Gly Glu Glu
                565

<210> SEQ ID NO 7
<211> LENGTH: 1713
<212> TYPE: DNA
<213> ORGANISM: Santalum album
<220> FEATURE:
<223> OTHER INFORMATION: SaSSy DNA

<400> SEQUENCE: 7
atggattctt ccaccgccac cgccatgaca gctccattca ttgatcctac tgatcatgtg      60
aatctcaaaa ctgatacgga tgcctcagag aatcgaagga tgggaaatta taaacccagc     120
atttggaatt atgattttt acaatcactt gcaactcatc acaatattgt ggaagagagg     180
catctaaagc tagctgagaa gctgaagggc caagtgaagt ttatgtttgg ggcaccaatg     240
gagccgttag caaagctgga gcttgtggat gtggttcaaa gcttgggct aaaccaccta     300 tttgagacag agatcaagga agcgctgttt agtatttaca aggatgggag caatggatgg     360
tggtttggcc accttcatgc gacatctctc cgatttaggc tgctacgaca gtgtgggctt     420
tttatttccc aagatgtgtt taaaacgttc aaaacaaga ctggggaatt tgatatgaaa     480
ctttgtgaca acgtaaaagg gctgctgagc ttatatgaag cttcatactt gggatggaag     540
ggtgaaaaca tcctagatga agccaaggcc ttcaccacca gtgcttgaa aagtgcatgg     600 gaaaatatat ccgaaaagtg gttagccaaa agagtgaagc atgcattggc tttgcctttg     660
```

```
cattggagag tccctcgaat cgaagctaga tggttcattg aggcatatga gcaagaagcg    720
aatatgaacc caacactact caaactcgca aaattagact ttaatatggt gcaatcaatt    780
catcagaaag agattgggga attagcaagg tggtgggtga ctactggctt ggataagtta    840
gcctttgcca ggaataattt actgcagagc tatatgtgga gctgcgcgat tgcttccgac    900
ccgaagttca aacttgctag agaaactatt gtcgaaatcg aagtgtact  cacagttgtt    960
gacgatggat atgacgtcta tggttcaatc gacgaacttg atctctacac aagctccgtt   1020
gaaggtgga  gctgtgtgga aattgacaag ttgccaaaca cgttaaaatt aattttatg    1080
tctatgttca acaagaccaa tgaggttggc cttcgagtcc agcatgagcg aggctacaat   1140
agcatcccta cttttatcaa agcgtgggtt gaacagtgta atcatacca gaaagaagca    1200
agatggttcc acgggggaca cacgcctcca ttggaagaat atagcttgaa tggacttgtt   1260
tccataggat tccctctctt gttaatcacg ggctacgtgg caatcgctga gaacgaggct   1320
gcactggata agtgcacccc cttcctgat  cttctgcact actcctccct ccttagtcgc   1380
ctcatcaatg atataggaac gtctccggat gagatggcaa gaggcgataa tctgaagtca   1440
atccattgtt acatgaacga aactggggct tccgaggaag ttgctcgtga gcacataaag   1500
ggagtaatcg aggagaattg gaaaatactg aatcagtgct gctttgatca atctcagttt   1560
caggagcctt ttataacctt caatttgaac tctgttcgag ggtctcattt cttctatgaa   1620
tttggggatg gctttgggt  gacggatagc tggacaaagg ttgatatgaa gtccgttttg   1680
atcgaccctc ttcctctcgg cgaggagtag taa                                1713
```

<210> SEQ ID NO 8
<211> LENGTH: 569
<212> TYPE: PRT
<213> ORGANISM: Santalum album
<220> FEATURE:
<223> OTHER INFORMATION: SaSSy Protein

<400> SEQUENCE: 8

```
Met Asp Ser Ser Thr Ala Thr Ala Met Thr Ala Pro Phe Ile Asp Pro
 1               5                  10                  15

Thr Asp His Val Asn Leu Lys Thr Asp Thr Asp Ala Ser Glu Asn Arg
             20                  25                  30

Arg Met Gly Asn Tyr Lys Pro Ser Ile Trp Asn Tyr Asp Phe Leu Gln
         35                  40                  45

Ser Leu Ala Thr His His Asn Ile Val Glu Glu Arg His Leu Lys Leu
     50                  55                  60

Ala Glu Lys Leu Lys Gly Gln Val Lys Phe Met Phe Gly Ala Pro Met
 65                  70                  75                  80

Glu Pro Leu Ala Lys Leu Glu Leu Val Asp Val Val Gln Arg Leu Gly
                 85                  90                  95

Leu Asn His Leu Phe Glu Thr Glu Ile Lys Glu Ala Leu Phe Ser Ile
            100                 105                 110

Tyr Lys Asp Gly Ser Asn Gly Trp Trp Phe Gly His Leu His Ala Thr
        115                 120                 125

Ser Leu Arg Phe Arg Leu Leu Arg Gln Cys Gly Leu Phe Ile Ser Gln
    130                 135                 140

Asp Val Phe Lys Thr Phe Gln Asn Lys Thr Gly Glu Phe Asp Met Lys
145                 150                 155                 160

Leu Cys Asp Asn Val Lys Gly Leu Leu Ser Leu Tyr Glu Ala Ser Tyr
                165                 170                 175
```

Leu Gly Trp Lys Gly Glu Asn Ile Leu Asp Glu Ala Lys Ala Phe Thr
            180                 185                 190

Thr Lys Cys Leu Lys Ser Ala Trp Glu Asn Ile Ser Glu Lys Trp Leu
        195                 200                 205

Ala Lys Arg Val Lys His Ala Leu Ala Leu Pro Leu His Trp Arg Val
    210                 215                 220

Pro Arg Ile Glu Ala Arg Trp Phe Ile Glu Ala Tyr Glu Gln Glu Ala
225                 230                 235                 240

Asn Met Asn Pro Thr Leu Leu Lys Leu Ala Lys Leu Asp Phe Asn Met
                245                 250                 255

Val Gln Ser Ile His Gln Lys Glu Ile Gly Glu Leu Ala Arg Trp Trp
            260                 265                 270

Val Thr Thr Gly Leu Asp Lys Leu Ala Phe Ala Arg Asn Asn Leu Leu
        275                 280                 285

Gln Ser Tyr Met Trp Ser Cys Ala Ile Ala Ser Asp Pro Lys Phe Lys
    290                 295                 300

Leu Ala Arg Glu Thr Ile Val Glu Ile Gly Ser Val Leu Thr Val Val
305                 310                 315                 320

Asp Asp Gly Tyr Asp Val Tyr Gly Ser Ile Asp Glu Leu Asp Leu Tyr
                325                 330                 335

Thr Ser Ser Val Glu Arg Trp Ser Cys Val Glu Ile Asp Lys Leu Pro
            340                 345                 350

Asn Thr Leu Lys Leu Ile Phe Met Ser Met Phe Asn Lys Thr Asn Glu
        355                 360                 365

Val Gly Leu Arg Val Gln His Glu Arg Gly Tyr Asn Ser Ile Pro Thr
    370                 375                 380

Phe Ile Lys Ala Trp Val Glu Gln Cys Lys Ser Tyr Gln Lys Glu Ala
385                 390                 395                 400

Arg Trp Phe His Gly His Thr Pro Leu Glu Glu Tyr Ser Leu
                405                 410                 415

Asn Gly Leu Val Ser Ile Gly Phe Pro Leu Leu Leu Ile Thr Gly Tyr
            420                 425                 430

Val Ala Ile Ala Glu Asn Glu Ala Ala Leu Asp Lys Val His Pro Leu
        435                 440                 445

Pro Asp Leu Leu His Tyr Ser Ser Leu Leu Ser Arg Leu Ile Asn Asp
    450                 455                 460

Ile Gly Thr Ser Pro Asp Glu Met Ala Arg Gly Asp Asn Leu Lys Ser
465                 470                 475                 480

Ile His Cys Tyr Met Asn Glu Thr Gly Ala Ser Glu Glu Val Ala Arg
                485                 490                 495

Glu His Ile Lys Gly Val Ile Glu Glu Asn Trp Lys Ile Leu Asn Gln
            500                 505                 510

Cys Cys Phe Asp Gln Ser Gln Phe Gln Glu Pro Phe Ile Thr Phe Asn
        515                 520                 525

Leu Asn Ser Val Arg Gly Ser His Phe Phe Tyr Glu Phe Gly Asp Gly
    530                 535                 540

Phe Gly Val Thr Asp Ser Trp Thr Lys Val Asp Met Lys Ser Val Leu
545                 550                 555                 560

Ile Asp Pro Ile Pro Leu Gly Glu Glu
                565

<210> SEQ ID NO 9
<211> LENGTH: 4088
<212> TYPE: DNA

<213> ORGANISM: Santalum album
<220> FEATURE:
<223> OTHER INFORMATION: SaSSy genomic DNA

<400> SEQUENCE: 9

```
atggattctt ccaccgccac cgccatgaca gctccattca ttgatcctac tgatcatgtg    60
aatctcaaaa ctgatacgga tgcctcagag aatcgaagga tgggaaatta taaacccagc   120
atttggaatt atgatttttt acaatcactt gcaactcatc acaatattgt ggtacatata   180
tatatatata gtagcctata atatttaatt ttgtttgtgt cagagtttct tttcggtgat   240
aaaaatataa caagtcatac gccaccttag ggtgactcct cctggcgccc agcaaccact   300
tctctttagt attttttttt cattttatct tttatgtttt tatgctttttt tttttttttt   360
gagaatgtga gtgtcaaact tattaacagg tccactaatt ccttgaggga ttgcgctag    420
tttttagcag cagtcttcgg ataaatgctc gccacatatg cataatatgt cgagttatct   480
tttcagactc aaatctatca tcttagggtt gtggaccttc tcttctcttc actattttg    540
ccgaacaata aacacaattg cttagagccc ttgtggacta gcccgagatt tgtttggctt   600
aaatgctgcc acacaagctt catattattt aatataactc attcatctgt tttgctctat   660
tatcgtagcc tgtggatcac cttcaatatg gtgctagtaa attttgcct ccttaaaatt    720
gagtcacata tctctattgt gattttgtcc tacgtattat ttgttagcta atggaggaa    780
atacacagga agagaggcat ctaaagctag ctgagaagct gaaggccaa gtgaagttta    840
tgtttggggc accaatggag ccgttagcaa agctggagct tgtggatgtg gttcaaaggc   900
ttgggctaaa ccacctattt gagacagaga tcaaggaagc gctgtttagt atttacaagg   960
atgggagcaa tggatggtgg tttggccacc ttcatgcgac atctctccga tttaggctgc  1020
tacgacagtg tgggcttttt attccccaag gtacgtctag cttaaatctt aattaggccc  1080
atgttttaat tgttggaata taataaacgt ttctttatcg ttccttagtt ataatcagcg  1140
gaccatccaa tcaaaaacca attgggtaac tcttgatgta aatattaaca gagtcatgac  1200
caacatcatt aatataattt agagggtatg actgagcatt aactacgaca gtatttcttg  1260
taagtggagg tcagatattt ttttgctaga tcttgtaata gaatatttat tagcctctgt  1320
tatacccgtc tgtatatgtg cacgcacatc ctagaatttt gtattccttt ctattaattt  1380
ttgtgttttc tatttggaaa ctcatatact tgcatatttt tgtgttaatt ttctgtgata  1440
cagaacgttc caaacaaga ctggggaatt tgatatgaaa ctttgtgaca acgtaaaagg   1500
gctgctgagc ttatatgaag cttcatactt gggatggaag ggtgaaaaca tcctagatga  1560
agccaaggcc ttcaccacca agtgcttgaa aagtgcatgg gaaaatatat ccgaaaagtg  1620
gttagccaaa agagtgaagc atgcattggc tttgcctttg cattggagag tccctcgaat  1680
cgaagctaga tggttcattg aggcatatga gcaagaagcg aatatgaacc caacactact  1740
caaactcgca aaattagact ttaatatggt gcaatcaatt catcagaaag agattgggga  1800
attagcaagg tattatcttc atattaaatc cgtcaagtca aatgatctaa tacatggtgc  1860
acttagagtg acaggggata caatatcatt attctcaatg agcaaggcta cacctttaa   1920
aggatgctat tttgagaaaa gattttaaaa agatagcctt ttttatagtg gcatcttctt  1980
tgcatgcata catctttgtc tacttataaa caatggtatc cctaaaaaag tcaaaaaaaa  2040
attccctcca aaaaccttaa ttttttgaga atgggtcgat atcaaatcta ataatttttct 2100
tttgccaaaa aaaatctaat acttttctcc agaaaacaga aaacctgaat agtcaaagag  2160
cttttgacccg acaagactgt gcctcgcttt tcccctataa gctctacaca cacatgcact  2220
```

```
agcaatttat ctttgacttt tcttcttctt ttcttttttt cctttctttt ttcatattta   2280
tgatgattat cattttccct aattattacc aggattatca ttttcttggg taatattgtt   2340
attattagca ttttccttgt tgaacaaatt tgatttccag gtggtgggtg actactggct   2400
tggataagtt agcctttgcc aggaataatt tactgcagag ctatatgtgg agctgcgcga   2460
ttgcttccga cccgaagttc aaacttgcta gagaaactat tgtcgaaatc ggaagtgtac   2520
tcacagttgt tgacgatgga tatgacgtct atggttcaat cgacgaactt gatctctaca   2580
caagctccgt tgaaaggtta tttgtatact ctttcgatgt tccataatat atttcgaatc   2640
atatcgatgg tgaaagtagt aattattgaa aaatctattt gtggatgaat tttcttatcg   2700
tgttacttat tcaggtggag ctgtgtggaa attgacaagt tgccaaacac gttaaaatta   2760
atttttatgt ctatgttcaa caagaccaat gaggttggcc ttcgagtcca gcatgagcga   2820
ggctacaata gcatccctac ttttatcaaa gcggtaaata attaccataa ttactatttt   2880
ctctaagata aaacaaggtt taatattcca tttaatgagt attattttgt gaaaaaaata   2940
ttatttcagt gggttgaaca gtgtaaatca taccagaaag aagcaagatg gttccacggg   3000
ggacacacgc ctccattgga agaatatagc ttgaatggac ttgtttccat aggattccct   3060
ctcttgttaa tcacgggcta cgtggcaatc gctgagaacg aggctgcact ggataaagtg   3120
cacccccttc ctgatcttct gcactactcc tccctcctta gtcgcctcat caatgatata   3180
ggaacgtctc cggtaagctc gtaaacattt ttataagtct ttttataaac atatagtcaa   3240
atattctttt gagtccagat tcataaagtc cagaattttt attttaaaac caattggtaa   3300
gagtcataga ttttgatgt ggaactatag cctcaatata tatggcaaca cgtgggcaaa   3360
ttttacttag ggtgacatga agcatgctta gtagtagaag ttaaagaaga gtaaattgcc   3420
cgaatctcat actatgataa agtccactgt gggcaatgtt ctcgacaagc gttcacaagt   3480
ggcaacaacc tgctttgcta ccatgcaatc gttcgtggag tttcaccttta aaatcaatcg   3540 gaattaggta aaataaacca aaatttattt aattgcatat gtgggacttt aattgctccc   3600
aatattctta attcacttgg agccaccaaa aagaactctt gccataatct aatgaagctc   3660
aaattgagtt ggtagtacaa tattggaaat gtaaatgatt aaaggcataa gtcttgactt   3720
tgggacatcg cccaacagtc aatatcaagt gaataatatt atttggtggt tttgataatc   3780
aggatgagat ggcaagaggc gataatctga agtcaatcca ttgttacatg aacgaaactg   3840
gggcttccga ggaagttgct cgtgagcaca taaagggagt aatcgaggag aattggaaaa   3900
tactgaatca gtgctgcttt gatcaatctc agtttcagga gccttttata accttcaatt   3960
tgaactctgt tcgagggtct catttcttct atgaatttgg ggatggcttt ggggtgacgg   4020
atagctggac aaaggttgat atgaagtccg ttttgatcga ccctattcct ctcggcgagg   4080
agtagtaa                                                            4088
```

The invention claimed is:

1. A host cell, comprising a cDNA molecule that encodes a *Santalum* species terpene synthase that comprises:
   (i) the sequence of amino acid resides set forth in SEQ ID NO:2, 4 or 6 or a catalytically active fragment thereof; or
   (ii) a sequence of amino acid residues that has at least 95% or greater sequence identity to the sequence of amino acid residues set forth in SEQ ID NO: 2, or a catalytically active fragment thereof, wherein:
   the cDNA molecule is heterologous to the cell; and the encoded synthase catalyzes the production of an α-santalene, α-trans-bergamotene, epi-β-santalene and β-santalene concurrently.

2. The host cell of claim 1, wherein the encoded synthase comprises a serine in place of the proline at residue 143 of SEQ ID NO: 2.

3. A vector, comprising a cDNA molecule that encodes a *Santalum* species terpene synthase that comprises:
   (i) the sequence of amino acid resides set forth in SEQ ID NO:2, 4 or 6 or a catalytically active fragment thereof; or
   (ii) a sequence of amino acid residues that has at least 95% or greater sequence identity to the sequence of amino acid residues set forth in SEQ ID NO: 2, or a catalytically active fragment thereof,
   wherein the encoded synthase catalyzes the production of an α-santalene, α-trans-bergamotene, epi-β-santalene and β-santalene concurrently.

4. The vector of claim 3, wherein the vector is a prokaryotic vector, viral vector, or a eukaryotic vector.

5. The vector of claim 3 that is an expression vector.

6. A method for preparing a terpene synthase, comprising the step of culturing the cell of claim 1 under conditions that provide for expression of the encoded terpene synthase.

7. The method of claim 6, further comprising purifying the terpene synthase.

8. A method of making a terpene, comprising: a) contacting an acyclic pyrophosphate terpene precursor with the terpene synthase encoded by a nucleic acid cDNA molecule to produce a terpene; and, b) optionally, isolating the terpene produced in step (a), wherein:
   the cDNA molecule that encodes a *Santalum* species terpene synthase comprises:
   (i) the sequence of amino acid resides set forth in SEQ ID NO:2, 4 or 6 or a catalytically active fragment thereof; or
   (ii) a sequence of amino acid residues that has at least 95% or greater sequence identity to the sequence of amino acid residues set forth in SEQ ID NO: 2, or a catalytically active fragment thereof;
   the encoded synthase catalyzes the production of an α-santalene, α-transbergamotene, epi-β-santalene and β-santalene concurrently; and
   if the terpene is produced in a host cell, the cDNA molecule is heterologous to the host cell.

9. The method of claim 8, wherein: the terpene synthase expressed in a cell is heterologous to the cell; the acyclic pyrophosphate terpene precursor is expressed in the same cell as the terpene synthase; and the step of contacting the acyclic pyrophosphate terpene precursor occurs in the cell.

10. The method of claim 9, wherein the terpene is produced by a method comprising cultivating the cell under conditions conducive to the production of a terpene.

11. The method of claim 9, further comprising isolating a terpene produced by the cell.

12. The method of claim 9, wherein the acyclic pyrophosphate terpene precursor is selected from among geranyl-pyrophosphate (GPP), farnesyl-diphosphate (FPP) and geranylgeranyl-pyrophosphate (GGPP).

13. The method of claim 8, wherein synthesized terpenes include α-santalene, α-trans-bergamotene, epi-β-santalene, and β-santalene in proportions relative to each other such that upon processing the terpenes to alcohols, the yield of santalols and bergamotols is similar to the natural oil of *Santalum album* sandalwood.

14. The method claim 8, wherein the terpene synthase is encoded by a sequence of nucleotides that has at least 98% sequence identity to the sequence of nucleotides in SEQ ID NO: 1 that encodes the terpene synthase.

15. The method of claim 8, wherein a terpene that is produced is selected from among α-santalene, α-trans-bergamotene, epi-β-santalene, and β-santalene and mixtures thereof.

16. The method of claim 8, wherein the terpene is selected from among (+)-epi-β-santalene, (−)-β-santalene, (+)-β-santalene, (+)-α-santalene and (−)-α-santalene.

17. The method of claim 8, wherein a mixture of terpenes is produced.

18. The method of claim 8, further comprising processing a resulting terpene to an alcohol.

19. The method of claim 18, wherein the alcohol is selected from among α-santalol, β-santalol, α-trans-bergamotol, epi-β-santalol and mixtures thereof.

20. The host cell of claim 1, further comprising a P450 enzyme.

21. The method of claim 8, further comprising processing the terpene that is produced by contacting it with a P450 enzyme to produce a processed terpene.

22. The method of claim 21, wherein:
   the terpene synthase is expressed in a host cell; and
   the step of contacting the acyclic pyrophosphate terpene precursor occurs in the cell.

23. The method of claim 8 that is performed in vitro.

24. The method of claim 21, wherein the processed terpene is isolated.

25. The method of claim 21, wherein the terpene is isolated before it is processed.

26. The method of claim 21, wherein the terpene produced in step a) is isolated; and is processed by contacting it with a P450 enzyme.

* * * * *